United States Patent
Howard et al.

(10) Patent No.: US 9,102,704 B2
(45) Date of Patent: Aug. 11, 2015

(54) SYNTHESIS METHOD AND INTERMEDIATES USEFUL IN THE PREPARATION OF PYRROLOBENZODIAZEPINES

(71) Applicant: SPIROGEN SÀRL, St-Légier-la-Chiésaz (CH)

(72) Inventors: Philip Wilson Howard, London (GB); Arnaud Tiberghien, London (GB)

(73) Assignee: SPIROGEN SARL, St-Legier-la Chiesaz (CH)

( * ) Notice: Subject to any disclaimer, the term of this patent is extended or adjusted under 35 U.S.C. 154(b) by 0 days.

(21) Appl. No.: 14/351,166

(22) PCT Filed: Oct. 12, 2012

(86) PCT No.: PCT/EP2012/070232
§ 371 (c)(1),
(2) Date: Apr. 11, 2014

(87) PCT Pub. No.: WO2013/053872
PCT Pub. Date: Apr. 18, 2013

(65) Prior Publication Data
US 2014/0275522 A1    Sep. 18, 2014

Related U.S. Application Data

(60) Provisional application No. 61/547,207, filed on Oct. 14, 2011.

(51) Int. Cl.
C07K 5/062    (2006.01)
C07F 7/18    (2006.01)
(Continued)

(52) U.S. Cl.
CPC .......... *C07K 5/06052* (2013.01); *C07D 207/20* (2013.01); *C07D 207/24* (2013.01);
(Continued)

(58) Field of Classification Search
USPC .......... 540/487, 496; 548/534, 532, 523, 539, 548/406, 519
See application file for complete search history.

(56) References Cited

U.S. PATENT DOCUMENTS

| | | |
|---|---|---|
| 3,523,941 A | 8/1970 | Leimgruber et al. |
| 3,524,849 A | 8/1970 | Batcho et al. |
| 3,619,374 A | 11/1971 | Berger et al. |
| 4,185,016 A | 1/1980 | Takanabe et al. |
| 4,239,683 A | 12/1980 | Takanabe et al. |
| 4,309,437 A | 1/1982 | Ueda et al. |
| 5,418,241 A | 5/1995 | Jegham et al. |

(Continued)

FOREIGN PATENT DOCUMENTS

| | | |
|---|---|---|
| EP | 1193270 | 4/2002 |
| FR | 2027356 | 12/1969 |

(Continued)

OTHER PUBLICATIONS

Adams et al., "Molecular modelling of a sequence-specific DNA-binding agent based on the pyrrolo[2,1-c][1,4]benzodiazepines," Pharm. Pharmacol. Commun. (1999) 5:555-560.
Althius, T. H. and Hess, H. J., "Synthesis and Identification of the Major Metabolites of Prazosin Formed in Dog and Rat," *J. Medicinal Chem.* (1977) 20(1):146-148.
Arima et al., "Studies on Tomaymycin, a New Antibiotic. I. Isolation and Properties of Tomaymycin," *J. Antibiotics* (1972) 25:437-444.
Berge et al., "Pharmaceutical Salts," J. Pharm. Sci. (1977) 66:1-19.
Berry, J. M. et al., "Solid-phase synthesis of DNA-interactive pyrrolo[2,1-c][1,4]benzodiazepines," *Tetrahedron Letters* (2000) 41:6171-6174.
Bose et al., "New Approaches to Pyrrolo[2,1-c][1,4]benzodiazepines: Synthesis, DNA-binding and cytotoxicity of DC-81," *Tetrahedron*, 48, 751-758 (1992).

(Continued)

*Primary Examiner* — Kristin Vajda
(74) *Attorney, Agent, or Firm* — Michael Best & Friedrich LLP

(57) ABSTRACT

A compound of formula I wherein: $R^7$ is selected from: $OR^A$, where $R^A$ is selected from $C_{1-4}$ saturated alkyl, optionally substituted by phenyl, which may bear a chloro substituent, pyridyl and furanyl; chloro; $NH_2$; $-CH_2-O-C(=O)Me$; $R^8$ is $OProt^O$, where $Prot^O$ is a silicon-based oxygen protecting group orthogonal to $R^c$; $R^9$ is selected from H, methyl and methoxy; $R^s$ is selected from $CF_3$, $(CF_2)_3CF_3$, $CH_3$ and (formula 2) and $R^c$ is selected from: (i) $C(=O)-OR^{C1}$, where $R^{C1}$ is a saturated $C_{1-4}$ alkyl group; (ii) $-CH_2-O-C(=O)R^{C2}$, where $R^{C2}$ is methyl or phenyl; (iii) $CH_2-O-Si-(R^{Si1})(R^{Si2})(R^{Si3})$, where $R^{Si1}$, $R^{Si2}$, $R^{Si3}$ are independently selected from $C_{1-6}$ a saturated alkyl group and a phenyl group; and (iv) $C(-YR^{C3})(-YR^{C4})$ where each Y is independently O or S, and where $R^{C3}$ and $R^{C4}$ are independently a saturated $C_{1-4}$ alkyl group, or together form a $C_{2-3}$ alkylene.

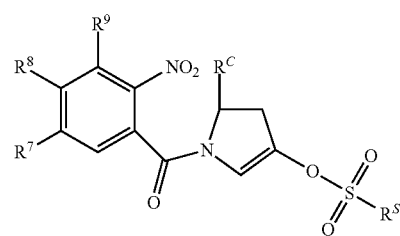

I

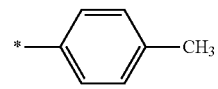

II

29 Claims, No Drawings

(51) Int. Cl.

| | |
|---|---|
| *C07D 401/12* | (2006.01) |
| *C07D 409/12* | (2006.01) |
| *C07D 413/12* | (2006.01) |
| *C07D 487/04* | (2006.01) |
| *C07D 207/20* | (2006.01) |
| *C07D 207/24* | (2006.01) |
| *C07D 207/27* | (2006.01) |
| *C07D 519/00* | (2006.01) |

(52) U.S. Cl.
CPC ............ *C07D207/27* (2013.01); *C07D 401/12* (2013.01); *C07D 409/12* (2013.01); *C07D 413/12* (2013.01); *C07D 487/04* (2013.01); *C07D 519/00* (2013.01); *C07F 7/1804* (2013.01)

(56) References Cited

U.S. PATENT DOCUMENTS

| | | | |
|---|---|---|---|
| 6,562,806 | B1 | 5/2003 | Thurston et al. |
| 6,608,192 | B1 | 8/2003 | Thurston et al. |
| 6,660,856 | B2 | 12/2003 | Wang |
| 6,747,144 | B1 | 6/2004 | Thurston et al. |
| 6,909,006 | B1 | 6/2005 | Thurston et al. |
| 7,049,311 | B1 | 5/2006 | Thurston et al. |
| 7,067,511 | B2 | 6/2006 | Thurston et al. |
| 7,265,105 | B2 | 9/2007 | Thurston et al. |
| 7,407,951 | B2 | 8/2008 | Thurston et al. |
| 7,429,658 | B2 | 9/2008 | Howard et al. |
| 7,528,126 | B2 | 5/2009 | Howard et al. |
| 7,557,099 | B2 | 7/2009 | Howard et al. |
| 7,612,062 | B2 | 11/2009 | Howard et al. |
| 7,704,924 | B2 | 4/2010 | Thurston et al. |
| 2003/0195196 | A1 | 10/2003 | Thurston et al. |
| 2004/0138269 | A1 | 7/2004 | Sun et al. |
| 2004/0198722 | A1 | 10/2004 | Thurston et al. |
| 2007/0191349 | A1 | 8/2007 | Howard et al. |
| 2007/0249591 | A1 | 10/2007 | Howard et al. |
| 2008/0090812 | A1 | 4/2008 | Pepper et al. |
| 2008/0214525 | A1 | 9/2008 | Howard et al. |
| 2013/0035484 | A1 | 2/2013 | Howard et al. |

FOREIGN PATENT DOCUMENTS

| | | |
|---|---|---|
| FR | 2586683 | 3/1987 |
| GB | 1299198 | 12/1972 |
| JP | 53-82792 | 7/1978 |
| JP | 57131791 | 8/1982 |
| JP | 58180487 | 10/1983 |
| WO | WO 92/19620 | 11/1992 |
| WO | WO 93/18045 | 9/1993 |
| WO | WO 00/12506 | 3/2000 |
| WO | WO 00/12507 | 3/2000 |
| WO | WO 00/12508 | 3/2000 |
| WO | WO 00/12509 | 3/2000 |
| WO | WO 2004/043963 | 5/2004 |
| WO | WO 2005/023814 | 3/2005 |
| WO | WO 2005/040170 | 5/2005 |
| WO | WO 2005/042535 | 5/2005 |
| WO | WO 2005/085250 | 9/2005 |
| WO | WO 2005/085251 | 9/2005 |
| WO | WO 2005/085259 | 9/2005 |
| WO | WO 2005/085260 | 9/2005 |
| WO | WO 2005/110423 | 11/2005 |
| WO | WO 2010/010347 | 1/2010 |
| WO | WO 2010043880 A1 * | 4/2010 ............ C07D 487/04 |

OTHER PUBLICATIONS

Bose, D.S. et al., "Effect of linker length on DNA-binding affinity, cross-linking efficiency and cytotoxicity of C8 linked pyrrolobenzodiazepine dimers," J. Chem. Soc. Chem. Commun. (1992) 20:1518-1520.

Bose, D.S. et al., "Rational Design of a Highly Efficient Irreversible DNA Interstrand Cross-Linking Agent Based on the Pyrrolobenzodiazepine Ring System," *J Am. Chem. Soc.*, 114, 4939-4941 (1992).

Chen, Z. et al., "A novel approach to the synthesis of cytotoxic C2-C3 unsaturated pyrrolo[2,1-c][1,4]benzodiazepines (PBDs) with conjugated acrylyl C2-substituents," Biorg. Med. Chem. Lett. (2004) 14:1547-1549.

Cooper, N. et al., "Synthesis of novel PBDs as anti-tumour agents," Chem. Commun. (2002) 16:1764-1765.

Courtney, S. M. et al., "A new convenient procedure for the synthesis of pyrrolo[2,1-c][1,4]benzodiazepines", *Tetrahedron Letters*, vol. 34, No. 33, 5327-28 (1993).

Cramer, N. et al., "Enantioselective total synthesis of cylindramide," Angew. Chem. Int. Ed. (2005) 44:820-822.

Farmer, J.D. et al., "DNA binding properties of a new class of linked anthramycin analogs,", *Chemical Abstracts*, Abstract No. 239940r, vol. 114, No. 25, 25 899-903 (1991).

Foloppe, M.P. et al., "DNA-binding properties of pyrrolo[2,1-c][1,4]benzodiazephine N10-C11 amidines," *Eur. J Med. Chem.*, 31, 407-410 (1996).

Fujisawa Pharmaceutical Co., Ltd., "Benzodiazepine derivatives," SciFinder Scholar (2002) 2-3.

Fujisawa Pharmaceutical Co., Ltd., Abstract No. 139983k, "Benzodiazepine derivatives", *Chemical Abstracts*, vol. 99, No. 17, 603 (1983).

Fujisawa Pharmaceutical Co., Ltd., Abstract No. 72145x, "Benzodiazepine derivatives", *Chemical Abstracts*, vol. 98, No. 9, 638 (1983).

Fukuyama, T. et al., "Total Synthesis of (+)-Porothramycin B," *Tetrahedron Letters*, vol. 34, 16, 2577-2580 (1993).

Greene, T.W. et al., Protective Groups in Organic Synthesis, 3rd Edition (1999) John Wiley & Sons, Inc., pp. 23-200.

Greene, T.W. et al., Protective Groups in Organic Synthesis, John Wiley & Sons, 2nd Edition, Chapter 7 (1991) 315-345.

Greene, T.W. et al., Protective Groups in Organic Synthesis, John Wiley & Sons, Inc., 3rd Edition (1999) 503-549.

Gregson, S. et al., "Synthesis of a novel C2/C2'-exo unsaturated pyrrolobenzodiazepine cross-linking agent with remarkable DNA binding affinity and cytotoxicity," *Chemical Communications*, 797-798 (1999).

Gregson, S.J. et al., "Effect of C2/C3-endo unsaturation on the cytotoxicity and DNA-binding reactivity of pyrrolo-[2,1-c][1,4]-benzodiazepines," Bioorg. Med. Chem. Lett. (2000) 10(16):1849-1851.

Gregson, S.J. et al., "Linker length modulates DNA cross-linking reactivity and cytotoxic potency of C8/C8' ether-linked C2-exo-unsaturated pyrrolo[2,1-c][1,4]benzodiazepine (PBD) dimers," J. Med. Chem. (2004) 1161-1174.

Gregson, S.J. et al., "Synthesis of the first example of a C2-C3/C2'-C3'-endo unsaturated pyrrolo[2,1-c][1,4]benzodiazepine dimer," Biorg. Med. Chem. Lett. (2001) 11:2859-2862.

Gregson, S.J. et al., "Synthesis of the first examples of A-C8/C-C2 amide-linked pyrrolo[2,1-c][1,4]benzodiazepine dimers," Biorg. Med. Chem. Lett. (2003) 13:2277-2280.

Gregson, S.J. et al., "Design, Synthesis and Evaluation of a Novel Pyrrolobenzodiazepine DNA-Interactive Agent with Highly Efficient Cross-Linking Ability and Potent Cytotoxicity", *J Med. Chem.*, 44: 737-748 (2001).

Gregson, S.J. et al., "Effect of C2-*exo* Unsaturation on the Cytotoxicity and DNA-Binding Reactivity of Pyrrolo[2,1-c]1,4]benzodiazepines", *Bioorganic & Medicinal Chemistry Letters*, 10: 1845-1847 (2000).

Guiotto, A. et al., "Synthesis of novel C7-aryl substituted pyrrolo[2,1-c][1,4]benzodiazepines (PBDs) via Pro-N10-troc protection and suzuki coupling," *Bioorganic & Medicinal Chemistry Letters*, 8, No. 21, 3017-3018 (1998).

Hara et al., "DC 102, a new glycosidic pyrrolo(1,4)benzodiazepine antibiotic produced by *streptomyces* sp.", *J Antibiotics*, 41, 702-704 (1988).

Hochlowski, J. et al., "Abbeymycin, a new anthramycin-type antibiotic produced by a streptomycete," *J. Antibiotics*, 40, 145-148 (1987).

(56) References Cited

OTHER PUBLICATIONS

Howard, P.W. et al., "Synthesis of a novel C2/C2'-aryl-substituted pyrrolo[2,1-c][1,4]benzodiazepine dimer prodrug with improved water solubility and reduced DNA reaction rate," Biorg. Med. Chem. Lett (2009) 19:6463-6466.

Hurley, L. and Needham-Vandevanter, D., "Covalent Binding of Antitumor Antibiotics in the Minor Groove of DNA. Mechanism of Action of CC-1065 and the Pyrrolo(1,4)benzodiazepines," Acc. Chem. Res., 19, 230-237 (1986).

Itoh et al., "Sibanomicin, a new pyrrolo(1,4)benzodiazepine antitumor antibiotic produced by a *micromonospora* sp." *J. Antibiotics*, 41, 1281-1284 (1988).

Kamal et al., "Synthesis and DNA-binding affinity of A-C8/C-C2 alkoxyamido-linked pyrrolo[2,1-c][1,4]benzodiazepine dimers" Biorg. Med. Chem. Left. (2003) 13(22):3955-3958.

Kamal, A., et al., "An Efficient Synthesis of Pyrrolo[2,1-c][1,4] Benzodiazepine Antibiotics via Reductive Cyclization," *Bioorg. Med. Chem. Ltrs*, 7, No. 14, 1825-1828 (1997).

Kamal, A., et al., "Synthesis of Pyrrolo [2,1-c][1,4]-Benzodiazepene Antibiotics: Oxidation of Cyclic Secondary Amine with TPAP", *Tetrahedron*, v. 53, No. 9, 3223-3230 (1997).

Kamal, et al., "Synthesis of pyrrolo[2,1-c][1,4]benzodiazepines via reductive cyclization of w-azido carbonyl compounds by TMSI: an efficient preparation of antibiotic DC-81 and its dimers," Biorg. Med. Chem. Lett. (2000) 10:2311-2313.

Kaneko, T. et al., "Bicyclic and tricyclic analogues of anthramycin," J. Med. Chem. (1985) 28:388-392.

Kang, G.-D. et al., "Synthesis of a novel C2-aryl substituted 1,2-unsaturated pyrrolobenzodiazepine," Chem. Commun. (2003) 1688-1689.

Knapp, D.M. et al., "A general solution for unstable boronic acids: slow-release cross-coupling from air-stable MIDA boronates," J. Am. Chem. Soc. (2009) 131:6961-6963.

Kohn, K., "Anthramycin," *Antibiotics III*, Springer-Verlag, NY, 3-11 (1975).

Konishi, M. et al., "Chicamycin, a new antitumor antibiotic II. Structure determination of chicamycins A and B," *J Antibiotics*, 37, 200-206 (1984).

Kunimoto et al., "Mazethramycin, a new member of anthramycin group antibiotics," *J Antibiotics*, 33, 665-667 (1980).

Langley, D.R. and Thurston, D.E., "A versatile and efficient synthesis of carbinolamine-containing pyrrolo[1,4]benzodiazepines via the cyclization of N-92-aminobenzoyl)pyrrolidine-2-carboxaldehyde diethyl thioacetals: total synthesis of prothracarcin," *J. Org. Chem.*, 52, 91-97 (1987).

Langlois, N. et al., "Synthesis and cytotoxicity on sensitive and doxorubicin-resistant cell lines of new pyrrolo[2,1-c][1,4]benzodiazepines related to anthramycin," J. Med. Chem. (2001) 44:3754-3757.

Leber, J.D. et al., "A revised structure for sibiromycin," *J Am. Chem. Soc.*, 110, 2992-2993 (1988).

Leimgruber, W. et al., "Isolation and characterization of anthramycin, a new antitumor antibiotic," *J Am. Chem. Soc.*, 87, 5791-5793 (1965).

Leimgruber, W. et al., "The structure of anthramycin," *J Am. Chem. Soc.*, 87, 5793-5795 (1965).

Leimgruber, W. et al., "Total synthesis of anthramycin," *J Am. Chem. Soc.*, 90, 5641-5643 (1968).

Lown et al., "Molecular Mechanism of Binding of Pyrrolo(1,4)benzodiazepine antitumour agents to deoxyribonucleic acid—anthramycin and tomaymycin," Biochem. Pharmacol. (1979), 28 (13), 2017-2026.

Molander, G.A. et al., "Cross-coupling reactions of potassium alkyltrifluoroborates with aryl and 1-alkenyl trifluoromethanesulfonates," Org. Lett. (2001) 3(3):393-396.

Mori, M. et al., "Total syntheses of prothracarcin and tomaymycin by use of palladium catalyzed carbonylation," Tetrahedron (1986) 42(14):3793-3806.

Mountzouris, J.A. et al., "Comparison of a DSB-120 DNA interstrand cross-linked adduct with the corresponding bis-Tomaymycin adduct," J. Med. Chem. (1994) 37:3132-3140.

Mu, YQ., et al., "Coupling of isoprenoid triflates with organoboron nucleophiles: synthesis of all-trans-geranylgeraniol," Tetrahedron Lett. (1995) 36(32):5669-5672.

Nagasaka, T. and Koseki, Y, "Stereoselective Synthesis of Tilivalline," *Journal of Organic Chemistry*, vol. 63, No. 20, 6797-6801 (1998).

Nagasaka, T. et al., "Stereoselective Synthesis of Tilivalline," *Tetrahedron Letters*, 30:14, 1871-1872 (1989).

Nishihara, Y. et al., "Coupling reactions of alkynylsilanes mediated by a Cu(I) salt: novel syntheses of conjugate diynes and disubstituted ethynes," J. Org. Chem. (2000) 65:1780-1787.

Oh-E, T. et al., "Palladium-catalyzed cross-coupling reaction of aryl or vinylic triflates with organoboron compounds," SynLett (1990) 221-223.

Oh-E, T. et al., "Palladium-catalyzed cross-coupling reaction of organoboron compounds with organic triflates," J. Org. Chem. (1993) 58:2201-2208.

O'Neil, Chemical Abstract No. 171573p, "The synthesis of Functionalized Pyrrolo-[2,1-c][1,4]-Benzodiazepines", *Chemical Abstracts*, vol. 126, No. 13, 618 (1997).

O'Neil, I.A., et al., "The Synthesis of Functionalized Pyrrolo-[2,1-c][1,4]-Benzodiazepines," *Synlett*, 75-78 (1997).

O'Neil, I.A. et al., "DPPE: A Convenient Replacement for Triphenylphosphine in the Staudinger and Mitsunobu Reactions", *Tetrahedron Letters*, vol. 39, No. 42, 7787-7790 (1998).

Perez, I. et al., "Palladium-catalyzed cross-coupling reactions of triorganoindium compounds with vinyl and aryl triflates or iodides," Org. Lett. (1999) 1(8):1267-1269.

Sagnou, M.J. et al., "Design and Synthesis of Novel Pyrrolobenzodiazepine (PDB) Prodrugs for ADEPT and GDEPT," *Bioorganic & Medicinal Chemistry Letters*, 10, 2083-2086 (2000).

Shimizu, K et al., "Prothracarcin, a Novel Antitumor Antibiotic," *J Antibiotics*, 35, 972-978 (1982).

Smellie, M. et al., "Cellular pharmacology of novel C8-linked anthramycin-based sequence-selective DNA minor groove cross-linking agents," Br. J. Cancer (1994) 70:48-53.

Smellie, M. et al., "Sequence selective recognition of duplex DNA through covalent interstrand cross-linking," Biochem. (2003) 42:8232-8239.

Suggs, J.W. et al., "Synthesis and structure of anthramycin analogs via hydride reduction of dilactams," *Tetrahedron Letters*, 26, No. 40, 4871-4874 (1985).

Takeuchi, T. et al., "Neothramycins A and B, New Antitumor Antibiotics," *J Antibiotics*, 29, 93-96 (1976).

Tercel, M. et al., "Unsymmetrical DNA cross-linking agents: combination of the CBI and PBD pharmacophores," J. Med. Chem. (2003) 46:2132-2151.

Thurston, D. E., "Advances in the study of Pyrrolo[2,1-c][1,4] benzodiazepine (PBD) Antitumour Antibiotics", *Molecular Aspects of Anticancer Drug-DNA Interaction*, Neidle, S. and Waring, M.J., Eds.; Macmillan Press Ltd, 1:54-88 (1993).

Thurston, D.E. and Bose, D.S., "Synthesis of DNA-Interactive Pyrrolo[2,1-c][1,4]benzodiazepines," Chem. Rev., 94:433-465 (1994).

Thurston, D.E. and Thompson, A.S., "The molecular recognition of DNA," Chem. Brit., 26, 767-772 (1990).

Thurston, D.E. et al., "Effect of A-ring modifications on the DNA-binding behavior and cytotoxicity of pyrrolo[2,1-c][1,4]benzodiazepines", *Journal of Medicinal Chemistry*, 42:1951-1964 (1999).

Thurston, D.E. et al., "Synthesis of Sequence-selective C8-linked Pyrrolo [2,1-c][1,4] Benzodiazepine DNA Interstrand Cross-linking Agent," *J. Org. Chem.*, 61:8141-8147 (1996).

Thurston, D.E. et al., "Synthesis of a novel GC-specific covalent-binding DNA affinity-cleavage agent based on pyrrolobenzodiazepines (PBDs)," Chemical Communications, 563-565 (1996).

Thurston, D.E., "Nucleic acid targeting: therapeutic strategies for the 21st century," Brit. J. Cancer (1999) 80(1):65-85.

Tiberghien, A.C. et al., "Application of the stille coupling reaction to the synthesis of C2-substituted endo-exo unsaturated pyrrolo[2,1-c][1,4]benzodiazepines (PBDs)," Biorg. Med. Chem. Lett. (2004) 14:5041-5044.

(56) References Cited

OTHER PUBLICATIONS

Tsunakawa, M. et al., "Porothramycin, a new antibiotic of the anthramycin group: Production, isolation, structure and biological activity," *J. Antibiotics*, 41:1366-1373 (1988).

Umezawa, H. et al., Chemical Abstract No. 4427a, "Mazethramycins" *Chemical Abstracts*, vol. 90, No. 1, 428 (1979).

Umezawa, H. et al., "Mazethramycins," SciFinder Scholar (2002) 2-3.

Wilson, S.C. et al., "Design and Synthesis of a Novel Epoxide-Containing Pyrrolo[2,1-c][1,4]benzodiazepine (PBD) via a New Cyclization Procedure," *Tetrahedron Letters*, 36, No. 35, 6333-6336 (1995).

Wilson, S.C. et al., "Design, Synthesis, and Evaluation of a Novel Sequence-Selective Epoxide-Containing DNA Cross-Linking Agent Based on the Pyrrolo[2,1-c][1,4]benzodiazepine System", *J. Med. Chem*. 42:4028-4041 (1999).

Yao, M-L. et al., "Facile approach to 4-substituted 2(5H)-furanones," J. Org. Chem. (2000) 65:5034-5036.

Dubowchik et al., "Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity" Bioconjugate Chem. (2002) 13, 855-869.

United Stated Patent Office Action for U.S. Appl. No. 13/641,237 dated Jan. 16, 2014 (5 pages).

United Stated Patent Office Notice of Allowance for U.S. Appl. No. 13/641,237 dated Apr. 25, 2014 (5 pages).

\* cited by examiner

SYNTHESIS METHOD AND INTERMEDIATES USEFUL IN THE PREPARATION OF PYRROLOBENZODIAZEPINES

CROSS-REFERENCE TO RELATED APPLICATIONS

This application is a national stage filing under 35 U.S.C. 371 of International Application No. PCT/EP2012/070232 filed Oct. 12, 2012, and claims the benefit of U.S. Provisional Application No. 61/547,207 filed Oct. 14, 2011, which is incorporated by reference herein.

The present invention relates to methods useful in the synthesis of pyrrolobenzodiazepines (PBDs), and in particular of pyrrolobenzodiazepines having C2 substitution and N10 protection.

BACKGROUND TO THE INVENTION

PBDs are of the general structure:

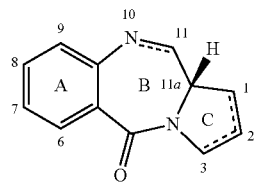

C2-substituted Compounds

In WO 2004/043963, a diverse range cytotoxic compounds having an aryl group at the C2 position, for example:

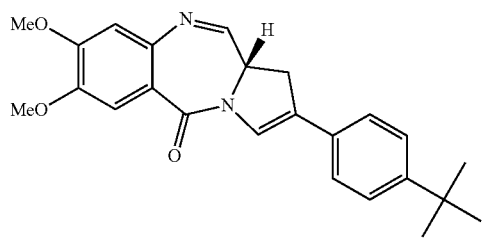 [SMILES: COc1cc2c(cc1OC)C(=O)N1C=C(c3ccc(C(C)(C)C)cc3)C[C@H]1C=N2]

were disclosed. The synthesis of these compounds was achieved via the following intermediate:

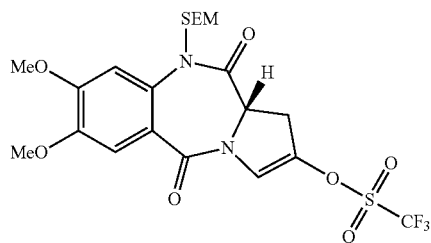 [SMILES: COc1cc2c(cc1OC)N(COCC[Si](C)(C)C)C(=O)[C@@H]1CC(OS(=O)(=O)C(F)(F)F)=CN1C2=O]

whose synthesis was described in detail in WO 00/12508. An analagous dimeric intermediate is disclosed in WO 2010/010347.

WO 2005/085251 discloses the synthesis of a number cytotoxic compounds having an aromatic substituent or unsaturated substituent at C2 from the intermediate:

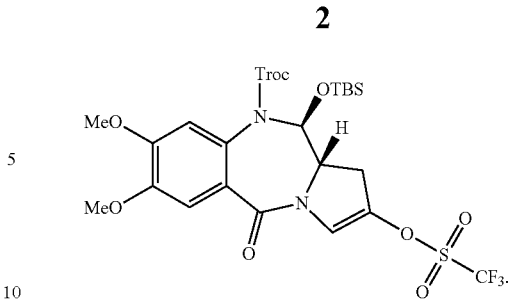

These intermediates are very useful for synthesis C2 substituted PBD compounds having a N10-C11 imine bond, or compounds readily derivable from these, e.g. bisulphite versions, as in WO 2010/010347. The N10 protecting groups used are not labile under the conditions used to add the C2 aryl substituents, for example, in a Suzuki coupling using a palladium catalyst.

The C2-aryl or unsaturated group is installed by forming a C2-enol triflate followed by a palladium catalyzed Suzuki reaction. It is advantageous to add the C2 aryl or unsaturated substituents as late as possible in the synthesis by the methods described above, as this means a diverse range of substituents can be added to a single 'core'.

However, there are compounds of interest where the protecting groups or linkers desired at N10 are labile under either the triflation conditions (e.g. substituted p-aminobenzyl or p-hydroxybenzyl carbamates) or palladium catalysis (e.g. Alloc), see below.

Such groups are preferably introduced at a point in the synthesis of the PBD before the B-ring is formed by cyclisation. Otherwise, these groups would need to be added via a chloroformate to the PBD's imine bond. In addition, the cyclisation of PBD is best carried out where the pro-N10 nitrogen has only a single hydrogen attached, i.e., where the protecting group is already in place.

WO 2005/085259 discloses PBD compounds useful as intermediates in the synthesis of PBD dimers. These intermediates have a hydroxy group at the C7 or C8 position.

DISCLOSURE OF THE INVENTION

The present inventors have developed a key intermediate for the production of C2 substituted PBDs having a palladium sensitive N10 protecting group, and a method for its synthesis.

In a first aspect, the present invention comprises a compound of formula I:

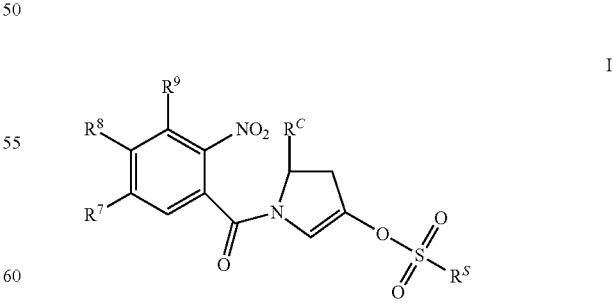

wherein:
$R^7$ is selected from: $OR^A$, where $R^A$ is selected from $C_{1-4}$ saturated alkyl, optionally substituted by phenyl, which phenyl may bear a chloro substituent, pyridyl and furanyl; chloro; $NH_2$; and $-CH_2-O-C(=O)Me$;

$R^8$ is $OProt^O$, where $Prot^O$ is a silicon-based oxygen protecting group orthogonal to $R^C$;
$R^9$ is selected from H, methyl and methoxy;
$R^S$ is selected from $CF_3$, $(CF_2)_3CF_3$, $CH_3$ and

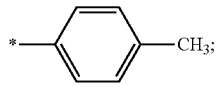 [SMILES: *c1ccc(C)cc1]

and
$R^C$ is selected from:
(i) —C(=O)—$OR^{C1}$, where $R^{C1}$ is a saturated $C_{1-4}$ alkyl group;
(ii) $CH_2$—O—C(=O)$R^{C2}$, where $R^{C2}$ is methyl or phenyl;
(iii) $CH_2$—O—Si—$(R^{Si1})(R^{Si2})(R^{Si3})$, where $R^{Si1}$, $R^{Si2}$, $R^{Si3}$ are independently selected from a $C_{1-6}$ saturated alkyl group and a phenyl group; and
(iv) $C(-YR^{C3})(-YR^{C4})$ where each Y is independently O or S, and where $R^{C3}$ and $R^{C4}$ are independently a saturated $C_{1-4}$ alkyl group, or together form a $C_{2-3}$ alkylene.

The compound of formula I is preferably substantially free of any of the corresponding compound of formula IB:

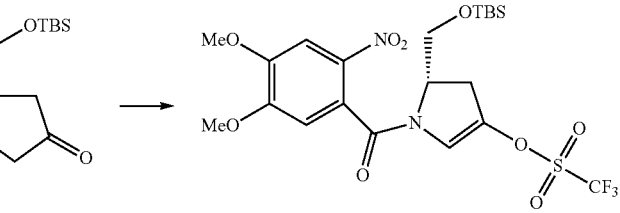

wherein $R^7$, $R^8$, $R^9$ and $R^C$ are as defined in the compound of formula I. "Substantially free" means that there is less than 5% by weight of the compound of formula IB compared to the amount of the compounds of formula I. More preferably, there is less than 1% or 0.1% by weight of the compound of formula IB.

In a second aspect, the present invention provides a method of synthesising a compound of formula I as defined in the first aspect of the invention from a compound of formula II:

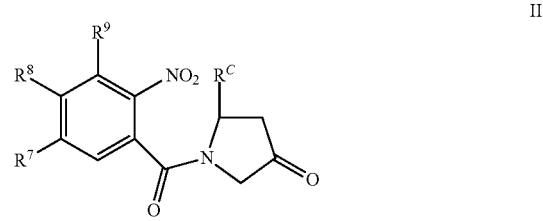

wherein $R^7$, $R^8$, $R^9$ and $R^C$ are as defined in the first aspect;

comprising treating II with the appropriate anhydride and anhydrous 2,6-lutidine or anhydrous 2,6-$^t$Bu-pyridine at a temperature of –35° C. or lower in a dry organic solvent under an inert atmosphere.

The following reaction has been previously disclosed (Kang, G-D., et al., Chem. Commun., 2003, 1680-1689):

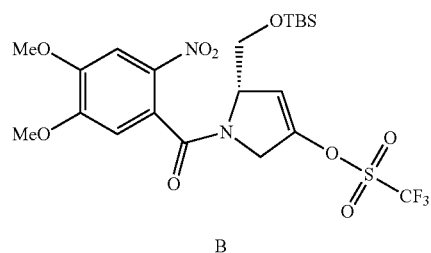

This reaction was carried out using (trifluoromethanesulfonyl)aminopyridine at −78° C., which followed treatment with either LDA (lithium diethylamide) or NaHMDS (sodium hexamethyldisilazide). The method involving LDA gave a mixture of A to B in the ratio 1:4, whilst the NHDMS method gave only B.

Compounds of formula I can be converted into N10 protected PBD compounds by the following steps.

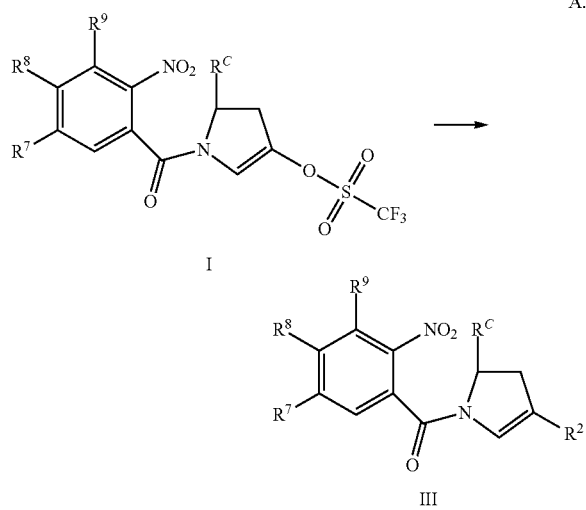

where $R^2$ is selected from:
(i) an optionally substituted $C_{5-20}$ aryl group;
(ii) an optionally substituted $C_{1-5}$ alkyl group (including a $C_{2-5}$ alkenyl group and a $C_{2-5}$ alkynyl group); and
(iii) H.

These conversions are carried using palladium catalysis, and include: Suzuki couplings with an appropriate boron derivative; Heck coupling with alkenes, including acrylamides and acrylates; Stille couplings with organo tin reagents, such as alkyl tin reagents; Sonagishira couplings with alkynes; and hydride transfer using triethyl silanes.

The conversion where $R^2$ is an optionally substituted $C_{5-20}$ aryl group (a Suzuki coupling) is carried out by palladium catalysed cross coupling of I with the appropriate aryl boron derivative. The palladium catalyst may be any suitable catalyst, for example $Pd(PPh_3)_4$, $Pd(OCOCH_3)_2$, $PdCl_2$, or $Pd(dba)_3$.

Suzuki couplings may also be used to cross couple alkyl boron species. The Gibbs group has reported (Mu, Y. Q and Gibbs, R. A, *Tetrahedron Letters*, 36, 5669-5672, 1995) the successful conversion of an enol triflate to a methyl substituted alkene (using a $Pd(PHCN)_2Cl_2$ catalyst):

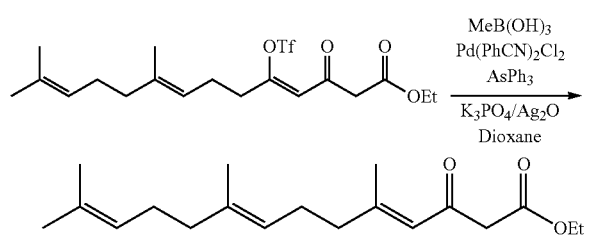

Deng's group successfully achieved the coupling of a cyclopropylboronic acid and a cyclic triflate using a Pd $(MeCN)_2Cl_2$ catalyst (Yao and Deng, *J. Org. Chem.* 2000, 65, 1609).

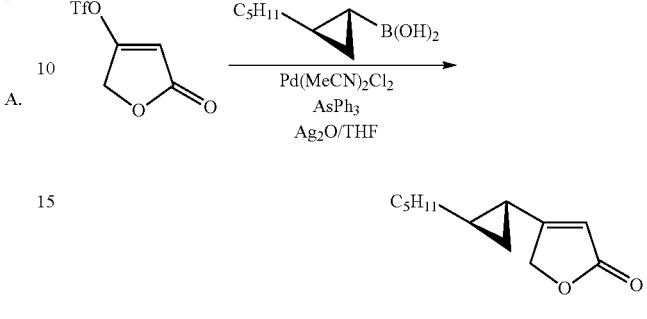

Cyclopropyl MIDA boronates have been successfully coupled to aryl chlorides under slow release conditions; intact MIDA boronates are resistant to standards Suzuki conditions due to their pyramidal hybridization (Knapp et al. *J. Am. Chem. Soc.*, 2009, 131, 6961-6963). These conditions are also be applicable to enoltriflates.

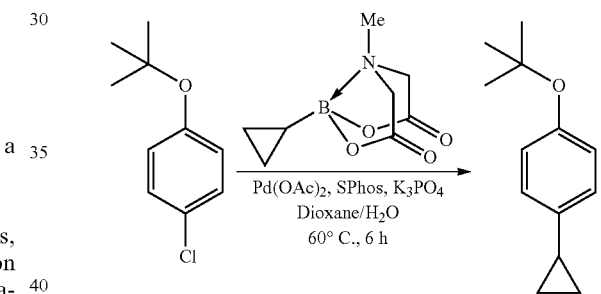

Knapp et al. *J. Am. Chem. Soc.*, 2009, 131, 6961-6963

Molander (Molander and Ito *Org. Lett.*, 2001, 3, 393-396) has developed potassium alkyltrifluoroborates as Suzuki coupling partners for aryl and vinyl triflates.

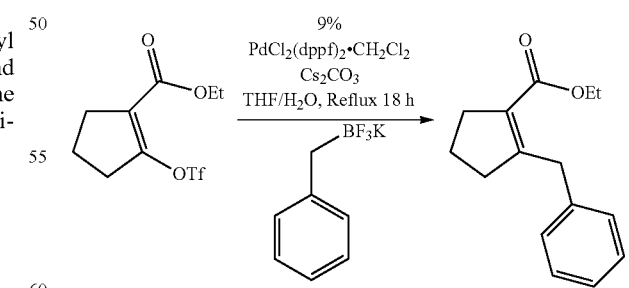

Suzuki couplings may also be used to cross couple alkenyl boron species. Suzuki and co workers have demonstrated (Suzuki et al., Synlett 1990, 221; *J Org Chem* 1993, 58, 2201) the coupling of cyclic triflates and benzodioxoleborole compounds

7

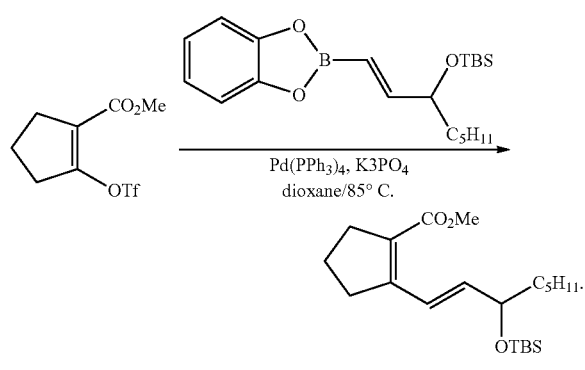

Alkenyl Boronic acids have also been coupled to PBD C-ring enoltriflates (WO2005/085251):

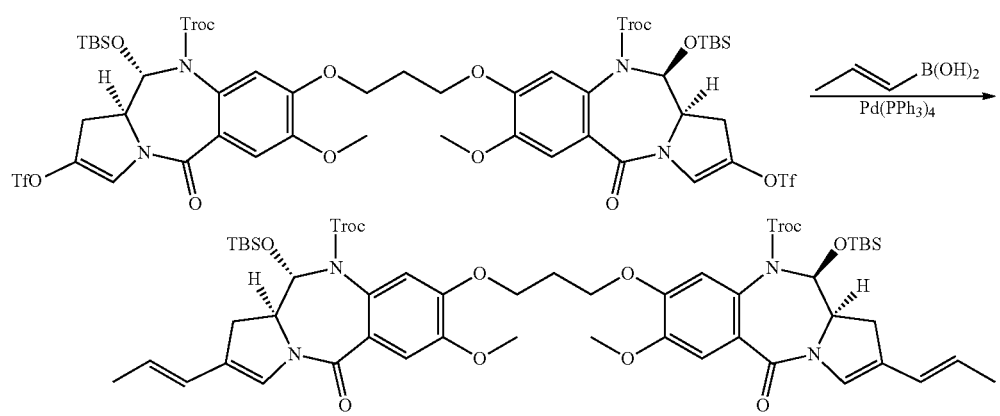

The pinacol esters of acrylylboronic acids are known:

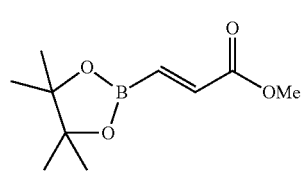

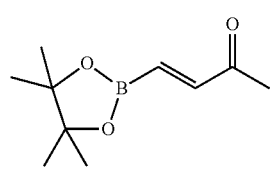

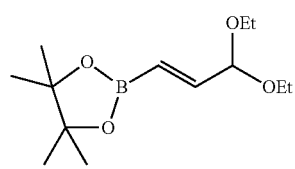

and are likely to be useful in Suzuki coupling reactions.

8

PBD enol triflates have been successfully coupled to acrylamides and acrylates under Heck conditions (Chen et al., *Bioorg. Med. Chem. Lett.* 14, (2004), 1547-1549):

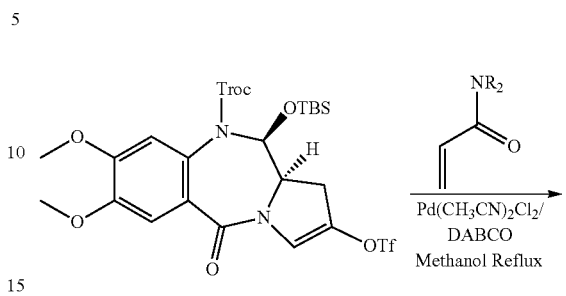

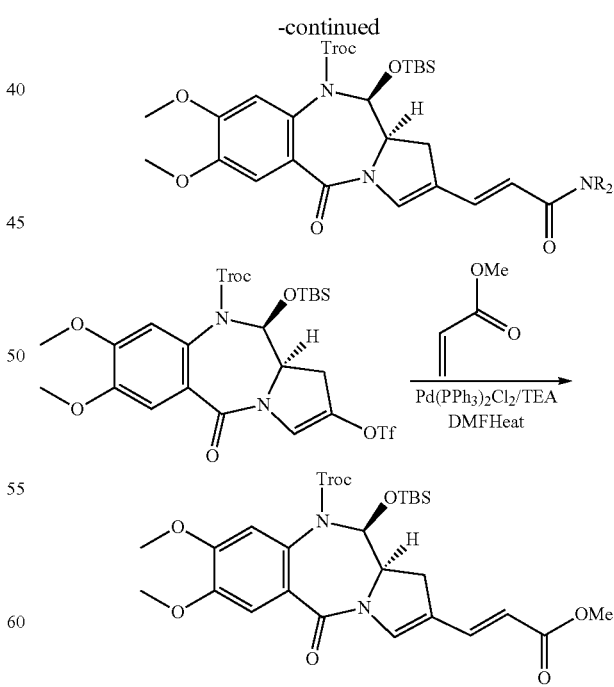

Alkynyl tin reagents have been coupled under Stille conditions to PBD triflates (Tiberghien et al., *Bioorg. Med. Chem. Lett.* 14, (2004), 5041-5044):

Alkynyl substituents can also be installed via the Sonogishira reaction (Nishihara et al *J. Org. Chem.*, 2000, 65, 1780-1787):

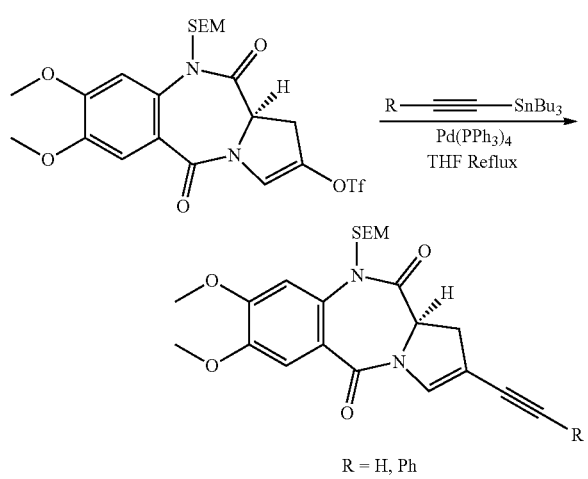

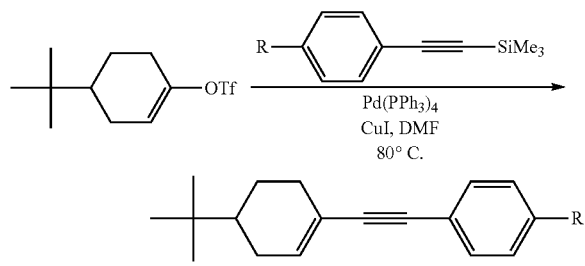

Other palladium catalysed reactions include the use triakylindium reagents in cross-coupling reactions (Perez et al. *Org. Lett*, 1999, 1, 1267-1269):

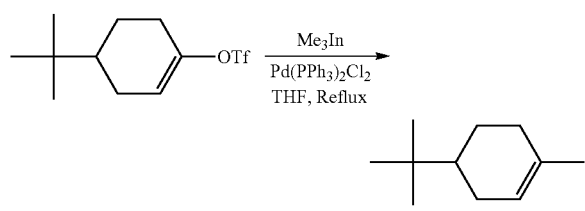

The approach can also be used to introduce aryl, vinyl and alkynyl groups.

Palladium catalysis can also be used in hydride transfer reactions to generate alkenes with triethylsilanes (Cramer et al. *Angew. Chem. Int. Ed.* 2005, 44, 820-822):

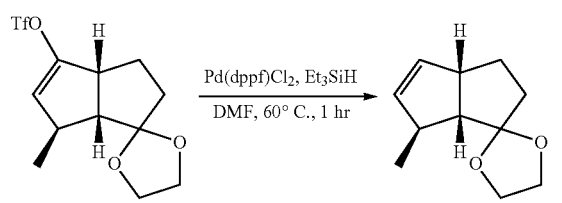

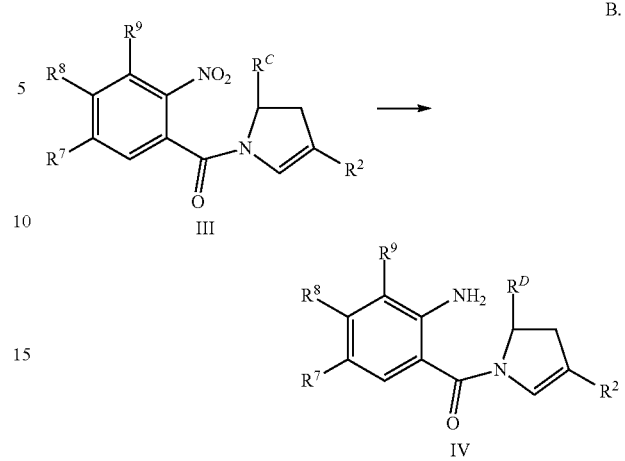

where $R^D$ is selected from:
(ii) $CH_2$—O—C(=O)$R^{C2}$, where $R^{C2}$ is methyl or phenyl;
(iii) $CH_2$—O—Si—($R^{Si1}$)($R^{Si2}$)($R^{Si3}$), where $R^{Si1}$, $R^{Si2}$, $R^{Si3}$ are independently selected from a $C_{1-6}$ saturated alkyl group and a phenyl group; and
(iv) C(—Y$R^{C3}$)(—Y$R^{C4}$) where each Y is independently O or S, and where $R^{C3}$ and $R^{C4}$ are independently a saturated $C_{1-4}$ alkyl group, or together form a $C_{2-3}$ alkylene,
and $R^D$ is orthogonal to Prot$^O$.

If $R^C$ is —$CH_2$—O—C(=O)$R^{C2}$ or —$CH_2$—O—Si—($R^{Si1}$)($R^{Si2}$)($R^{Si3}$) then the conversion of III to IV is by reduction of the nitro group.

If $R^C$ is —C(=O)—O$R^{C1}$, then the conversion of III to IV is achieved by first reducing of the ester and reprotection as an acetate or silyl ether. The reduction can be achieved by standard means, for example with $LiAlH_4$, $LiBH_4$ or $NaBH_4$, but preferably $LiBH_4$. Reprotection as an acetate can be achieved, for example, by reaction with acetyl chloride; reprotection as a benzoate can be achieved, for example, by reaction with benzoyl chloride; reprotection as a silyl ether can be achieved, for example, by reaction with the appropriate silyl chloride. The reduction of the nitro group is then carried out as described above.

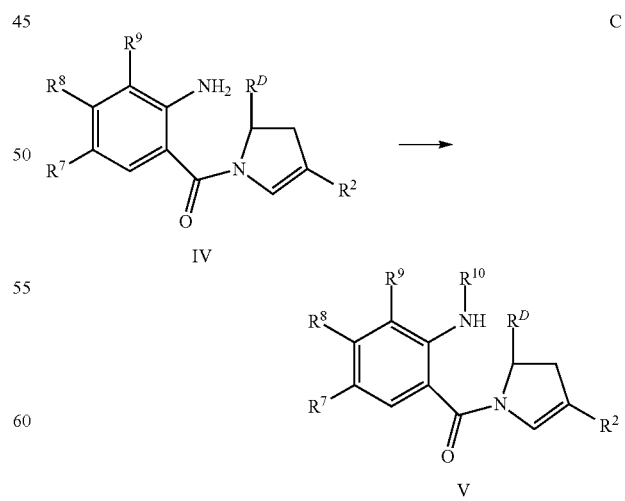

where $R^{10}$ is a carbamate-based nitrogen protecting group, which is palladium-labile and/or labile under the conditions used to add the group:

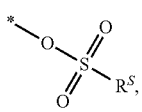

or contains a moiety which is palladium-labile and/or is labile under the conditions used to add the group:

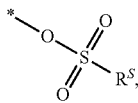

i.e. liable to be removed in the presence of palladium or under the conditions used to add the group:

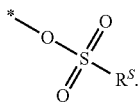

In this application these protecting groups are classified as 'simple' and 'complex'.

Conversion of IV to V is usually achieved by reaction of IV with triphosgene to obtain the isocyanate followed by reaction with $R^{10}$—OH. This approach is described in WO 2005/023814.

Alternatively, simple nitrogen protecting groups can also be introduced as a chloroformate, fluoroformate or azidoformate. The more complex nitrogen protecting groups, as well as the simple nitrogen protecting groups, can be introduced as O-succinamide carbonates, O-pentafluorophenyl carbonates and O-nitrophenyl carbonates.

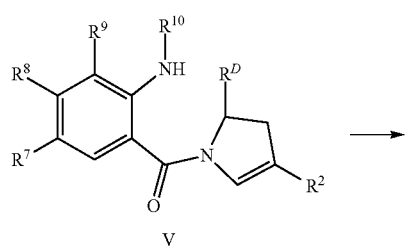

When $R^P$ is —$CH_2$—O—C(=O)Me, the conversion of V to VI may be achieved by initial removal of the acetate protecting group, with potassium carbonate in aqueous methanol, or with lithium triethylborohydride. Oxidation with Dess-Martin periodinane (or alternatively TPAP/NMO, TFAA/DMSO, $SO_3$. Pyridine complex/DMSO, PDC, PCC, BAIB/TEMPO or under Swern conditions) affords the ring closed product.

When $R^P$ is —$CH_2$—O—C(=O)Ph, the conversion of V to VI may be achieved by initial removal of the benzoate protecting group, with sodium hydroxide in aqueous methanol, followed by oxidation as described above.

When $R^P$ is —$CH_2$—O—Si—($R^{Si1}$)($R^{Si2}$)($R^{Si3}$), the conversion of V to VI may be achieved by initial removal of the silyl ether protecting group, for example using TBAF in THF, acetic acid in aqueous THF, CsF in DMF or HF in pyridine, followed by oxidation as described above. The removal conditions must be selected such that they do not remove $Prot^O$.

When $R^P$ is —C(—$YR^{C3}$)(—$YR^{C4}$), the conversion of V to VI may be achieved by removal of the acetal or thioacetal protecting groups, respectively with acid or reaction with Hg(II) salts—the cyclisation occurs spontaneously

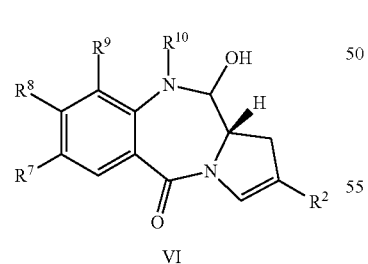

wherein $R^E$ is selected from: O—$C_{1-2}$ alkyl; O—Si—($R^{Si1}$)($R^{Si2}$)($R^{Si3}$) where $R^{Si1}$, $R^{Si2}$, $R^{Si3}$ are as defined above; O—$CH_2OCH_3$ (OMOM), O—$CH_2OC_2H_4OCH_3$ (OMEM), $OC_5H_{10}$, (THP). $Prot^O$ needs to be orthogonal to $R^E$, and therefore $R^E$ needs to be selected with this in mind. In some embodiments, $R^E$ may also be OC(=O)Me.

OH is converted to $R^E$ by conventional methods. For example, when $R^E$ is O—$C_{1-2}$ alkyl, the conversion may be carried out by reaction with $C_{1-2}$ alkyl-I and silver oxide or ($C_{1-2}$ alkyl)$_3O^+BF_4^-$ in DCM in the presence of DIPEA. When $R^E$ is OMOM or OMEM, the conversion may be carried out by reaction with the appropriate chloride in DCM in the presence of DIPEA. When $R^E$ is THP, the conversion may be carried out by reaction with DHP in the presence of acid. When $R^E$ is O—Si—($R^{Si1}$)($R^{Si2}$)($R^{Si3}$), the conversion may be carried out by reaction with the appropriate triflate in the presence of 2,6-lutidine.

-continued

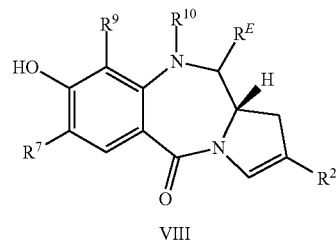

VIII

Deprotection of the phenolic hydroxy group is carried out by, for example, lithium acetate. The removal conditions must be selected such that they do not remove $R^E$.

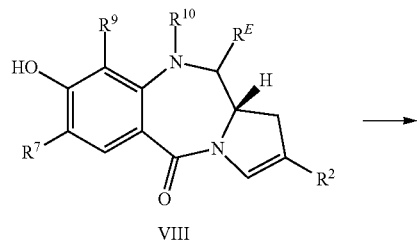

VIII

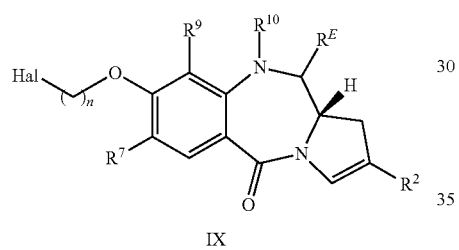

IX where Hal is selected from I, Cl and Br, and n is from 1 to 12.

The conversion of VIII to IX is achieved by reaction with a compound of formula X:

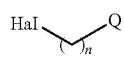

where Q is selected from I, Cl and Br. The reaction is carried out, for example, in refluxing acetone with a base, such as $K_2CO_3$. An excess of the compound of formula X is required to achieve the desired product.

H: The present invention also provides a method of linking compounds of formulae VIII and IX, to yield a compound of formula XI:

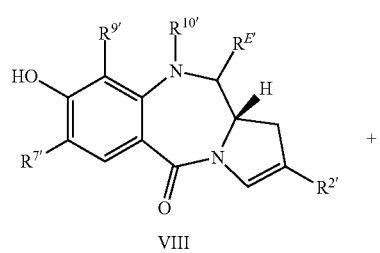

VIII

+

-continued

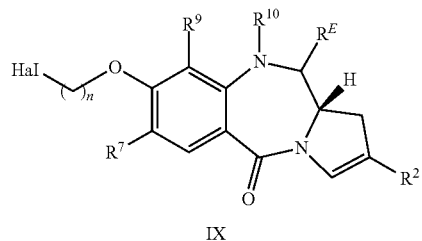

IX

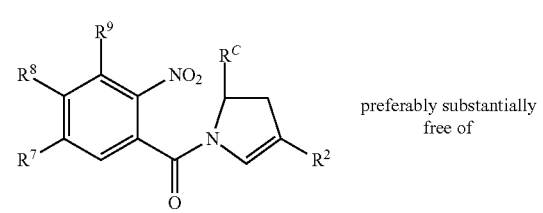

XI where $R^{2'}$, $R^{7'}$, $R^{9'}$, $R^{10'}$ and $R^{E'}$ are independently selected from the same groups as $R^2$, $R^7$, $R^9$, $R^{10}$ and $R^E$ respectively. The reaction is carried out, for example, in refluxing acetone with a base, such as $K_2CO_3$.

The present invention also provides:

(a) a compound of formula III:

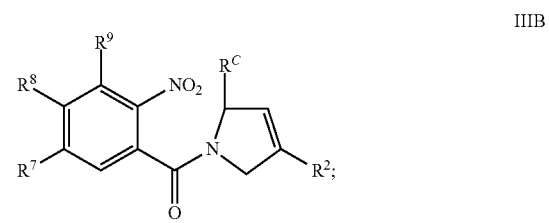

III preferably substantially free of

IIIB (b) a compound of formula IV:

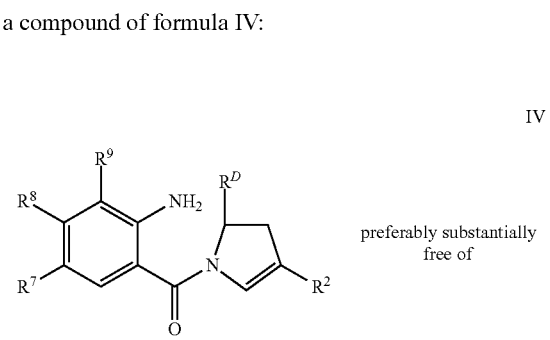

IV preferably substantially free of

-continued (c) a compound of formula V:

(d) a compound of formula VI:

(e) a compound of formula VII:

preferably substantially free of (f) a compound of formula VIII:

preferably substantially free of and
(g) a compound of formula IX:

preferably substantially free of

The term 'substantially free of' means that there is less than 5% by weight of the compound of the undesired compound (i.e., B version) compared to the amount of the desired compound. More preferably, there is less than 1% or 0.1% by weight.

The present invention also provides
(a) a method of making a compound of formula VIII, comprising the step of making a compound of formula I from a compound of formula II;
(b) a method of making a compound of formula IX, comprising the step of making a compound of formula I from a compound of formula II;
(c) a method of making a compound of formula X, comprising the step of making a compound of formula I from a compound of formula II.

In the above further aspects of the present invention, the defined substituent groups in the intermediate compounds are the same as those in the final products where designated in the same way (e.g. $R^9$ remains the same throughout the method of synthesis).

In the above further aspects of the invention, the methods may also comprise the intermediate steps as set out above.

Definitions

Silicon-Based Oxygen Protecting Groups

Silican-based oxygen protecting groups are well known in the art. A large number of suitable groups are described on pages 113 to 148 of Greene, T. W. and Wuts, G. M., Protective Groups in Organic Synthesis, $3^{rd}$ Edition, John Wiley & Sons, Inc., 1999, which is incorporated herein by reference.

The groups form silyl ethers with the oxygen to which they are attached, and are generally of the formula:

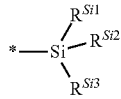

where $R^{Si1}$, $R^{Si2}$ and $R^{Si3}$ are independently selected from a $C_{1-6}$ saturated alkyl group and a phenyl group. Examples are:

| TMS | —SiMe₃ | TBDMS | —SiMe(t-Bu)₂ |
|---|---|---|---|
| TES | —SiEt₃ | TBDPS | —SiPh₂t-Bu |
| TIPS | —Si(i-Pr)₃ | TPS | —SiPh₃ |
| IPDMS | —SiMe₂i-Pr | DPMS | —SiMePh₂ |
| DEIPS | —SiEt₂(i-Pr) | DTBMS | —SiMe(t-Bu)₂ |
| TDS | —SiMe₂C(CH₃)₂CH(CH₃)₂ | | |

Orthogonal

A first protecting group which is orthogonal to a second protecting group means that the first protecting group can be removed from a compound bearing both protecting groups without the second protecting group being removed.

As discussed above, $R^D$ is orthogonal to $Prot^O$, and $Prot^O$ is orthogonal to $R^E$.

Carbamate-Based Nitrogen Protecting Groups

Carbamate-based nitrogen protecting groups are well known in the art. A large number of suitable groups are described on pages 503 to 549 of Greene, T. W. and Wuts, G. M., Protective Groups in Organic Synthesis, $3^{rd}$ Edition, John Wiley & Sons, Inc., 1999, which is incorporated herein by reference.

The carbamate-based nitrogen protecting groups used may be those which are sensitive to palladium or sensitive to the conditions needed to add the group:

Table 1 provides examples of some such groups ('simple nitrogen protecting groups'):

TABLE 1

| DBD-Tmoc | 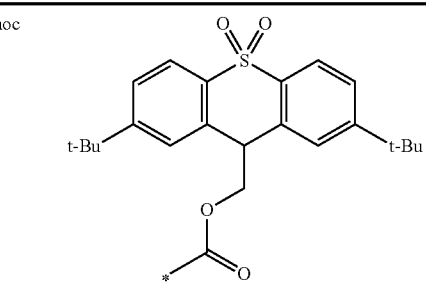 | Cbz (benzyl carbamate) | 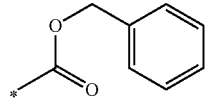 |
|---|---|---|---|
| Voc (Vinyl carbamate) | 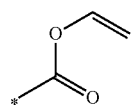 | 1,1-dimethylpropynyl carbamate | 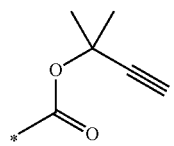 |
| Alloc (Allyl carbamate) | 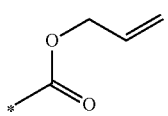 | Moz (p-methoxybenzylcarbamate) | 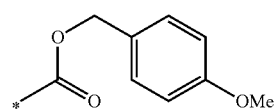 |

TABLE 1-continued

| | | | |
|---|---|---|---|
| Ipaoc (1-isopropylallyl carbamate) | 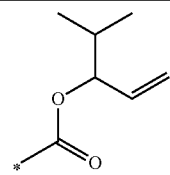 | PNZ (p-nitrobenzylcarbamate) | 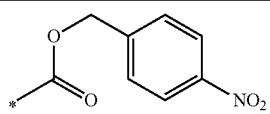 |
| Coc (Cinnamyl carbamate) | 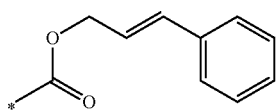 | 3,4-dimethoxy-6-nitrobenzyl carbamate | 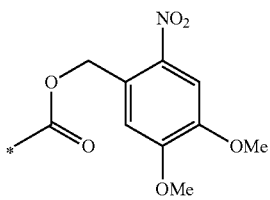 [SMILES: COc1cc(COC(C)=O)c([N+](=O)[O-])cc1OC] |
| Noc (4-nitrocinnamyl carbamate) | 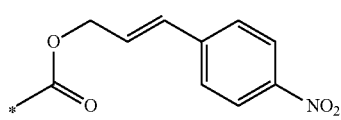 [SMILES: CC(=O)OC/C=C/c1ccc([N+](=O)[O-])cc1] | p-bromobenzyl carbamate | 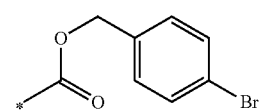 |
| Paloc (3-(3'-pyridyl)prop-2-enyl carbamate) | 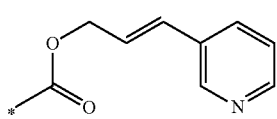 | p-chlorobenzyl carbamate | 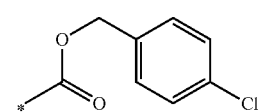 |
| N-hydroxypiperidinyl carbamate | 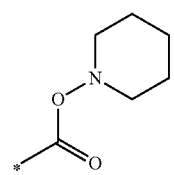 | 2,4-dichlorobenzyl carbamate | 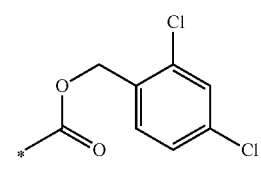 |
| 1,1-dimethyl-2-bromoethyl carbamate | 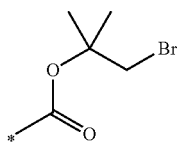 | Bic (5-benzylisoxazolylmethyl) | 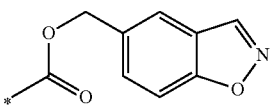 |
| 1,1-dimethyl-2-chloroethyl carbamate | 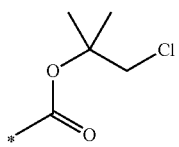 | Diphenylmethyl carbamate | 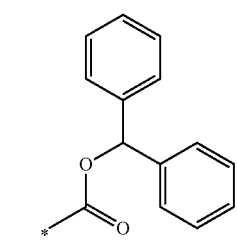 |
| 1,1-dimethyl-2-cyanoethyl carbamate | 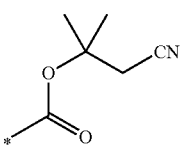 | 9-anthrylmethyl carbamate | 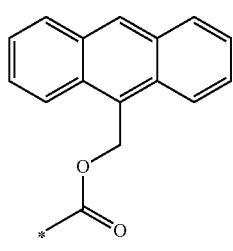 |
| Propynyl carbamate | 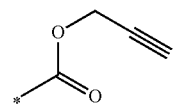 | S-benzyl carbamate | 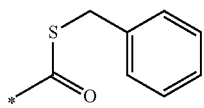 | where the asterisk indicates the point of attachment to the N10 position.

where the asterisk indicates the point of attachment to the N10 position.

In some embodiments of the present invention, the carbamate nitrogen protecting group is not Cbz (benzyl carbamate), PNZ (p-nitrobenzylcarbamate), or 3,4-dimethoxy-6-nitrobenzyl carbamate.

Also suitable for use in the present invention are carbamate-based nitrogen protecting groups having a complex architecture (complex nitrogen protecting groups'). These groups may be or may comprise elements of the groups described, for example, in WO 00/12507. These carbamate-based nitrogen protecting groups may include elements that are sensitive to palladium or the conditions used to add the group:

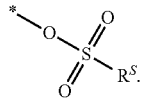

These elements may be any one of the structures listed in Table 1 above.

In one embodiment, the carbamate-based nitrogen protecting group is a linker for connection to an antibody, $R^L$:

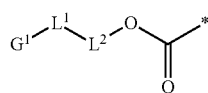

where the asterisk indicates the point of attachment to the N10 position, $G^1$ is a functional group to form a connection to a cell binding agent, $L^1$ is a cleavable linker, $L^2$ is a covalent bond or together with —OC(=O)— forms a self-immolative linker.

In one embodiment, the protecting group $R^L$ is removable from the N10 position thereby to provide the imine or carbinoalmine form of the PBD.

$L^1$ is preferably a cleavable linker, and may be referred to as a trigger for activation of the linker for cleavage.

The nature of $L^1$ and $L^2$, where present, can vary widely. These groups are chosen on the basis of their cleavage characteristics, which may be dictated by the conditions at the site to which the PBD molecule is delivered, for example as an antibody drug conjugate. Those linkers that are cleaved by the action of enzymes are preferred, although linkers that are cleavable by changes in pH (e.g. acid or base labile), temperature or upon irradiation (e.g. photolabile) may also be used. Linkers that are cleavable under reducing or oxidising conditions may also find use in the present invention.

$L^1$ may comprise a contiguous sequence of amino acids. The amino acid sequence may be the target substrate for enzymatic cleavage, thereby allowing release of $R^{10}$ from the N10 position.

In one embodiment, the $L^1$ is cleavable by the action of an enzyme. In one embodiment, the enzyme is an esterase or a peptidase.

In one embodiment, $L^2$ is present and together with C(=O)O forms a self-immolative linker.

In one embodiment, where $L^1$ is cleavable by the action of an enzyme and $L^2$ is present, the enzyme cleaves the bond between $L^1$ and $L^2$.

$L^1$ and $L^2$ may be connected by a bond selected from:
—C(=O)NH—,
—C(=O)O—,
—NHC(=O)—,
—OC(=O)—,
—OC(=O)O—,
—NHC(=O)O—,
—OC(=O)NH—, and
—NHC(=O)NH—.

An amino group of $L^1$ that connects to $L^2$ may be the N-terminus of an amino acid or may be derived from an amino group of an amino acid side chain, for example a lysine amino acid side chain.

An carboxyl group of $L^1$ that connects to $L^2$ may be the C-terminus of an amino acid or may be derived from a carboxyl group of an amino acid side chain, for example a glutamic acid amino acid side chain.

A hydroxy group of $L^1$ that connects to $L^2$ may be derived from a hydroxy group of an amino acid side chain, for example a serine amino acid side chain.

In one embodiment, —C(=O)O— and $L^2$ together form the group:

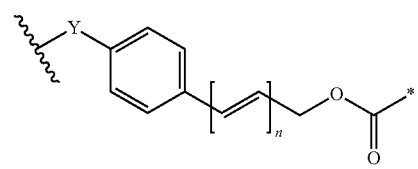

where the asterisk indicates the point of attachment to the N10 position, the wavy line indicates the point of attachment to the linker $L^1$, Y is —N(H)—, —O—, —C(=O)N(H)— or —C(=O)O—, and n is 0 to 3. The phenylene ring is optionally substituted with one, two or three substituents as described herein. In one embodiment, the phenylene group is optionally substituted with halo, $NO_2$, R or OR.

In one embodiment, Y is NH.

In one embodiment, n is 0 or 1. Preferably, n is 0.

Where Y is NH and n is 0, the self-immolative linker may be referred to as a p-aminobenzylcarbonyl linker (PABC).

The self-immolative linker will allow for release of the protected compound when a remote site is activated, proceeding along the lines shown below (for n=0):

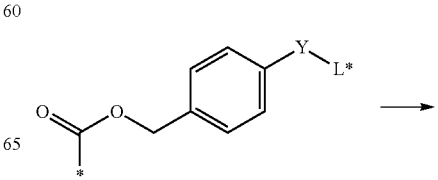

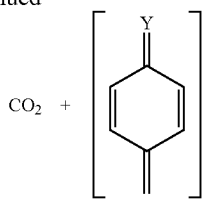

where L* is the activated form of the remaining portion of the linker. These groups have the advantage of separating the site of activation from the compound being protected. As described above, the phenylene group may be optionally substituted.

In one embodiment described herein, the group L* is a linker $L^1$ as described herein, which may include a dipeptide group.

In another embodiment, —C(=O)O— and $L^2$ together form a group selected from:

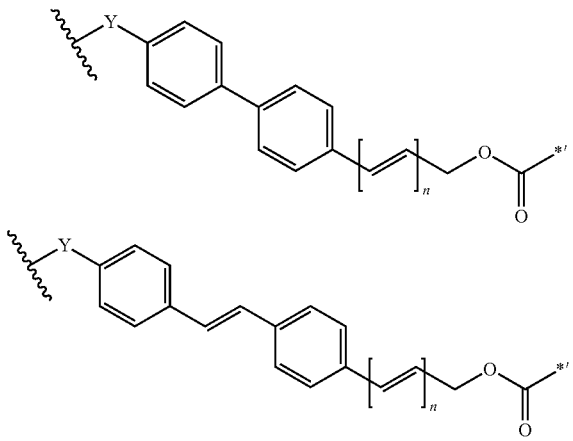

where the asterisk, the wavy line, Y, and n are as defined above. Each phenylene ring is optionally substituted with one, two or three substituents as described herein. In one embodiment, the phenylene ring having the Y substituent is optionally substituted and the phenylene ring not having the Y substituent is unsubstituted. In one embodiment, the phenylene ring having the Y substituent is unsubstituted and the phenylene ring not having the Y substituent is optionally substituted.

In another embodiment, —C(=O)O— and $L^2$ together form a group selected from:

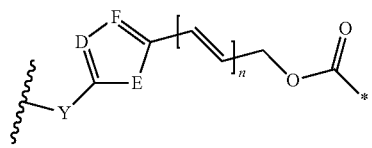

where the asterisk, the wavy line, Y, and n are as defined above, E is O, S or NR, D is N, CH, or CR, and F is N, CH, or CR.

In one embodiment, D is N.
In one embodiment, D is CH.
In one embodiment, E is O or S.
In one embodiment, F is CH.

In a preferred embodiment, the linker is a cathepsin labile linker.

In one embodiment, $L^1$ comprises a dipeptide The dipeptide may be represented as —NH—$X_1$—$X_2$—CO—, where —NH— and —CO— represent the N- and C-terminals of the amino acid groups $X_1$ and $X_2$ respectively. The amino acids in the dipeptide may be any combination of natural amino acids. Where the linker is a cathepsin labile linker, the dipeptide may be the site of action for cathepsin-mediated cleavage.

Additionally, for those amino acids groups having carboxyl or amino side chain functionality, for example Glu and Lys respectively, CO and NH may represent that side chain functionality.

In one embodiment, the group —$X_1$—$X_2$— in dipeptide, —NH—$X_1$—$X_2$—CO—, is selected from:
-Phe-Lys-,
-Val-Ala-,
-Val-Lys-,
-Ala-Lys-,
-Val-Cit-,
-Phe-Cit-,
-Leu-Cit-,
-Ile-Cit-,
-Phe-Arg-,
-Trp-Cit-
where Cit is citrulline.

Preferably, the group —$X_1$—$X_2$— in dipeptide, —NH—$X_1$—$X_2$—CO—, is selected from:
-Phe-Lys-,
-Val-Ala-,
-Val-Lys-,
-Ala-Lys-,
-Val-Cit-.

Most preferably, the group —$X_1$—$X_2$— in dipeptide, —NH—$X_1$—$X_2$—CO—, is -Phe-Lys- or -Val-Ala-. In some embodiments, the group —$X_1$—$X_2$— in dipeptide, —NH—$X_1$—$X_2$—CO—, is -Val-Cit-.

Other dipeptide combinations may be used, including those described by Dubowchik et al. (*Bioconjugate Chem.* 2002, 13, 855-869), which is incorporated herein by reference.

In one embodiment, the amino acid side chain is chemically protected, where appropriate. The side chain protecting group may be a group as discussed below in relation to the group $R^L$. The present inventors have established that protected amino acid sequences are cleavable by enzymes. For example, the present inventors have established that a dipeptide sequence comprising a Boc side chain-protected Lys residue is cleavable by cathepsin.

Protecting groups for the side chains of amino acids are well known in the art and are described in the Novabiochem Catalog. Additional protecting group strategies are set out in Protective Groups in Organic Synthesis, Greene and Wuts.

Possible side chain protecting groups are shown below for those amino acids having reactive side chain functionality:
Arg: Z, Mtr, Tos;
Asn: Trt, Xan;
Asp: Bzl, t-Bu;
Cys: Acm, Bzl, Bzl-OMe, Bzl-Me, Trt;
Glu: Bzl, t-Bu;
Gln: Trt, Xan;
His: Boc, Dnp, Tos, Trt;
Lys: Boc, Z—Cl, Fmoc, Z, Alloc;
Ser: Bzl, TBDMS, TBDPS;
Thr: Bz;
Trp: Boc;
Tyr: Bzl, Z, Z—Br.

In other embodiments of the invention, the amino acids selected are those having no reactive side chain functionality. For example, the amino acids may be selected from: Ala, Gly, Ile, Leu, Met, Phe, Pro, and Val.

In one embodiment, the dipeptide is used in combination with a self-immolative linker. The self-immolative linker may be connected to —$X_2$—.

In one embodiment, the dipeptide is used in combination with a self-immolative linker. The self-immolative linker may be connected to —$X_2$—.

Where a self-immolative linker is present, —$X_2$— is connected directly to the self-immolative linker. Preferably the group —$X_2$—CO— is connected to Y, where Y is NH, thereby forming the group —$X_2$—CO—NH—.

—NH—$X_1$— is connected directly to A. A may comprise the functionality —CO— thereby to form an amide link with —$X_1$—.

In one embodiment, $L^1$ and $L^2$ together with —OC(=O)— comprise the group NH—$X_1$—$X_2$—CO-PABC-. The PABC group is connected directly to the N10 position. Preferably, the self-immolative linker and the dipeptide together form the group —NH-Phe-Lys-CO—NH-PABC-, which is illustrated below:

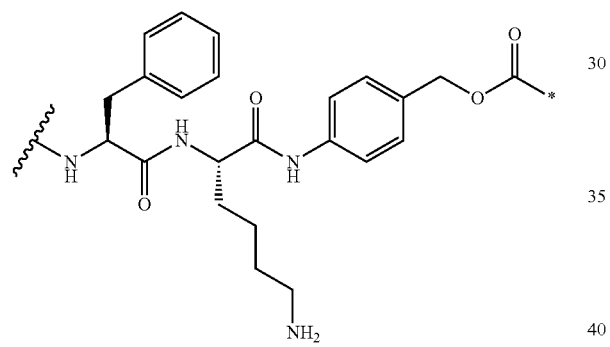

where the asterisk indicates the point of attachment to the N10 position, and the wavy line indicates the point of attachment to the remaining portion of the linker $L^1$ or the point of attachment to A. Preferably, the wavy line indicates the point of attachment to A. The side chain of the Lys amino acid may be protected, for example, with Boc, Fmoc, or Alloc, as described above.

Alternatively, the self-immolative linker and the dipeptide together form the group —NH-Val-Ala-CO—NH-PABC-, which is illustrated below:

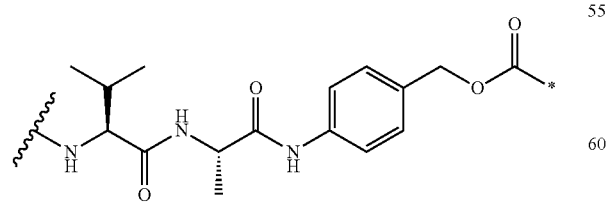

where the asterisk and the wavy line are as defined above.

In one embodiment, $L^2$ together with —OC(=O)— represents:

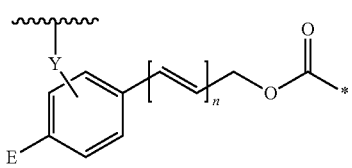

where the asterisk indicates the point of attachment to the N10 position, the wavy line indicates the point of attachment to $L^1$, n is 0 to 3, Y is a covalent bond or a functional group, and E is an activatable group, for example by enzymatic action or light, thereby to generate a self-immolative unit. The phenylene ring is optionally further substituted with one, two or three substituents as described herein. In one embodiment, the phenylene group is optionally further substituted with halo, $NO_2$, R or OR. Preferably n is 0 or 1, most preferably 0.

E is selected such that the group is susceptible to activation, e.g. by light or by the action of an enzyme. E may be —$NO_2$ or glucoronic acid. The former may be susceptible to the action of a nitroreductase, the latter to the action of a β-glucoronidase.

In this embodiment, the self-immolative linker will allow for release of the protected compound when E is activated, proceeding along the lines shown below (for n=0):

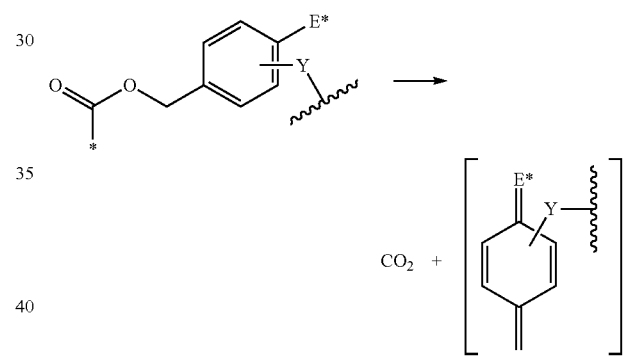

where the asterisk indicates the point of attachment to the N10 position, E* is the activated form of E, and Y is as described above. These groups have the advantage of separating the site of activation from the compound being protected. As described above, the phenylene group may be optionally further substituted.

The group Y may be a covalent bond to $L^1$.
The group Y may be a functional group selected from:
—C(=O)—
—NH—
—O—
—C(=O)NH—,
—C(=O)O—,
—NHC(=O)—,
—OC(=O)—,
—OC(=O)O—,
—NHC(=O)O—,
—OC(=O)NH—,
—NHC(=O)NH—,
—NHC(=O)NH,
—C(=O)NHC(=O)—, and
—S—.

Where $L^1$ is a dipeptide, it is preferred that Y is —NH— or —C(=O)—, thereby to form an amide bond between $L^1$ and Y. In this embodiment, the dipeptide sequence need not be a substrate for an enzymatic activity.

In another embodiment, G is intended to form a spacer group that is suitable for indirectly connecting $L^1$ to a cell binding agent.

$L^1$ and $G^1$ may be connected by a bond selected from:
—C(═O)NH—,
—C(═O)O—,
—NHC(═O)—,
—OC(═O)—,
—OC(═O)O—,
—NHC(═O)O—,
—OC(═O)NH—, and
—NHC(═O)NH—.

In one embodiment, the functional group $G^1$ is or comprises an amino, carboxylic acid, hydroxy, thiol, or maleimide group for reaction with an appropriate group on the cell binding agent. In a preferred embodiment, $G^1$ comprises a maleimide group.

In one embodiment, the group $G^1$ is an alkyl maleimide group. This group is suitable for reaction with thiol groups, particularly cysteine thiol groups, present in the cell binding agent, for example present in an antibody.

In one embodiment, the group $G^1$ is:

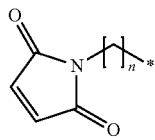

where the asterisk indicates the point of attachment to $L^1$ and n is 0 to 6. In one embodiment, n is 5.

In one embodiment, the group $G^1$ is:

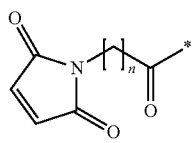

where the asterisk indicates the point of attachment to $L^1$ and n is 0 to 6. In one embodiment, n is 5.

In one embodiment, the group $G^1$ is:

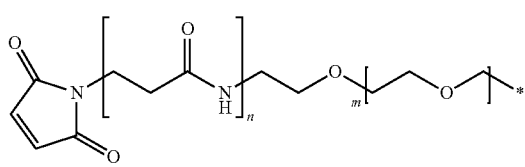

where the asterisk indicates the point of attachment to $L^1$, n is 0 or 1, and m is 0 to 30. In a preferred embodiment, n is 1 and m is 0 to 10, 1 to 7, preferably 3 to 7, and most preferably 3 or 7.

In one embodiment, the group $G^1$ is:

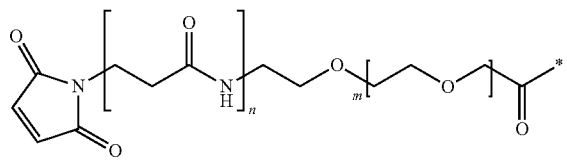

where the asterisk indicates the point of attachment to $L^1$, n is 0 or 1, and m is 0 to 30. In a preferred embodiment, n is 1 and m is 0 to 10, 1 to 7, preferably 3 to 7, and most preferably 3 or 7.

In each of the embodiments above, an alternative functionality may be used in place of the maleimide group shown below:

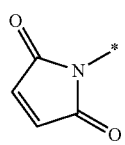 [SMILES: *N1C(=O)C=CC1=O]

where asterisk indicates the bond to the remaining portion of the G group.

In one embodiment, the maleimide-derived group is replaced with the group:

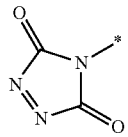

where the asterisk indicates the bond to the remaining portion of the G group.

In one embodiment, the maleimide group is replaced with a group selected from:
—C(═O)OH,
—OH,
—NH₂,
—SH,
—C(═O)CH₂X, where X is Cl, Br or I,
—CHO,
—NHNH₂
—C≡CH, and
—N₃ (azide).

In particular embodiments, the maleimide group may be replaced by —C(═O)CH₂I. Thus, in particular embodiments, the group $G^1$ is:

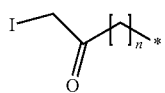

where the asterisk indicates the point of attachment to $L^1$ and n is 0 to 6. In one embodiment, n is 0.

In particular embodiments, the group $G^1$ is:

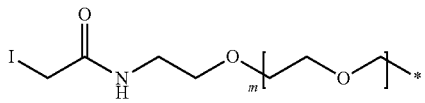

where the asterisk indicates the point of attachment to $L^1$, m is 0 to 30. In a preferred embodiment, m is 0 to 10, 1 to 7, preferably 3 to 7, and most preferably 3 or 7.

In particular embodiments, the group $G^1$ is:

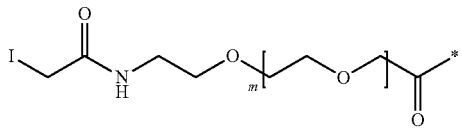

where the asterisk indicates the point of attachment to $L^1$, m is 0 to 30. In a preferred embodiment, m is 0 to 10, 1 to 7, preferably 3 to 7, and most preferably 3 or 7.

In one embodiment, where $L^1$ is present, $G^1$ is —NH$_2$, —NHMe, —COOH, —OH or —SH.

In one embodiment, where $L^1$ is present, $G^1$ is —NH$_2$ or —NHMe. Either group may be the N-terminal of an $L^1$ amino acid sequence.

In one embodiment, where $L^1$ is present, $G^1$ is —NH$_2$, and L is an amino acid sequence —X$_1$—X$_2$—, as defined above in relation to $R^{10}$.

In one embodiment, where $L^1$ is present, $G^1$ is COOH. This group may be the C-terminal of an $L^1$ amino acid sequence.

In one embodiment, where $L^1$ is present, $G^1$ is OH.

In one embodiment, where $L^1$ is present, $G^1$ is SH.

The group $G^1$ may be convertable from one functional group to another. In one embodiment, where $L^1$ is present, $G^1$ is —NH$_2$. This group is convertable to another group $G^1$ comprising a maleimide group. For example, the group —NH$_2$ may be reacted with an acid or an activated acid (e.g. N-succinimide forms) of those $G^1$ groups comprising maleimide shown above.

The group $G^1$ may therefore be converted to a functional group that is more appropriate for reaction with a cell binding agent.

In other embodiments, $R^L$ is a group that is a precursor to the linker that is provided with a functional group.

As noted above, in one embodiment, where $L^1$ is present, $G^1$ is —NH$_2$, —NHMe, —COOH, —OH or —SH. In a further embodiment, these groups are provided in a chemically protected form. The chemically protected form is therefore a precursor to the linker that is provided with a functional group.

In one embodiment, $G^1$ is —NH$_2$ in a chemically protected form. The group may be protected with a carbamate protecting group. The carbamate protecting group may be selected from the group consisting of:

Alloc, Fmoc, Boc, Troc, Teoc, Cbz and PNZ.

Preferably, where $G^1$ is —NH$_2$, it is protected with an Alloc or Fmoc group.

In one embodiment, particularly where the compound is a dimer, the nitrogen protecting group for one of the PBD units is a group $R^L$ and the nitrogen protecting group for the other of the PBD units is a capping group, $R^{Cap}$:

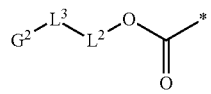

where the asterisk indicates the point of attachment to the N10 position, $G^2$ is a terminating group, $L^3$ is a covalent bond or a cleavable linker $L^1$, $L^2$ is a covalent bond or together with OC(=O) forms a self-immolative linker.

The protecting group $R^C$ is removable from the N10 position thereby to provide the imine or carbinolamine form of the PBD. The term "capping group" is used to indicate that $R^C$ is prevented from reacting with a cell binding agent, such as an antibody. Instead, the group $R^L$ is for connection to a cell binding agent.

Where $L^3$ and $L^2$ are both covalent bonds, $G^2$ and —OC(=O)— together form a carbamate protecting group such as shown above in Table 1.

$L^1$ is as defined above in relation to $R^L$.

$L^2$ is as defined above in relation to $R^L$.

In one embodiment $L^3$ is a cleavable linker $L^1$, and $L^2$, together with OC(=O), forms a self-immolative linker. In this embodiment, $G^2$ is Ac (acetyl) or Moc, or a carbamate protecting group selected from:

Alloc, Fmoc, Boc, Troc, Teoc, Psec, Cbz and PNZ.

In one embodiment $L^3$ is a cleavable linker $L^1$, and $L^2$, together with OC(=O), forms a self-immolative linker. In this embodiment, $G^2$ together with OC(=O), is a carbamate protecting group selected from Table 1 above.

$G^2$ is different to $G^1$. Furthermore, it is preferred that $G^1$ is removable under conditions that do not remove $G^1$.

Substituents

The phrase "optionally substituted" as used herein, pertains to a parent group which may be unsubstituted or which may be substituted.

Unless otherwise specified, the term "substituted" as used herein, pertains to a parent group which bears one or more substitutents. The term "substituent" is used herein in the conventional sense and refers to a chemical moiety which is covalently attached to, or if appropriate, fused to, a parent group. A wide variety of substituents are well known, and methods for their formation and introduction into a variety of parent groups are also well known.

Examples of substituents are described in more detail below.

$C_{1-12}$ alkyl: The term "$C_{1-12}$ alkyl" as used herein, pertains to a monovalent moiety obtained by removing a hydrogen atom from a carbon atom of a hydrocarbon compound having from 1 to 12 carbon atoms, which may be aliphatic or alicyclic, and which may be saturated or unsaturated (e.g. partially unsaturated, fully unsaturated). Thus, the term "alkyl" includes the sub-classes alkenyl, alkynyl, cycloalkyl, etc., discussed below.

Examples of saturated alkyl groups include, but are not limited to, methyl ($C_1$), ethyl ($C_2$), propyl ($C_3$), butyl ($C_4$), pentyl ($C_5$), hexyl ($C_6$) and heptyl ($C_7$).

Examples of saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$) and n-heptyl ($C_7$).

Examples of saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

$C_{2-12}$ Alkenyl: The term "$C_{2-12}$ alkenyl" as used herein, pertains to an alkyl group having one or more carbon-carbon double bonds.

Examples of unsaturated alkenyl groups include, but are not limited to, ethenyl (vinyl, —CH=CH$_2$), 1-propenyl (—CH=CH—CH$_3$), 2-propenyl (allyl, —CH—CH=CH$_2$), isopropenyl (1-methylvinyl, —C(CH$_3$)=CH$_2$), butenyl (C$_4$), pentenyl (C$_5$), and hexenyl (C$_6$).

C$_{2-12}$ alkynyl: The term "C$_{2-12}$ alkynyl" as used herein, pertains to an alkyl group having one or more carbon-carbon triple bonds.

Examples of unsaturated alkynyl groups include, but are not limited to, ethynyl (ethinyl, —C≡CH) and 2-propynyl (propargyl, —CH$_2$—C≡CH).

C$_{3-12}$ cycloalkyl: The term "C$_{3-12}$ cycloalkyl" as used herein, pertains to an alkyl group which is also a cyclyl group; that is, a monovalent moiety obtained by removing a hydrogen atom from an alicyclic ring atom of a cyclic hydrocarbon (carbocyclic) compound, which moiety has from 3 to 7 carbon atoms, including from 3 to 7 ring atoms.

Examples of cycloalkyl groups include, but are not limited to, those derived from:

saturated monocyclic hydrocarbon compounds:
cyclopropane (C$_3$), cyclobutane (C$_4$), cyclopentane (C$_5$), cyclohexane (C$_6$), cycloheptane (C$_7$), methylcyclopropane (C$_4$), dimethylcyclopropane (C$_5$), methylcyclobutane (C$_5$), dimethylcyclobutane (C$_6$), methylcyclopentane (C$_6$), dimethylcyclopentane (C$_7$) and methylcyclohexane (C$_7$);

unsaturated monocyclic hydrocarbon compounds:
cyclopropene (C$_3$), cyclobutene (C$_4$), cyclopentene (C$_5$), cyclohexene (C$_6$), methylcyclopropene (C$_4$), dimethylcyclopropene (C$_5$), methylcyclobutene (C$_5$), dimethylcyclobutene (C$_6$), methylcyclopentene (C$_6$), dimethylcyclopentene (C$_7$) and methylcyclohexene (C$_7$); and saturated polycyclic hydrocarbon compounds:
norcarane (C$_7$), norpinane (C$_7$), norbornane (C$_7$).

C$_{3-20}$ heterocyclyl: The term "C$_{3-20}$ heterocyclyl" as used herein, pertains to a monovalent moiety obtained by removing a hydrogen atom from a ring atom of a heterocyclic compound, which moiety has from 3 to 20 ring atoms, of which from 1 to 10 are ring heteroatoms. Preferably, each ring has from 3 to 7 ring atoms, of which from 1 to 4 are ring heteroatoms.

In this context, the prefixes (e.g. C$_{3-20}$, C$_{3-7}$, C$_{5-6}$, etc.) denote the number of ring atoms, or range of number of ring atoms, whether carbon atoms or heteroatoms. For example, the term "C$_{5-6}$heterocyclyl", as used herein, pertains to a heterocyclyl group having 5 or 6 ring atoms.

Examples of monocyclic heterocyclyl groups include, but are not limited to, those derived from:

N$_1$: aziridine (C$_3$), azetidine (C$_4$), pyrrolidine (tetrahydropyrrole) (C$_5$), pyrroline (e.g., 3-pyrroline, 2,5-dihydropyrrole) (C$_5$), 2H-pyrrole or 3H-pyrrole (isopyrrole, isoazole) (C$_5$), piperidine (C$_6$), dihydropyridine (C$_6$), tetrahydropyridine (C$_6$), azepine (C$_7$);

O$_1$: oxirane (C$_3$), oxetane (C$_4$), oxolane (tetrahydrofuran) (C$_5$), oxole (dihydrofuran) (C$_5$), oxane (tetrahydropyran) (C$_6$), dihydropyran (C$_6$), pyran (C$_6$), oxepin (C$_7$);

S$_1$: thiirane (C$_3$), thietane (C$_4$), thiolane (tetrahydrothiophene) (C$_5$), thiane (tetrahydrothiopyran) (C$_6$), thiepane (C$_7$);

O$_2$: dioxolane (C$_5$), dioxane (C$_6$), and dioxepane (C$_7$);
O$_3$: trioxane (C$_6$);
N$_2$: imidazolidine (C$_5$), pyrazolidine (diazolidine) (C$_5$), imidazoline (C$_5$), pyrazoline (dihydropyrazole) (C$_5$), piperazine (C$_6$);
N$_1$O$_1$: tetrahydrooxazole (C$_5$), dihydrooxazole (C$_5$), tetrahydroisoxazole (C$_5$), dihydroisoxazole (C$_5$), morpholine (C$_6$), tetrahydrooxazine (C$_6$), dihydrooxazine (C$_6$), oxazine (C$_6$);
N$_1$S$_1$: thiazoline (C$_5$), thiazolidine (C$_5$), thiomorpholine (C$_6$);
N$_2$O$_1$: oxadiazine (C$_6$);
O$_1$S$_1$: oxathiole (C$_5$) and oxathiane (thioxane) (C$_6$); and,
N$_1$O$_1$S$_1$: oxathiazine (C$_6$).

Examples of substituted monocyclic heterocyclyl groups include those derived from saccharides, in cyclic form, for example, furanoses (C$_5$), such as arabinofuranose, lyxofuranose, ribofuranose, and xylofuranse, and pyranoses (C$_6$), such as allopyranose, altropyranose, glucopyranose, mannopyranose, gulopyranose, idopyranose, galactopyranose, and talopyranose.

C$_{5-20}$ aryl: The term "C$_{5-20}$ aryl", as used herein, pertains to a monovalent moiety obtained by removing a hydrogen atom from an aromatic ring atom of an aromatic compound, which moiety has from 3 to 20 ring atoms. Preferably, each ring has from 5 to 7 ring atoms.

In this context, the prefixes (e.g. C$_{3-20}$, C$_{5-7}$, C$_{5-6}$, etc.) denote the number of ring atoms, or range of number of ring atoms, whether carbon atoms or heteroatoms. For example, the term "C$_{5-6}$ aryl" as used herein, pertains to an aryl group having 5 or 6 ring atoms.

The ring atoms may be all carbon atoms, as in "carboaryl groups".

Examples of carboaryl groups include, but are not limited to, those derived from benzene (i.e. phenyl) (C$_6$), naphthalene (C$_{10}$), azulene (C$_{10}$), anthracene (C$_{14}$), phenanthrene (C$_{14}$), naphthacene (C$_{18}$), and pyrene (C$_{16}$).

Examples of aryl groups which comprise fused rings, at least one of which is an aromatic ring, include, but are not limited to, groups derived from indane (e.g. 2,3-dihydro-1H-indene) (C$_9$), indene (C$_9$), isoindene (C$_9$), tetraline (1,2,3,4-tetrahydronaphthalene (C$_{10}$), acenaphthene (C$_{12}$), fluorene (C$_{13}$), phenalene (C$_{13}$), acephenanthrene (C$_{15}$), and aceanthrene (C$_{16}$).

Alternatively, the ring atoms may include one or more heteroatoms, as in "heteroaryl groups". Examples of monocyclic heteroaryl groups include, but are not limited to, those derived from:

N$_1$: pyrrole (azole) (C$_5$), pyridine (azine) (C$_6$);
O$_1$: furan (oxole) (C$_5$);
S$_1$: thiophene (thiole) (C$_5$);
N$_1$O$_1$: oxazole (C$_5$), isoxazole (C$_5$), isoxazine (C$_6$);
N$_2$O$_1$: oxadiazole (furazan) (C$_5$);
N$_3$O$_1$: oxatriazole (C$_5$);
N$_1$S$_1$: thiazole (C$_5$), isothiazole (C$_5$);
N$_2$: imidazole (1,3-diazole) (C$_5$), pyrazole (1,2-diazole) (C$_5$), pyridazine (1,2-diazine) (C$_6$), pyrimidine (1,3-diazine) (C$_6$) (e.g., cytosine, thymine, uracil), pyrazine (1,4-diazine) (C$_6$);
N$_3$: triazole (C$_5$), triazine (C$_6$); and,
N$_4$: tetrazole (C$_5$).

Examples of heteroaryl which comprise fused rings, include, but are not limited to:

C$_9$ (with 2 fused rings) derived from benzofuran (O$_1$), isobenzofuran (O$_1$), indole (N$_1$), isoindole (N$_1$), indolizine (N$_1$), indoline (N$_1$), isoindoline (N$_1$), purine (N$_4$) (e.g., adenine, guanine), benzimidazole (N$_2$), indazole (N$_2$), benzoxazole (N$_1$O$_1$), benzisoxazole (N$_1$O$_1$), benzodioxole (O$_2$), benzofurazan (N$_2$O$_1$), benzotriazole (N$_3$), benzothiofuran (S$_1$), benzothiazole (N$_1$S$_1$), benzothiadiazole (N$_2$S);

C$_{10}$ (with 2 fused rings) derived from chromene (O$_1$), isochromene (O$_1$), chroman (O$_1$), isochroman (O$_1$), benzodioxan (O$_2$), quinoline (N$_1$), isoquinoline (N$_1$), quinolizine (N$_1$), benzoxazine (N$_1$O$_1$), benzodiazine (N$_2$), pyridopyridine ($N_2$), quinoxaline ($N_2$), quinazoline ($N_2$), cinnoline ($N_2$), phthalazine ($N_2$), naphthyridine ($N_2$), pteridine ($N_4$);

$C_{11}$ (with 2 fused rings) derived from benzodiazepine ($N_2$);

$C_{13}$ (with 3 fused rings) derived from carbazole ($N_1$), dibenzofuran ($O_1$), dibenzothiophene ($S_1$), carboline ($N_2$), perimidine ($N_2$), pyridoindole ($N_2$); and, $C_{14}$ (with 3 fused rings) derived from acridine ($N_1$), xanthene ($O_1$), thioxanthene ($S_1$), oxanthrene ($O_2$), phenoxathiin ($O_1S_1$), phenazine ($N_2$), phenoxazine ($N_1O_1$), phenothiazine ($N_1S_1$), thianthrene ($S_2$), phenanthridine ($N_1$), phenanthroline ($N_2$), phenazine ($N_2$).

The above groups, whether alone or part of another substituent, may themselves optionally be substituted with one or more groups selected from themselves and the additional substituents listed below.

N atoms in heterocyclyl and heteroaryl groups may be substituted by with $O_{1-12}$ alkyl, where appropriate.

Halo: —F, —Cl, —Br, and —I.

Hydroxy: —OH.

Ether: —OR, wherein R is an ether substituent, for example, a $C_{1-7}$ alkyl group (also referred to as a $C_{1-7}$ alkoxy group, discussed below), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$ alkyl group.

Alkoxy: —OR, wherein R is an alkyl group, for example, a $C_{1-7}$ alkyl group. Examples of $C_{1-7}$ alkoxy groups include, but are not limited to, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy).

Acetal: —CH(OR$^1$)(OR$^2$), wherein R$^1$ and R$^2$ are independently acetal substituents, for example, a $C_{1-7}$ alkyl group, a $C_{3-20}$ heterocyclyl group, or a $C_{5-20}$ aryl group, preferably a $C_{1-7}$ alkyl group, or, in the case of a "cyclic" acetal group, R$^1$ and R$^2$, taken together with the two oxygen atoms to which they are attached, and the carbon atoms to which they are attached, form a heterocyclic ring having from 4 to 8 ring atoms. Examples of acetal groups include, but are not limited to, —CH(OMe)$_2$, —CH(OEt)$_2$, and —CH(OMe)(OEt).

Hemiacetal: —CH(OH)(OR$^1$), wherein R$^1$ is a hemiacetal substituent, for example, a $C_{1-7}$ alkyl group, a $C_{3-20}$ heterocyclyl group, or a $C_{5-20}$ aryl group, preferably a $C_{1-7}$ alkyl group. Examples of hemiacetal groups include, but are not limited to, —CH(OH)(OMe) and —CH(OH)(OEt).

Ketal: —CR(OR$^1$)(OR$^2$), where R$^1$ and R$^2$ are as defined for acetals, and R is a ketal substituent other than hydrogen, for example, a $C_{1-7}$ alkyl group, a $C_{3-20}$ heterocyclyl group, or a $C_{5-20}$ aryl group, preferably a $C_{1-7}$ alkyl group. Examples ketal groups include, but are not limited to, —C(Me)(OMe)$_2$, —C(Me)(OEt)$_2$, —C(Me)(OMe)(OEt), —C(Et)(OMe)$_2$, —C(Et)(OEt)$_2$, and —C(Et)(OMe)(OEt).

Hemiketal: —CR(OH)(OR$^1$), where R$^1$ is as defined for hemiacetals, and R is a hemiketal substituent other than hydrogen, for example, a $C_{1-7}$ alkyl group, a $C_{3-20}$ heterocyclyl group, or a $C_{5-20}$ aryl group, preferably a $C_{1-7}$ alkyl group. Examples of hemiacetal groups include, but are not limited to, —C(Me)(OH)(OMe), —C(Et)(OH)(OMe), —C(Me)(OH)(OEt), and —C(Et)(OH)(OEt).

Oxo (keto, -one): =O.

Thione (thioketone): =S.

Imino (imine): =NR, wherein R is an imino substituent, for example, hydrogen, $C_{1-7}$ alkyl group, a $C_{3-20}$ heterocyclyl group, or a $C_{5-20}$ aryl group, preferably hydrogen or a $C_{1-7}$ alkyl group. Examples of ester groups include, but are not limited to, =NH, =NMe, =NEt, and =NPh.

Formyl (carbaldehyde, carboxaldehyde): —O(=O)H.

Acyl (keto): —C(=O)R, wherein R is an acyl substituent, for example, a $C_{1-7}$ alkyl group (also referred to as $C_{1-7}$ alkylacyl or $C_{1-7}$ alkanoyl), a $C_{3-20}$ heterocyclyl group (also referred to as $O_{3-20}$ heterocyclylacyl), or a $C_{5-20}$ aryl group (also referred to as $C_{5-20}$ arylacyl), preferably a $C_{1-7}$ alkyl group. Examples of acyl groups include, but are not limited to, —C(=O)CH$_3$ (acetyl), —C(=O)CH$_2$CH$_3$ (propionyl), —C(=O)C(CH$_3$)$_3$ (t-butyryl), and —C(=O)Ph (benzoyl, phenone).

Carboxy (carboxylic acid): —C(=O)OH.

Thiocarboxy (thiocarboxylic acid): —C(=S)SH.

Thiolocarboxy (thiolocarboxylic acid): —C(=O)SH.

Thionocarboxy (thionocarboxylic acid): —C(=S)OH.

Imidic acid: —C(=NH)OH.

Hydroxamic acid: —C(=NOH)OH.

Ester (carboxylate, carboxylic acid ester, oxycarbonyl): —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy (reverse ester): —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Oxycarboyloxy: —OC(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —OC(=O)OCH$_3$, —OC(=O)OCH$_2$CH$_3$, —OC(=O)OC(CH$_3$)$_3$, and —OC(=O)OPh.

Amino: —NR$^1$R$^2$, wherein R$^1$ and R$^2$ are independently amino substituents, for example, hydrogen, a $C_{1-7}$ alkyl group (also referred to as $C_{1-7}$ alkylamino or di-$C_{1-7}$ alkylamino), a $C_{3-20}$ heterocyclyl group, or a $C_{5-20}$ aryl group, preferably H or a $C_{1-7}$ alkyl group, or, in the case of a "cyclic" amino group, R$^1$ and R$^2$, taken together with the nitrogen atom to which they are attached, form a heterocyclic ring having from 4 to 8 ring atoms. Amino groups may be primary (—NH$_2$), secondary (—NHR$^1$), or tertiary (—NHR$^1$R$^2$), and in cationic form, may be quaternary (—$^+$NR$^1$R$^2$R$^3$). Examples of amino groups include, but are not limited to, —NH$_2$, —NHCH$_3$, —NHC(CH$_3$)$_2$, —N(CH$_3$)$_2$, —N(CH$_2$CH$_3$)$_2$, and —NHPh. Examples of cyclic amino groups include, but are not limited to, aziridino, azetidino, pyrrolidino, piperidino, piperazino, morpholino, and thiomorpholino.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinocarbonyl.

Thioamido (thiocarbamyl): —C(=S)NR$^1$R$^2$, wherein R$^1$ and R$^2$ are independently amino substituents, as defined for amino groups. Examples of amido groups include, but are not limited to, —C(=S)NH$_2$, —C(=S)NHCH$_3$, —C(=S)N(CH$_3$)$_2$, and —C(=S)NHCH$_2$CH$_3$.

Acylamido (acylamino): —NR$^1$C(=O)R$^2$, wherein R$^1$ is an amide substituent, for example, hydrogen, a $C_{1-7}$ alkyl group, a C$_{3-20}$ heterocyclyl group, or a C$_{5-20}$ aryl group, preferably hydrogen or a C$_{1-7}$ alkyl group, and R$^2$ is an acyl substituent, for example, a C$_{1-7}$ alkyl group, a C$_{3-20}$ heterocyclyl group, or a C$_{5-20}$aryl group, preferably hydrogen or a C$_{1-7}$ alkyl group. Examples of acylamide groups include, but are not limited to, —NHC(=O)CH$_3$, —NHC(=O)CH$_2$CH$_3$, and —NHC(=O)Ph. R$^1$ and R$^2$ may together form a cyclic structure, as in, for example, succinimidyl, maleimidyl, and phthalimidyl:

succinimidyl     maleimidyl     phthalimidyl

Aminocarbonyloxy: —OC(=O)NR$^1$R$^2$, wherein R$^1$ and R$^2$ are independently amino substituents, as defined for amino groups. Examples of aminocarbonyloxy groups include, but are not limited to, —OC(=O)NH$_2$, —OC(=O)NHMe, —OC(=O)NMe$_2$, and —OC(=O)NEt$_2$.

Ureido: —N(R$^1$)CONR$^2$R$^3$ wherein R$^2$ and R$^3$ are independently amino substituents, as defined for amino groups, and R$^1$ is a ureido substituent, for example, hydrogen, a C$_{1-7}$ alkyl group, a C$_{3-20}$ heterocyclyl group, or a C$_{5-20}$ aryl group, preferably hydrogen or a C$_{1-7}$ alkyl group. Examples of ureido groups include, but are not limited to, —NHCONH$_2$, —NHCONHMe, —NHCONHEt, —NHCONMe$_2$, —NHCONEt$_2$, —NMeCONH$_2$, —NMeCONHMe, —NMeCONHEt, —NMeCONMe$_2$, and —NMeCONEt$_2$.

Guanidino: —NH—C(=NH)NH$_2$.

Tetrazolyl: a five membered aromatic ring having four nitrogen atoms and one carbon atom, Imino: =NR, wherein R is an imino substituent, for example, for example, hydrogen, a C$_{1-7}$ alkyl group, a C$_{3-20}$ heterocyclyl group, or a C$_{5-20}$ aryl group, preferably H or a C$_{1-7}$alkyl group. Examples of imino groups include, but are not limited to, =NH, =NMe, and =NEt.

Amidine (amidino): —C(=NR)NR$_2$, wherein each R is an amidine substituent, for example, hydrogen, a C$_{1-7}$ alkyl group, a C$_{3-20}$ heterocyclyl group, or a C$_{5-20}$ aryl group, preferably H or a C$_{1-7}$ alkyl group. Examples of amidine groups include, but are not limited to, —C(=NH)NH$_2$, —C(=NH)NMe$_2$, and —C(=NMe)NMe$_2$.

Nitro: —NO$_2$.
Nitroso: —NO.
Azido: —N$_3$.
Cyano (nitrile, carbonitrile): —CN.
Isocyano: —NC.
Cyanato: —OCN.
Isocyanato: —NCO.
Thiocyano (thiocyanato): —SCN.
Isothiocyano (isothiocyanato): —NCS.
Sulfhydryl (thiol, mercapto): —SH.

Thioether (sulfide): —SR, wherein R is a thioether substituent, for example, a C$_{1-7}$ alkyl group (also referred to as a C$_{1-7}$alkylthio group), a C$_{3-20}$ heterocyclyl group, or a C$_{5-20}$ aryl group, preferably a C$_{1-7}$ alkyl group. Examples of C$_{1-7}$ alkylthio groups include, but are not limited to, —SCH$_3$ and —SCH$_2$CH$_3$.

Disulfide: —SS—R, wherein R is a disulfide substituent, for example, a C$_{1-7}$ alkyl group, a C$_{3-20}$ heterocyclyl group, or a C$_{5-20}$ aryl group, preferably a C$_{1-7}$ alkyl group (also referred to herein as C$_{1-7}$ alkyl disulfide). Examples of C$_{1-7}$ alkyl disulfide groups include, but are not limited to, —SSCH$_3$ and —SSCH$_2$CH$_3$.

Sulfine (sulfinyl, sulfoxide): —S(=O)R, wherein R is a sulfine substituent, for example, a C$_{1-7}$ alkyl group, a C$_{3-20}$ heterocyclyl group, or a C$_{5-20}$ aryl group, preferably a C$_{1-7}$ alkyl group. Examples of sulfine groups include, but are not limited to, —S(=O)CH$_3$ and —S(=O)CH$_2$CH$_3$.

Sulfone (sulfonyl): —S(=O)$_2$R, wherein R is a sulfone substituent, for example, a C$_{1-7}$ alkyl group, a C$_{3-20}$ heterocyclyl group, or a C$_{5-20}$ aryl group, preferably a C$_{1-7}$ alkyl group, including, for example, a fluorinated or perfluorinated C$_{1-7}$ alkyl group. Examples of sulfone groups include, but are not limited to, —S(=O)$_2$CH$_3$ (methanesulfonyl, mesyl), —S(=O)$_2$CF$_3$ (triflyl), —S(=O)$_2$CH$_2$CH$_3$ (esyl), —S(=O)$_2$C$_4$F$_9$ (nonaflyl), —S(=O)$_2$CH$_2$CF$_3$ (tresyl), —S(=O)$_2$CH$_2$CH$_2$NH$_2$ (tauryl), —S(=O)$_2$Ph (phenylsulfonyl, besyl), 4-methylphenylsulfonyl (tosyl), 4-chlorophenylsulfonyl (closyl), 4-bromophenylsulfonyl (brosyl), 4-nitrophenyl (nosyl), 2-naphthalenesulfonate (napsyl), and 5-dimethylamino-naphthalen-1-ylsulfonate (dansyl).

Sulfinic acid (sulfino): —S(=O)OH, —SO$_2$H.
Sulfonic acid (sulfo): —S(=O)$_2$OH, —SO$_3$H.

Sulfinate (sulfinic acid ester): —S(=O)OR; wherein R is a sulfinate substituent, for example, a C$_{1-7}$ alkyl group, a C$_{3-20}$ heterocyclyl group, or a C$_{5-20}$ aryl group, preferably a C$_{1-7}$ alkyl group. Examples of sulfinate groups include, but are not limited to, —S(=O)OCH$_3$ (methoxysulfinyl; methyl sulfinate) and —S(=O)OCH$_2$CH$_3$ (ethoxysulfinyl; ethyl sulfinate).

Sulfonate (sulfonic acid ester): —S(=O)$_2$OR, wherein R is a sulfonate substituent, for example, a C$_{1-7}$ alkyl group, a C$_{3-20}$ heterocyclyl group, or a C$_{5-20}$ aryl group, preferably a C$_{1-7}$ alkyl group. Examples of sulfonate groups include, but are not limited to, —S(=O)$_2$OCH$_3$ (methoxysulfonyl; methyl sulfonate) and —S(=O)$_2$OCH$_2$CH$_3$ (ethoxysulfonyl; ethyl sulfonate).

Sulfinyloxy: —OS(=O)R, wherein R is a sulfinyloxy substituent, for example, a C$_{1-7}$ alkyl group, a C$_{3-20}$ heterocyclyl group, or a C$_{5-20}$ aryl group, preferably a C$_{1-7}$ alkyl group. Examples of sulfinyloxy groups include, but are not limited to, —OS(=O)CH$_3$ and —OS(=O)CH$_2$CH$_3$.

Sulfonyloxy: —OS(=O)$_2$R, wherein R is a sulfonyloxy substituent, for example, a C$_{1-7}$ alkyl group, a C$_{3-20}$ heterocyclyl group, or a C$_{5-20}$ aryl group, preferably a C$_{1-7}$ alkyl group. Examples of sulfonyloxy groups include, but are not limited to, —OS(=O)$_2$CH$_3$ (mesylate) and —OS(=O)$_2$CH$_2$CH$_3$ (esylate).

Sulfate: —OS(=O)$_2$OR; wherein R is a sulfate substituent, for example, a C$_{1-7}$ alkyl group, a C$_{3-20}$ heterocyclyl group, or a C$_{5-20}$ aryl group, preferably a C$_{1-7}$ alkyl group. Examples of sulfate groups include, but are not limited to, —OS(=O)$_2$OCH$_3$ and —SO(=O)$_2$OCH$_2$CH$_3$.

Sulfamyl (sulfamoyl; sulfinic acid amide; sulfinamide): —S(=O)NR$^1$R$^2$, wherein R$^1$ and R$^2$ are independently amino substituents, as defined for amino groups. Examples of sulfamyl groups include, but are not limited to, —S(=O)

$NH_2$, $-S(=O)NH(CH_3)$, $-S(=O)N(CH_3)_2$, $-S(=O)NH(CH_2CH_3)$, $-S(=O)N(CH_2CH_3)_2$, and $-S(=O)NHPh$.

Sulfonamido (sulfinamoyl; sulfonic acid amide; sulfonamide): $-S(=O)_2NR^1R^2$, wherein $R^1$ and $R^2$ are independently amino substituents, as defined for amino groups. Examples of sulfonamido groups include, but are not limited to, $-S(=O)_2NH_2$, $-S(=O)_2NH(CH_3)$, $-S(=O)_2N(CH_3)_2$, $-S(=O)_2NH(CH_2CH_3)$, $-S(=O)_2N(CH_2CH_3)_2$, and $-S(=O)_2NHPh$.

Sulfamino: $-NR^1S(=O)_2OH$, wherein $R^1$ is an amino substituent, as defined for amino groups. Examples of sulfamino groups include, but are not limited to, $-NHS(=O)_2OH$ and $-N(CH_3)S(=O)_2OH$.

Sulfonamino: $-NR^1S(=O)_2R$, wherein $R^1$ is an amino substituent, as defined for amino groups, and R is a sulfonamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfonamino groups include, but are not limited to, $-NHS(=O)_2CH_3$ and $-N(CH_3)S(=O)_2C_6H_5$.

Sulfinamino: $-NR^1S(=O)R$, wherein $R^1$ is an amino substituent, as defined for amino groups, and R is a sulfinamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfinamino groups include, but are not limited to, $-NHS(=O)CH_3$ and $-N(CH_3)S(=O)C_6H_5$.

Phosphino (phosphine): $-PR_2$, wherein R is a phosphino substituent, for example, $-H$, a $C_{1-7}$ alkyl group, a $C_{3-20}$ heterocyclyl group, or a $C_{5-20}$ aryl group, preferably $-H$, a $C_{1-7}$ alkyl group, or a $C_{5-20}$ aryl group. Examples of phosphino groups include, but are not limited to, $-PH_2$, $-P(CH_3)_2$, $-P(CH_2CH_3)_2$, $-P(t-Bu)_2$, and $-P(Ph)_2$.

Phospho: $-P(=O)_2$.

Phosphinyl (phosphine oxide): $-P(=O)R_2$, wherein R is a phosphinyl substituent, for example, a $C_{1-7}$ alkyl group, a $C_{3-20}$ heterocyclyl group, or a $C_{5-20}$ aryl group, preferably a $C_{1-7}$ alkyl group or a $C_{5-20}$ aryl group. Examples of phosphinyl groups include, but are not limited to, $-P(=O)(CH_3)_2$, $-P(=O)(CH_2CH_3)_2$, $-P(=O)(t-Bu)_2$, and $-P(=O)(Ph)_2$.

Phosphonic acid (phosphono): $-P(=O)(OH)_2$.

Phosphonate (phosphono ester): $-P(=O)(OR)_2$, where R is a phosphonate substituent, for example, $-H$, a $C_{1-7}$ alkyl group, a $C_{3-20}$ heterocyclyl group, or a $C_{5-20}$ aryl group, preferably $-H$, a $C_{1-7}$ alkyl group, or a $C_{5-20}$ aryl group. Examples of phosphonate groups include, but are not limited to, $-P(=O)(OCH_3)_2$, $-P(=O)(OCH_2CH_3)_2$, $-P(=O)(O-t-Bu)_2$, and $-P(=O)(OPh)_2$.

Phosphoric acid (phosphonooxy): $-OP(=O)(OH)_2$.

Phosphate (phosphonooxy ester): $-OP(=O)(OR)_2$, where R is a phosphate substituent, for example, $-H$, a $C_{1-7}$ alkyl group, a $C_{3-20}$ heterocyclyl group, or a $C_{5-20}$ aryl group, preferably $-H$, a $C_{1-7}$ alkyl group, or a $C_{5-20}$ aryl group. Examples of phosphate groups include, but are not limited to, $-OP(=O)(OCH_3)_2$, $-OP(=O)(OCH_2CH_3)_2$, $-OP(=O)(O-t-Bu)_2$, and $-OP(=O)(OPh)_2$.

Phosphorous acid: $-OP(OH)_2$.

Phosphite: $-OP(OR)_2$, where R is a phosphite substituent, for example, $-H$, a $C_{1-7}$ alkyl group, a $C_{3-20}$ heterocyclyl group, or a $C_{5-20}$ aryl group, preferably $-H$, a $C_{1-7}$ alkyl group, or a $C_{5-20}$ aryl group. Examples of phosphite groups include, but are not limited to, $-OP(OCH_3)_2$, $-OP(OCH_2CH_3)_2$, $-OP(O-t-Bu)_2$, and $-OP(OPh)_2$.

Phosphoramidite: $-OP(OR^1)-NR^2_2$, where $R^1$ and $R^2$ are phosphoramidite substituents, for example, $-H$, a (optionally substituted) $C_{1-7}$ alkyl group, a $C_{3-20}$ heterocyclyl group, or a $C_{5-20}$ aryl group. Examples of phosphoramidite groups include, but are not limited to, $-OP(OCH_2CH_3)-N(CH_3)_2$, $-OP(OCH_2CH_3)-N(i-Pr)_2$, and $-OP(OCH_2CH_2CN)-N(i-Pr)_2$.

Phosphoramidate: $-OP(=O)(OR^1)-NR^2_2$, where $R^1$ and $R^2$ are phosphoramidate substituents, for example, $-H$, a (optionally substituted) $C_{1-7}$ alkyl group, a $C_{3-20}$ heterocyclyl group, or a $C_{5-20}$ aryl group, preferably $-H$, a $C_{1-7}$ alkyl group, or a $C_{5-20}$ aryl group. Examples of phosphoramidate groups include, but are not limited to, $-OP(=O)(OCH_2CH_3)-N(CH_3)_2$, $-OP(=O)(OCH_2CH_3)-N(i-Pr)_2$, and $-OP(=O)(OCH_2CH_2CN)-N(i-Pr)_2$.

Alkylene $C_{3-12}$ alkylene: The term "$C_{3-12}$ alkylene", as used herein, pertains to a bidentate moiety obtained by removing two hydrogen atoms, either both from the same carbon atom, or one from each of two different carbon atoms, of a hydrocarbon compound having from 3 to 12 carbon atoms (unless otherwise specified), which may be aliphatic or alicyclic, and which may be saturated, partially unsaturated, or fully unsaturated. Thus, the term "alkylene" includes the sub-classes alkenylene, alkynylene, cycloalkylene, etc., discussed below.

Examples of linear saturated $C_{3-12}$ alkylene groups include, but are not limited to, $-(CH_2)_n-$ where n is an integer from 3 to 12, for example, $-CH_2CH_2CH_2-$ (propylene), $-CH_2CH_2CH_2CH_2-$ (butylene), $-CH_2CH_2CH_2CH_2CH_2-$ (pentylene) and $-CH_2CH_2CH_2CH_2CH_2CH_2CH_2-$ (heptylene).

Examples of branched saturated $C_{3-12}$ alkylene groups include, but are not limited to, $-CH(CH_3)CH_2-$, $-CH(CH_3)CH_2CH_2-$, $-CH(CH_3)CH_2CH_2CH_2-$, $-CH_2CH(CH_3)CH_2-$, $-CH_2CH(CH_3)CH_2CH_2-$, $-CH(CH_2CH_3)-$, $-CH(CH_2CH_3)CH_2-$, and $-CH_2CH(CH_2CH_3)CH_2-$.

Examples of linear partially unsaturated $C_{3-12}$ alkylene groups ($C_{3-12}$ alkenylene, and alkynylene groups) include, but are not limited to, $-CH=CH-CH_2-$, $-CH_2-CH=CH_2-$, $-CH=CH-CH_2-CH_2-$, $-CH=CH-CH_2-CH_2-CH_2-$, $-CH=CH-CH=CH-$, $-CH=CH-CH=CH-CH_2-$, $-CH=CH-CH=CH-CH_2-CH_2-$, $-CH=CH-CH_2-CH=CH-$, $-CH=CH-CH_2-CH_2-CH=CH-$, and $-CH_2-C\equiv C-CH_2-$.

Examples of branched partially unsaturated $C_{3-12}$ alkylene groups ($C_{3-12}$ alkenylene and alkynylene groups) include, but are not limited to, $-C(CH_3)=CH-$, $-C(CH_3)=CH-CH_2-$, $-CH=CH-CH(CH_3)-$ and $-C\equiv C-CH(CH_3)-$.

Examples of alicyclic saturated $C_{3-12}$ alkylene groups ($C_{3-12}$ cycloalkylenes) include, but are not limited to, cyclopentylene (e.g. cyclopent-1,3-ylene), and cyclohexylene (e.g. cyclohex-1,4-ylene).

Examples of alicyclic partially unsaturated $C_{3-12}$ alkylene groups ($C_{3-12}$ cycloalkylenes) include, but are not limited to, cyclopentenylene (e.g. 4-cyclopenten-1,3-ylene), and cyclohexenylene (e.g. 2-cyclohexen-1,4-ylene; 3-cyclohexen-1,2-ylene; 2,5-cyclohexadien-1,4-ylene).

Includes Other Forms

Unless otherwise specified, included in the above are the well known ionic, salt, solvate, and protected forms of these substituents. For example, a reference to carboxylic acid ($-COOH$) also includes the anionic (carboxylate) form ($-COO^-$), a salt or solvate thereof, as well as conventional protected forms. Similarly, a reference to an amino group includes the protonated form ($-N^+HR^1R^2$), a salt or solvate of the amino group, for example, a hydrochloride salt, as well as conventional protected forms of an amino group. Similarly, a reference to a hydroxyl group also includes the anionic form (—O⁻), a salt or solvate thereof, as well as conventional protected forms.

Isomers, Salts and Solvates

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Preferably compounds of formula VI have the following stereochemistry at the C11 position:

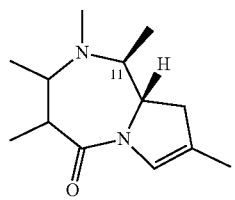

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH₃, is not to be construed as a reference to its structural isomer, a hydroxymethyl group, —CH₂OH. Similarly, a reference to ortho-chlorophenyl is not to be construed as a reference to its structural isomer, meta-chlorophenyl. However, a reference to a class of structures may well include structurally isomeric forms falling within that class (e.g. $C_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

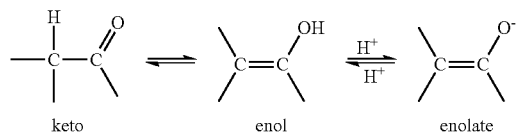

Note that specifically included in the term "isomer" are compounds with one or more isotopic substitutions. For example, H may be in any isotopic form, including ¹H, ²H (D), and ³H (T); C may be in any isotopic form, including ¹²C, ¹³C, and ¹⁴C; O may be in any isotopic form, including ¹⁶O and ¹⁸O; and the like.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below.

It may be convenient or desirable to prepare, purify, and/or handle a corresponding salt of the active compound, for example, a pharmaceutically-acceptable salt. Examples of pharmaceutically acceptable salts are discussed in Berge, et al., *J. Pharm. Sci.*, 66, 1-19 (1977).

For example, if the compound is anionic, or has a functional group which may be anionic (e.g. —COOH may be —COM, then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations such as $Al^{+3}$. Examples of suitable organic cations include, but are not limited to, ammonium ion (i.e. $NH_4^+$) and substituted ammonium ions (e.g. $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group which may be cationic (e.g. —$NH_2$ may be —$NH_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

General Synthetic Routes

Compounds of formula II:

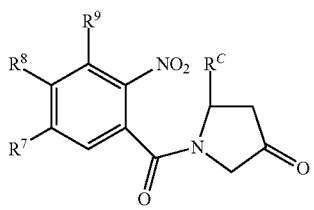

II can be synthesised from compounds of formula A:

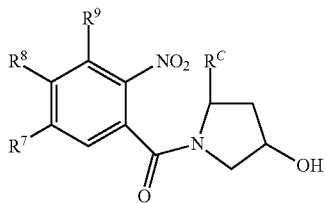

A by oxidation for example using: TCCA and TEMPO; BAIB and TEMPO; TPAP; Dess-Martin conditions; or Swern conditions.

Compounds of formula A may be synthesised by coupling appropriate compounds of formulae B and C, or activated derivatives thereof:

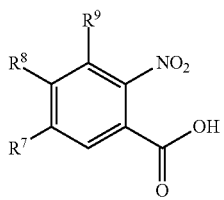

B

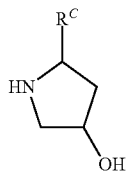

C

Compound of formulae B and C are generally commercially available or readily synthesisable.

If compound B is a dimer, then this may be synthesised as described in WO 00/12508.

Further Embodiments

The following further embodiments may be combined with each other as appropriate.

$R^7$ $R^7$ is selected from: $OR^A$, where $R^A$ is selected from $C_{1-4}$ saturated alkyl, optionally substituted by phenyl, which phenyl may bear a chloro substituent, pyridyl and furanyl; chloro; $NH_2$; and $-CH_2-O-C(=O)Me$; or $R^7$ and $R^9$ together form a group $-O-(CH_2)_m-O-$, where m is 1 or 2.

In some embodiments, $R^4$ may be $OR^A$, where $R^A$ is selected from $C_{1-4}$ saturated alkyl, optionally substituted by phenyl, pyridyl and furanyl.

In some of these embodiments, $R^A$ is unsubstituted $C_{1-4}$ saturated alkyl, i.e. methyl, ethyl, propyl and butyl. It may be preferred that $R^A$ is methyl.

In other of these embodiments, $R^A$ is $C_{1-4}$ saturated alkyl substituted by a group selected from phenyl, pyridyl and furanyl. It may be preferred that the substituent is phenyl. It may be further preferred that $R^A$ is phenyl-methyl (i.e. benzyl).

$R^8$ $R^8$ is $OProt^O$, and $Prot^O$ is a silicon-based oxygen protecting group, such that $R^D$ is orthogonal to $Prot^O$. Preferred $Prot^O$ groups include TIPS and TBS.

$R^9$ $R^9$ is selected from H, methyl and methoxy. In some embodiments, $R^9$ is hydrogen.

$R^S$ $R^S$ is selected from $CF_3$, $CH_3$ and

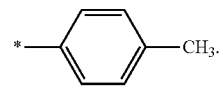 [SMILES: *c1ccc(C)cc1]

When $R^S$ is $CF_3$, the C2 group is triflate.
When $R^S$ is $CH_3$, the C2 group is mesylate.
When $R^S$ is

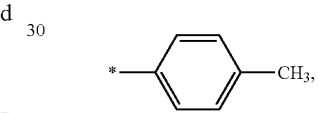

the C2 group is tosylate.

When $R^S$ is $(CF_2)_3CF_3$, the C2 group is nonaflate.

In some embodiments, $R^S$ is preferably $CF_3$.

$R^C$ $R^C$ is selected from:

(i) $-C(=O)-OR^{C1}$, where $R^{C1}$ is a saturated $C_{1-4}$ alkyl group;

(ii) $-CH_2-O-C(=O)R^{C2}$, where $R^{C2}$ is methyl or phenyl;

(iii) $-CH_2-O-Si-(R^{Si1})(R^{Si2})(R^{Si3})$, where $R^{Si1}$, $R^{Si2}$, $R^{Si3}$ are independently selected from $C_{1-6}$ a saturated alkyl group and a phenyl group; and (iv) $C(-YR^{C3})(-YR^{C4})$ where each Y is independently O or S, and where $R^{C3}$ and $R^{C4}$ are independently a saturated $C_{1-4}$ alkyl group, or together form a $C_{2-3}$ alkylene.

$R^{C1}$ is a saturated $C_{1-4}$ alkyl group, i.e. methyl, ethyl, propyl and butyl. In some embodiments, $R^{C1}$ is preferably methyl or ethyl, and more preferably methyl.

When $R^{C2}$ is methyl, $R^C$ comprises an acetate group. When $R^{C2}$ is phenyl, $R^C$ comprises a benzoate group. In some embodiments, it is preferred $R^{C2}$ is methyl.

$-Si-(R^{Si1})(R^{Si2})(R^{Si3})$ is a silyl protecting group, which are well known in the art. Groups of particular interest in the present invention are:

| | |
|---|---|
| TMS | $-Si(CH_3)_3$ |
| TES | $-Si(C_2H_5)_3$ |
| TIPS | $-Si(i-Pr)_3$ |
| TBDMS | $-Si(CH_3)_2(t-Bu)$ |
| IPDMS | $-Si(CH_3)_2(i-Pr)$ |
| DEIPS | $-Si(C_2H_5)_2(i-Pr)$ |
| TBDPS | $-Si(Ph)_2(t-Bu)$ |

In some embodiments, preferred silyl protecting groups are TBDMS and TBDPS, or which TBDMS is more preferred.

$R^{C3}$ may be a saturated $C_{1-4}$ alkyl group, i.e. methyl, ethyl, propyl and butyl. In some embodiments, $R^{C3}$ is preferably methyl or ethyl, and more preferably methyl.

$R^{C4}$ may be a saturated $O_{1-4}$ alkyl group, i.e. methyl, ethyl, propyl and butyl. In some embodiments, $R^{C4}$ is preferably methyl or ethyl, and more preferably methyl.

When $R^{C3}$ and $R^{C4}$ together form a $C_{2-3}$ alkylene group, $R^C$ is selected from:

In some embodiments, Y is O. In other embodiments, Y is S.

In some embodiments, it is preferred that $R^C$ is —Si—$(R^{Si1})(R^{Si2})(R^{Si3})$.

Second Aspect

In the method of the second aspect, the compound of formula II is treated with the appropriate anhydride and anhydrous 2,6-lutidine or anhydrous 2,6-$^t$Bu-pyridine at a temperature of −35° C. or lower in a dry organic solvent under a inert atmosphere.

Therefore, if the compound of formula I has a triflate group at C2, then the compound of formula II is treated with triflic anhydride. If the compound of formula I has a mesylate group at C2, then the compound of formula II is treated with mesyl anhydride. If the compound of formula I has a tosylate group at C2, then the compound of formula II is treated with tosyl anhydride. If the compound of formula I has a nonaflate group at C2, then the compound of formula II is treated with nonafluorobutane sulphonic anhydride.

The base may be 2,6-lutidine or 2,6-$^t$Bu-pyridine. It may be preferred that the base is 2-6-lutidine.

The reaction may be carried out at a temperature of −35° C. or lower. In some embodiments, the reaction is carried out at a temperature of −40° C., −45° C., or −50° C. In further embodiments, the reaction is carried out at −78° C.

A $R^2$ is selected from:
(i) an optionally substituted $C_{5-20}$ aryl group;
(ii) an optionally substituted $C_{1-5}$ alkyl group (including a $C_{2-5}$ alkenyl group and a $C_{2-5}$ alkynyl group); and
(iii) H.

In some embodiments, $R^2$ is an optionally substituted $C_{5-20}$ aryl group.

In some of these embodiments, $R^2$ is preferably an optionally substituted $C_{5-7}$ aryl group, and most preferably an optionally substituted phenyl group.

In other of these embodiments, $R^2$ is a $C_{9-12}$ aryl group, for example naphth-1-yl or naphth-2-yl, preferably naphty-2-yl Further examples of $C_{9-12}$ aryl groups include quinolinyl, for example, quinolin-2-yl, quinolin-3-yl and quinolin-6-yl.

In other of these embodiments, $R^2$ is a $C_{5-7}$ heteroaryl group, for example furanyl, thiophenyl and pyridyl. Of these thiophenyl is preferred, for example, thiophen-2-yl and thiophen-3-yl.

The $C_{5-20}$ aryl group may bear any substituent group. It preferably bears from 1 to 3 substituent groups, with 1 and 2 being more preferred, and singly substituted groups being most preferred.

Preferred $C_{5-20}$ aryl substituents, particularly for phenyl, include: halo (e.g. F, Cl, Br); $C_{1-7}$ alkoxy (e.g. methoxy, ethoxy); di-$C_{1-4}$ alkylamino-$C_{1-7}$ alkoxy; $C_{1-7}$ alkyl (e.g. methyl, trifluoromethyl, ethyl, propyl, t-butyl); bis-oxy-alkylene (e.g. bis-oxy-methylene, —O—$CH_2$—O—); and N—$C_{1-4}$ alkyl piperazinyl.

Particularly preferred substituted $C_{5-20}$ aryl groups include, but are not limited to, 4-methylphenyl, 4-methoxyphenyl, 3-methoxyphenyl, 4-fluoro-phenyl, 3,4-bisoxymethylene-phenyl, 4-trifluoromethylphenyl, 4-methylthiophenyl, 4-cyanophenyl, 4-phenoxyphenyl, 4-N-methyl piperazinyl phenyl, 4-N,N-dimethyl amino propoxyphenyl, 4-N,N-dimethyl amino ethoxyphenyl, 6-methoxynaphth-2-yl, and 6-ethoxynaphth-2-yl.

Particularly preferred unsubstituted $C_{5-20}$ aryl groups include, but are not limited to thiophen-2-yl, napth-2-yl, quinolin-3-yl and quinolin-6-yl.

The aryl groups can be installed with the appropriate boronic acid (or pinacol ester) at 0° C. using tetrakis palladium triphenylphosphine as catalyst and sodium carbonate as base. Hindered or electron deficient boronic acids may require heating to 60° C., if higher temperatures or prolonged heating is required triethylamine is preferred to sodium carbonate as base.

In some embodiments, $R^2$ is an optionally substituted $C_{1-5}$ alkyl group (including a $C_{2-5}$ alkenyl group and a $C_{2-5}$ alkynyl group).

In some of these embodiments, $R^2$ is an optionally substituted $C_{1-5}$ (saturated) alkyl group (e.g. methyl, ethyl, propyl, butyl, pentyl), which may be cyclic (e.g. cyclopropyl, cyclobutyl, cyclopentyl). Preferred groups may include methyl, ethyl and propyl, as well as cyclopropyl.

In others of these embodiments, $R^2$ is an optionally substituted $C_{2-5}$ alkenyl group, which may be cyclic. The group may be fully unsaturated or partially unsaturated, and therefore may include ethenyl (—CH═$CH_2$), propenyl (e.g. —CH═CH—$CH_3$, —$CH_2$—CH═$CH_2$, —C(═$CH_2$)—$CH_3$), butenyl (e.g. —CH═CH—$CH_2$—$CH_3$, —$CH_2$—CH═CH—$CH_3$, —$CH_2$—$CH_2$—CH═$CH_2$, —C(═$CH_2$)—$CH_2$—$CH_3$), butadienyl (e.g. —CH═CH—CH═$CH_2$, —C(═$CH_2$)—CH═$CH_2$), pentenyl (e.g. —CH═CH—$CH_2$—$CH_2$—$CH_3$, —$CH_2$—CH═CH—$CH_2$—$CH_3$, —$CH_2$—$CH_2$—CH═CH—$CH_3$, —$CH_2$—$CH_2$—$CH_2$—CH═$CH_2$, —C(═$CH_2$)—$CH_2$—$CH_2$—$CH_3$), pentadienyl (e.g. —CH═CH—CH═CH—$CH_3$, —$CH_2$—CH═CH—CH═$CH_2$, —C(═$CH_2$)—CH═CH—$CH_3$) and cyclopentenyl.

In others of these embodiments, $R^2$ is an optionally substituted $O_{2-5}$ alkynyl group. The group may be fully unsaturated or partially unsaturated, and therefore may include ethynyl (—C≡CH), propynyl (e.g. —C≡C—$CH_3$, —$CH_2$—C≡CH), butynyl (e.g. —C≡C—$CH_2$—$CH_3$, —$CH_2$—C≡C—$CH_3$, —$CH_2$—$CH_2$—C≡CH), pentynyl (e.g. —C≡C—$CH_2$—$CH_2$—$CH_3$, —$CH_2$—C≡C—$CH_2$—$CH_3$, —$CH_2$—$CH_2$—C≡C—$CH_3$, —$CH_2$—$CH_2$—$CH_2$—C≡CH), and cyclopentynyl.

For groups above that contain unsaturation, at least one of the unsaturated bonds may be conjugated to the double bond present between C2 and C3 in the PBD's C-ring. It may be the case that all the unsaturated bonds are conjugated.

The optional substitutents for the optionally substituted $C_{1-5}$ alkyl groups (including $C_{2-5}$ alkenyl group and $C_{2-5}$ alkynyl groups), may include, in particular:
(i) $C_{5-20}$ aryl groups, which themselves may be substituted as discussed above for $R^2$ groups in themselves;
(ii) cyano (—CN);
(iii) amido (—C(═O)—$NR^1R^2$);

(iv) ester (—C(═O)—OR).
(v) —OR;
(vi) boronic groups suitable for coupling a further group, such as:

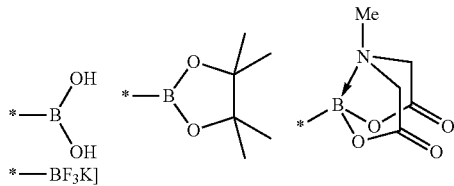

(vii) tin groups, suitable for coupling a further group, such as —Sn(R)$_3$ where R is a C$_{1-7}$ alkyl group.

The amido group is as defined above. In some embodiments, the amino substituents may preferably be selected from C$_{1-7}$ alkyl or more preferably C$_{1-4}$ alkyl, such that the amido group is, for example, —C(═O)NH$_2$, —C(═O)NHCH$_3$, —C(═O)N(CH$_3$)$_2$, —C(═O)NHCH$_2$CH$_3$, and —C(═O)N(CH$_2$CH$_3$)$_2$ The ester group is as defined above. In some embodiments, the ester substituent is a C$_{1-7}$ alkyl group or a C$_{1-4}$ alkyl group, such that the ester group is, for example, —C(═O)OCH$_3$, —C(═O)OCH$_2$CH$_3$ and —C(═O)OC(CH$_3$)$_3$.

The ether group is as defined above. In some embodiments, the ether substituent is a C$_{1-7}$ alkyl group or a C$_{1-4}$ alkyl group, such that the ether group is, for example, —OCH$_3$, —OCH$_2$CH$_3$ and —OC(CH$_3$)$_3$.

In some embodiments, R$^2$ is H.

R$^2$ groups of particular interest include:

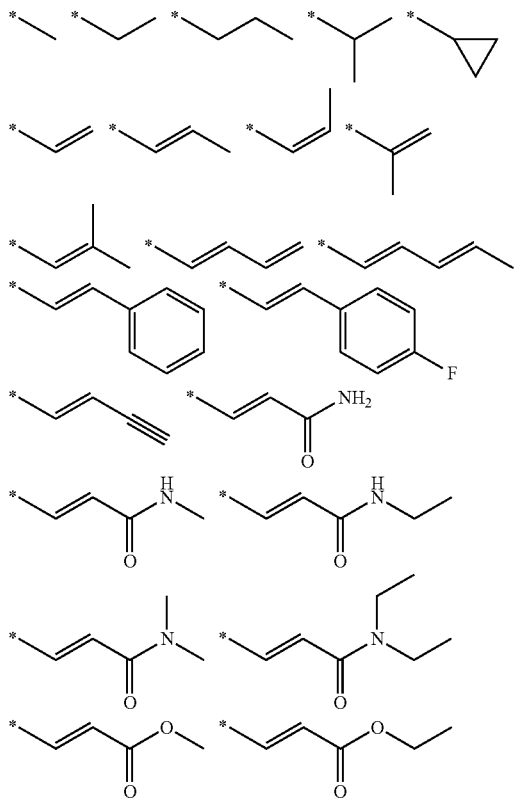

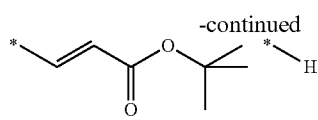

B

If R$^C$ is —CH$_2$—O—C(═O)R$^{C2}$ or —CH$_2$—O—Si—(R$^{Si1}$)(R$^{Si2}$)(R$^{Si3}$) then the conversion of III to IV is by reduction of the nitro group. If R$^C$ is —CH$_2$—O—C(═O)R$^{C2}$, this reduction is carried out by using zinc in acetic acid. Alternatives include Cd/Pb couple, sodium dithionite or tin II chloride. If Rc is —CH$_2$—O—Si—(R$^{Si1}$)(R$^{Si2}$)(R$^{Si3}$), then this reduction is carried out using zinc in a weak acid, e.g. 5% formic acid in ethanol. If Rc is —C(—YR$^{C3}$)(—YR$^{C4}$), this reduction may be carried out using Cd/Pb couple, sodium dithionite or tin II chloride.

If R$^C$ is —C(═O)—OR$^{C1}$, then the conversion of III to IV is achieved by first reducing of the ester and reprotection as an acetate or silyl ether. The reduction can be achieved by standard means, for example with LiBH$_4$, or LiEt$_3$BH$_4$. Reprotection as an acetate can be achieved, for example, by reaction with acetyl chloride; reprotection as a benzoate can be achieved, for example, by reaction with benzoyl chloride; reprotection as a silyl ether can be achieved, for example, by reaction with the appropriate silyl chloride in DMF in the presence of imidazole.

C

R$^{10}$ is a carbamate-based nitrogen protecting group, which is palladium-labile, or contains a moiety which is palladium-labile.

If R$^{10}$ is a simple nitrogen protecting group, it may be preferably selected from a group containing the moiety:

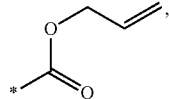 [SMILES: *C(=O)OCC=C]

such as Alloc, Ipaoc, Coc, Noc, Paloc, and may more preferably be Alloc.

If R$^{10}$ is a complex nitrogen protecting group, it may be preferably a group which is cathepsin labile.

The nitrogen protecting group is preferably introduced by reaction of IV with triphosgene to obtain the isocyanate followed by reaction with R$^{10}$—OH. The reaction of IV with triphosgene should be carried in an anhydrous and non-hydroxylic organic solvent, which is preferably non-polar. Suitable solvents include anhydrous dichloromethane and anhydrous toluene. The reaction may be carried out at room temperature. The subsequent reaction with R$^{10}$—OH should be carried in an anhydrous and non-hydroxylic organic solvent, which is preferably non-polar. Suitable solvents include anhydrous dichloromethane and anhydrous toluene. The reaction should be carried out in the presence of a base is present, and suitable bases include pyridine or TEA. The reaction may be carried out at 0° C., or at a higher temperature to increase the rate of reaction.

D

The PBD B-ring is preferably closed using Dess-Martin periodinane.

E)

R$^E$ is selected from: O—C$_{1-2}$ alkyl; O—Si—(R$^{Si1}$)(R$^{Si2}$)(R$^{Si3}$) where R$^{Si1}$, R$^{Si2}$, R$^{Si3}$ are as defined above; O—CH$_2$OCH$_3$ (OMOM), O—CH$_2$OC$_2$H$_4$OCH$_3$ (OMEM), $OC_5H_{10}$ (THP). Furthermore, $Prot^O$ needs to be orthogonal to $R^E$. When $R^E$ is $O$—Si—$(R^{Si1})(R^{Si2})(R_{Si3})$, Si—$(R^{Si1})(R_{Si2})$ $(R^{Si3})$ is a silicon-based oxygen protecting group as described above. In these embodiments, $R^E$ may preferably be O-TBS.

G

In some embodiments. Hal and Q are the same, such that the compound of formula X is symmetrical. It is preferred that Hal is preferably I. It is also preferred that Q is I. Thus, in some embodiments, it is preferred that both Hal and Q are I.

In some embodiments about 3 equivalents of formula X are used relative to the compound of formula VIII.

H

The preferences expressed are applicable to this aspect of the invention.

Orthogonal Protecting Groups

In some embodiments of the present invention, $R^D$ is TBS and $Prot^O$ is TIPS.

In other embodiments, $R^D$ is OAc and $Prot^O$ is either TIPS or TBS.

In some embodiments of the present invention, $Prot^O$ is TIPS and $R^E$ is OTBS.

In other embodiments of the present invention, $Prot^O$ is TIPS and $R^E$ is OMe, OMEM, THP or OMOM.

In further embodiments of the present invention, $Prot^O$ is TBS, and $R^E$ is OMe, OMEM, THP or OMOM.

In particularly preferred embodiments of the present invention, $R^D$ is TBS, $Prot^O$ is TIPS and $R^E$ is TBS.

EXAMPLES

General Information

Reaction progress was monitored by thin-layer chromatography (TLC) using Merck Kieselgel 60 F254 silica gel, with fluorescent indicator on aluminium plates. Visualisation of TLC was achieved with UV light or iodine vapour unless otherwise stated. Flash chromatography was performed using Merck Kieselgel 60 F254 silica gel. Extraction and chromatography solvents were bought and used without further purification from Fisher Scientific, U.K. All chemicals were purchased from Aldrich, Lancaster or BDH.

The LC/MS conditions were as follows: Method 1 (default when not specified) The HPLC (Waters Alliance 2695) was run using a mobile phase of water (A) (formic acid 0.1%) and acetonitrile (B) (formic acid 0.1%). Gradient: initial composition 5% B over 1.0 min then 5% B to 95% B within 3 min. The composition was held for 0.5 min at 95% B, and then returned to 5% B in 0.3 minutes. Total gradient run time equals 5 min. Flow rate 3.0 mL/min, 400 μL was split via a zero dead volume tee piece which passes into the mass spectrometer. Wavelength detection range: 220 to 400 nm. Function type: diode array (535 scans). Column: Phenomenex® Onyx Monolithic C18 50×4.60 mm.

Method 2: The HPLC (Waters Alliance 2695) was run using a mobile phase of water (A) (formic acid 0.1%) and acetonitrile (B) (formic acid 0.1%). Gradient: initial composition 5% B over 1.0 min then 5% B to 95% B over 2.5 minute period. The composition was held for 0.5 min at 95% B, and then returned to 5% B in 0.1 minutes and held there for 0.9 minutes. Total gradient run time equals 5 min. Flow rate 3.0 mL/min, 400 μL was split via a zero dead volume tee piece which passes into the mass spectrometer. Wavelength detection range: 220 to 400 nm. Function type: diode array (535 scans). Column: Phenomenex® Onyx Monolithic C18 50×4.60 mm.

Example 1

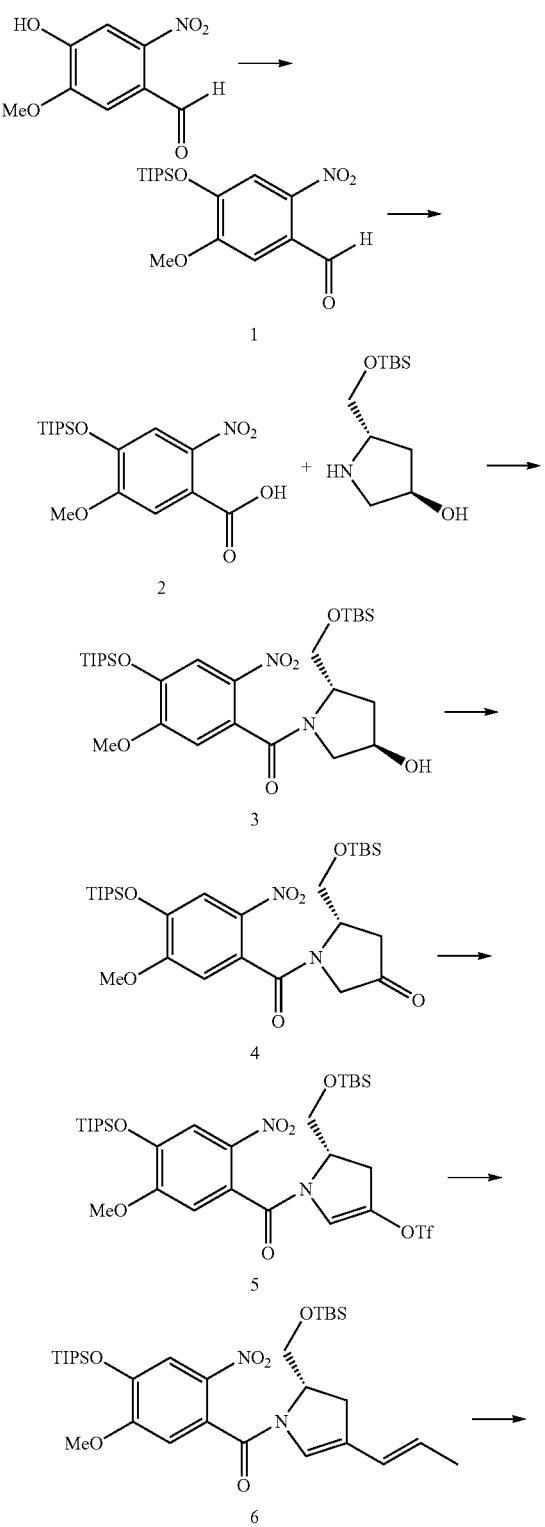

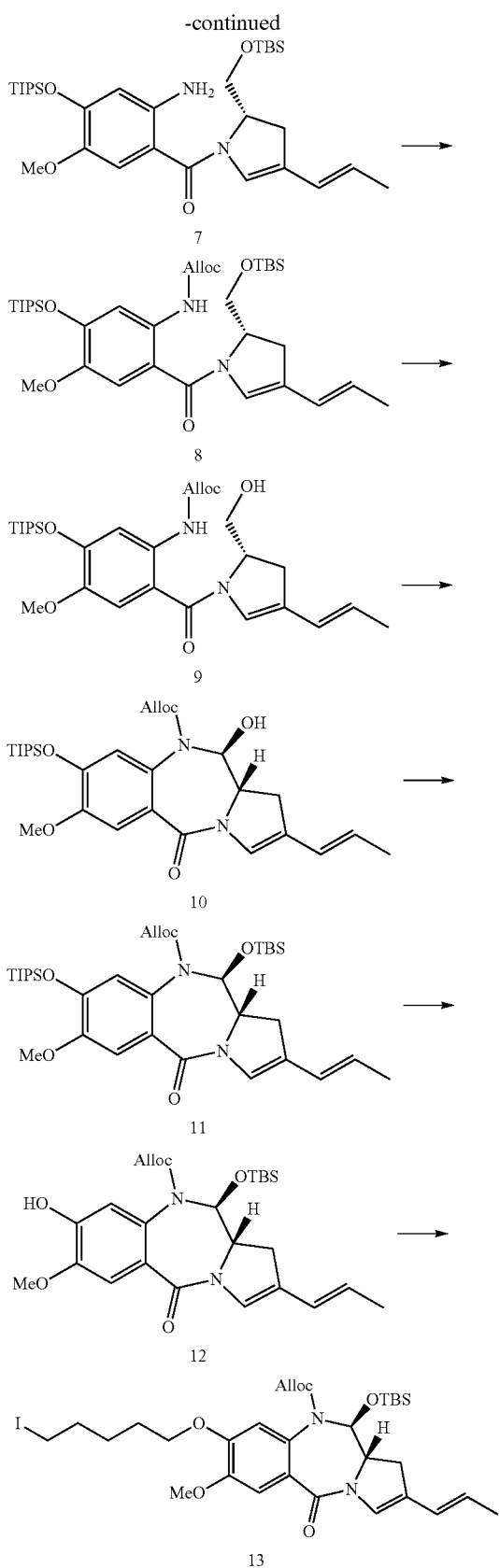

The synthesis of the starting material is described in JP 2008050321A.

(a) Compound 1

Neat triisopropylsilylchloride (86 mL) was added to a mixture of imidazole (54.7 g) and phenol (4 g) (ground together). The mixture was heated until the phenol and imidazole melted and went into solution (110° C.). The reaction mixture was allowed to stir for 5 minutes and was then allowed to cool, whereupon a solid was observed to form at the bottom of the flask. The reaction mixture was loaded directly on to silica gel and the silica pad was washed with hexane. The desired product was eluted with 5% ethyl acetate in hexane. Excess eluent was removed by rotary evaporation under reduced pressure to afford a quantitative amount of the product 1 (112.454 g, >100%). LCMS RT 4.25 mins, m/z ES$^+$ 353.85

(b) Compound 2

A solution of sodium chlorite (60.6 g) and sodium dihydrogenphosphate (53.2 g) (NaH$_2$PO$_4$) in water (800 mL) was added to a solution of compound 1 (112.4 g) in tetrahydrofuran (500 mL) at room temperature. Hydrogen peroxide (60% w/w, 179.02 mL) was immediately added to the vigorously stirred biphasic mixture. The reaction was initiated by addition of 1M hydrochloric acid to lower the pH of the reaction mixture to between 5 and 6. The reaction mixture evolved gas (oxygen), the starting material dissolved and the temperature of the reaction mixture rose to 40° C. As the reaction proceeded the pH continued to drop and was kept between 5 and 6 by addition of solid sodium dihydrogenphosphate (12 g). After 1 hour LC/MS revealed that the reaction was complete. The reaction mixture was cooled in an ice bath and hydrochloric acid (1 M) was added to lower the pH to between 1 and 2. The reaction mixture was then extracted with ethyl acetate (1 L) and the organic phases washed with brine (2×100 mL) and dried over magnesium sulphate. The organic phase was filtered and excess solvent removed by rotary evaporation under reduced pressure to afford the product 2 in quantitative yield. LC/MS 3.93 mins, m/z ES$^-$ 367.74

(c) Compound 3

A solution of acid 2 (58.60 g), hydroxybenzotriazole (26.59 g) and DCC (39.12 g) in dichloromethane (200 mL) was allowed to stir for 30 mins at which time a solution of C-ring (36.70 g) and triethylamine (33 mL) in dichloromethane (100 mL) was added at 0° C. under argon. The coupling reaction proceeded rapidly and went to completion inside 1 hour, as monitored by LC/MS. The reaction mixture was filtered and diluted with dichloromethane (150 mL). The organic phase was washed sequentially with cold dilute hydrochloric acid (0.1 M), saturated aqueous sodium bicarbonate and brine. The organic layer was dried over magnesium sulphate, filtered and excess solvent removed by rotary evaporation under reduced pressure. The residue was subjected to column flash chromatography (silica gel; gradient 40% ethyl acetate in hexane to 80% ethyl acetate in hexane). Excess solvent was removed by rotary evaporation under reduced pressure. A white solid was observed in the resulting residue which was removed by dissolving the residue up in diethyl ether. Removal of diethyl ether by rotary evaporation under reduced pressure afforded the pure product 3, (38.80 g, 42% yield). LC/MS 4.43 mins, m/z ES$^+$ 582.92

(d) Compound 4

TCCA (8.82 g) was added to a stirred solution of 3 (31.67 g) and TEMPO (0.85 g) in dry dichloromethane (250 mL) at 0° C. The reaction mixture was vigorously stirred for 20 minutes at room temperature, at which point TLC (50/50 ethyl acetate/hexane) revealed complete consumption of the starting material. The reaction mixture was filtered through celite and the filtrate washed with aqueous saturated sodium bicarbonate (100 mL), sodium thiosulphate (9 g in 300 mL), brine (100 mL) and dried over magnesium sulphate. Rotary evaporation under reduced pressure afforded product 4 in quantitative yield. LC/MS 4.52 mins, m/z ES+ 581.08

(e) Compound 5

Triflic anhydride (27.7 mL) was injected in one portion to a vigorously stirred suspension of compound 4 (31.86 g) in dry dichloromethane (900 mL) in the presence of 2,6-lutidine (25.6 mL, dried over sieves) at −50° C. (acetone/dry ice bath). The reaction mixture was allowed to stir for 1.5 hours when LC-MS following a mini work-up (water/dichloromethane) revealed the reaction to be complete. Water was added to the still cold reaction mixture and the organic layer was separated and washed with saturated sodium bicarbonate, brine and magnesium sulphate. The organic phase was filtered and excess solvent was removed by rotary evaporation under reduced pressure. The residue was subjected to column flash chromatography (silica gel; 10% ethyl acetate in hexane), removal of excess eluent afforded the product 5 (45.50 g, 96% yield)

LC/MS RT 4.32 mins, m/z ES− 712.89

(f) Compound 6

Tetrakis(triphenylphosphine)palladium(0) (1.14 g) was added to triflate 5 (23.40 g), E 2-propenylboronic acid (4.05 g) and potassium phosphate tribasic (13.93 g) in a mixture of dry dioxane (100 mL) under an argon atmosphere. The solution turned black and the reaction went rapidly to completion after 30 minutes as monitored by LC/MS. The reaction mixture was partitioned between ethyl acetate and water and the organic layer was washed with brine and dried over magnesium sulphate. The organic phase was filtered and excess solvent was removed by rotary evaporation under reduced pressure. The resulting residue was subjected to column flash chromatography (silica gel; 5% ethyl acetate/10% hexane). Pure fractions were collected and combined, and excess eluent was removed by rotary evaporation under reduced pressure afforded the product 6 (30.5 g, 82% yield).

LC/MS 4.43 mins, m/z ES+ 605.11.

(f) Compound 7

Zinc powder (106 g) was added to a solution of compound 6 (27.06 g) in 5% formic acid in ethanol (270 mL). The resulting exotherm was controlled using an ice bath to maintain the temperature of the reaction mixture at 20° C. After 20 minutes the reaction mixture was filtered through celite. The filtrate was diluted with ethyl acetate and the organic phase was washed with water, saturated aqueous sodium bicarbonate and brine. The organic phase was dried over magnesium sulphate, filtered and excess solvent removed by rotary evaporation under reduced pressure. The resulting residue was subjected to column flash chromatography (silica gel; 10% ethyl acetate in hexane). Pure fractions were collected and combined and excess was removed by rotary evaporation under reduced pressure to afford the product 7 (14.63 g, 48% yield). LC/MS RT 4.42 mins (g) Compound 8

Allyl chloroformate (1.75 mL) was added to a solution of amine 7 (8.602 g) in the presence of dry pyridine (2.66 g) in dry dichloromethane (200 mL) at −78° C. (acetone/dry ice bath). After addition was complete the bath was removed and the reaction mixture was allowed to warm to room temperature. The reaction mixture was washed sequentially with dilute hydrochloric acid (0.01 N), saturated aqueous sodium bicarbonate and brine. The organic phase was dried over magnesium sulphate, filtered and excess solvent removed by rotary evaporation under reduced pressure to afford the product 8 which was used directly in the next reaction.

LC/MS RT 4.08 mins (h) Compound 9

The crude 8 was dissolved in a 3/1/1 mixture of acetic acid/water/tetrahydrofuran (30/10/10 mL) and allowed to stir at room temperature. Deprotection was slower than expected so a mixture of methanol/acetic acid/water (30/30/30 mL) was added causing the reaction to proceed faster. After 6 hours the reaction was found to be 90% complete, to avoid acidic degradation the reaction mixture was stored at −20° C. in a spark free freezer overnight. The reaction was continued at room temperature the following day until all the starting material had been consumed. The reaction mixture was diluted with ethyl acetate and washed sequentially with water (2×500 mL), saturated aqueous sodium bicarbonate (200 mL) and brine. The organic phase was dried over magnesium sulphate filtered and excess ethyl acetate removed by rotary evaporation under reduced pressure. The resulting residue was subjected to column flash chromatography (silica gel, gradient; 40/60 to 50/50 ethyl acetate in hexane). Pure fractions were collected and combined and excess eluent was removed by rotary evaporation under reduced pressure to afford the desired product 9 (1 g, 70%).

(i) Compound 10

Dimethyl sulphoxide (1.75 mL) was injected into an oven dried sealed microwave vial containing a solution of oxalyl chloride (1 mL) in dry dichloromethane (50 mL) at −78° C. (dry ice/acetone bath) under an atmosphere of argon. After 15 minutes a solution of 9 (5.36 g) in dry dichloromethane (40 mL) was added slowly with the temperature still at −78° C. After 15 mins triethylamine (6.87 mL, dried over 4 Å molecular sieves) was injected and the dry ice/acetone bath was removed. The reaction mixture was allowed to reach room temperature and was extracted with cold hydrochloric acid (0.1 M), saturated aqueous sodium bicarbonate and brine. The organic phase was dried over magnesium sulphate, filtered and excess dichloromethane was removed by rotary evaporation under reduced pressure to afford product 10 in a quantitative yield. LC/MS $R_T$ 3.68 mins, m/z ES+ 543.03.

(j) Compound 11

Tert-butyldimethylsilyltriflate (4.713 mL) was added to a solution of compound 10 (3.713 g) and 2,6-lutidine (3.187 mL) in dry dichloromethane (40 mL) and cooled to 0° C. under argon. After 1 hour, the reaction mixture was extracted with water, saturated aqueous sodium bicarbonate and brine. The organic phase was dried over magnesium sulphate, filtered and excess was removed by rotary evaporation under reduced pressure. The resulting residue was subjected to column flash chromatography (silica gel; gradient, 5% ethyl acetate in hexane to 20% ethyl acetate in hexane). Pure fractions were collected and combined and excess eluent was removed by rotary evaporation under reduced pressure to give the product 11 (3.05 g, 68% yield). LC/MS RT 4.05 mins, ES+ 657.16.

(k) Compound 12

Lithium acetate (0.47 g) was added to a solution of compound 11 (3.05 g) in wet dimethylformamide (30 mL, 50;1 DMF/water). After 1 and three-quarter hours the reaction was observed to be complete and the reaction mixture was diluted with ethyl acetate and washed with citric acid, water (0.6 mL) and brine. The organic layer was dried over magnesium sulphate filtered and excess ethyl acetate was removed by rotary evaporation under reduced pressure. The resulting residue was subjected to column flash chromatography (silica gel; gradient, 25% ethyl acetate to 75% ethyl acetate in hexane). Pure fractions were collected and combined and excess eluent was removed by rotary evaporation under reduced pressure to give the product 12 (2.12 g, 91% yield). LC/MS RT 3.55 mins, ES+ 501.12.

(l) Compound 13

Diiodopentane (377 μL) was added to a solution of compound 12 (254 mg) in acetone (2 mL) over potassium carbonate (70 mg) under an argon atmosphere. The reaction mixture was heated at 60° C. for 2 hours at which time TLC indicated that the reaction was complete. Excess acetone was removed by rotary evaporation under reduced pressure. The residue (including inorganics) was subjected to column flash chromatography (silica gel; gradient 20% ethyl acetate in hexane to 33% ethyl acetate in hexane). Pure fractions were collected and combined and removal of excess eluent by rotary evaporation under reduced pressure afforded the product 13 (282 mg, 80% yield). LC/MS RT 4.03 mins, m/z ES+ 696.73

Example 2

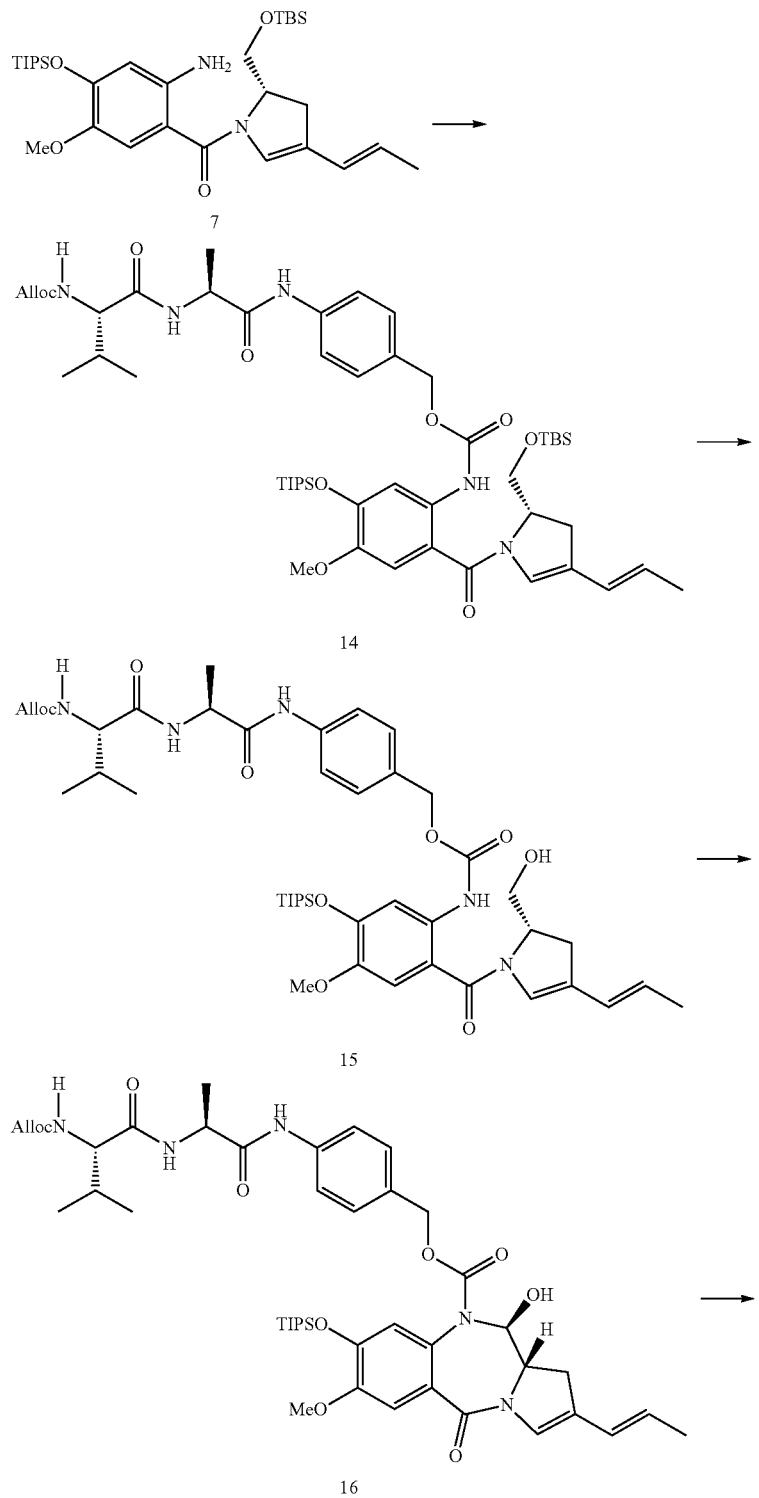

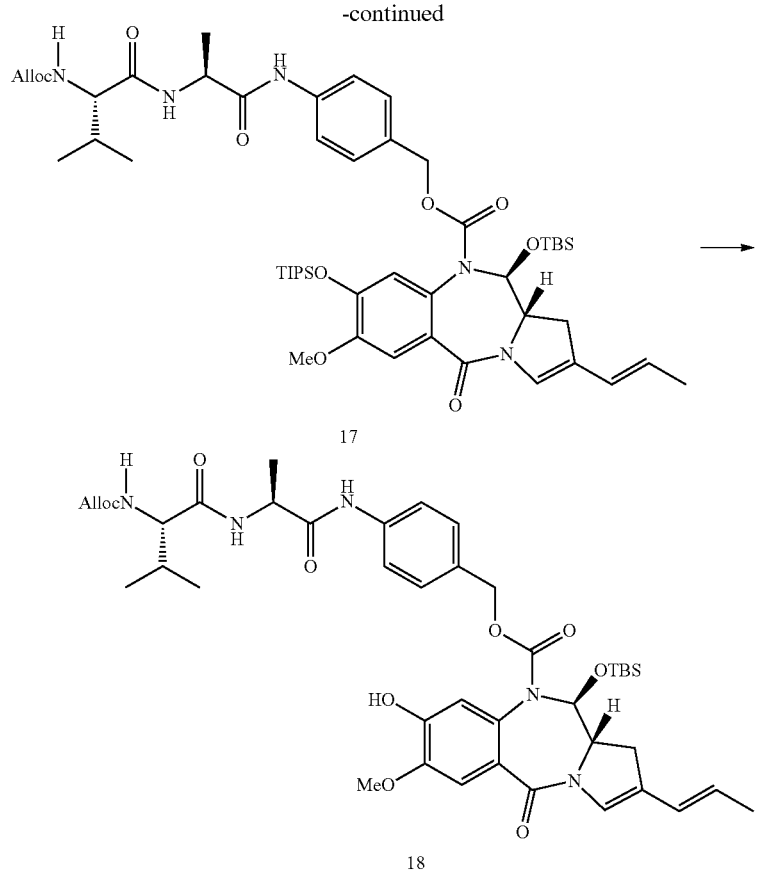

17

18

(a) Compound 14

Triethylamine (0.745 mL) was added to a stirred solution of the amine 7 (1.4 g) and triphosgene 260 mg) in dry tetrahydrofuran (30 mL) at 5° C. (ice bath). The progress of the isocyanate reaction was monitored by periodically removing aliquot from the reaction mixture quenching with methanol and performing LC/MS analysis. Once the isocyanate formation was complete a solution of the alloc-Val-Ala-PABOH (1.38 g) and triethylamine (0.5 mL) in dry tetrahydrofuran (50 mL) was rapidly added by injection to the freshly prepare isocyanate. The reaction mixture was allowed to stir at 30° C. overnight. Excess solvent was removed by rotary evaporation under reduced pressure and the residue absorbed onto silica gel and dry loaded onto a chromatographic column. Gradient elution (20% ethyl acetate in hexane to 50% ethyl acetate in hexane) afforded the product 14 (1.72 g, 72% yield). LC/MS RT 4.37 mins, ES+ 958.30

(b) Compound 15

The TBS ether 14 was allowed to stir in a 3/1/1 mixture of acetic acid, tetrahydrofuran and water for 3 hours at room temperature at which time the reaction was complete. The reaction mixture was diluted with ethyl acetate and sequentially washed with water, saturated aqueous sodium bicarbonate and brine. The organic phase was dried over magnesium sulphate, filtered and excess solvent removed by rotary evaporation under reduced pressure. The resulting residue was subjected to column flash chromatography (silica gel; 80% ethyl acetate in hexane). Pure fractions were collected and combined and removal of excess eluent by rotary evaporation under reduced pressure afforded the product 15 (1.4 g, 93%). LC/MS RT 3.75 mins, ES+ 864.26

(c) Compound 16

Dimethyl sulphoxide (288 µL) was added dropwise to an oven dried sealed microwave vial containing a solution of oxalyl chloride (1.65 µL) in dry dichloromethane (20 mL) at −78° C. (dry ice/acetone bath) under an atmosphere of argon. After 20 minutes a solution of 15 (1.4 g) in dry dichloromethane (15 mL) was added slowly with the temperature still at −78° C. After 15 mins triethylamine (1.13 mL), dried over 4 Å molecular sieves) was added dropwise and the dry ice/acetone bath was removed. The reaction mixture was allowed to reach 20° C. and was extracted with cold hydrochloric acid (0.1 M), saturated aqueous sodium bicarbonate and brine. The organic phase was dried over magnesium sulphate, filtered and excess dichloromethane was removed by rotary evaporation under reduced pressure. The resulting residue was subjected to column flash chromatography (silica gel; gradient 50% ethyl acetate in hexane to 74% ethyl acetate in hexane). Pure fractions were collected and combined and removal of excess eluent by rotary evaporation under reduced pressure afforded the product 16 (930 mg, 70% yield). LC/MS RT 3.60 mins, m/z ES+ 862.08.

(d) Compound 17

Tert-butyldimethylsilyltriflate (744 µL) was added to a solution of compound 16 (930 mg) and 2,6-lutidine (502 µL) in dry dichloromethane (10 mL) and cooled to 0° C. under argon. TLC (ethyl acetate revealed c. 25% product formation after 45 minutes. Additional 2,6 lutidine (502 µL) and TBS triflate (744 µL) were injected and the reaction mixture allowed to warm to room temperature. The reaction mixture was allowed to stir for 30 mins at room temperature at which time TLC indicated that the reaction was complete. The reaction mixture was diluted with dichloromethane (50 mL) washed with saturated ammonium chloride (2×50 mL), and extracted with water (50 mL), aqueous sodium bicarbonate (50 mL) and brine (30 mL). The organic phase was dried over magnesium sulphate, filtered and excess was removed by rotary evaporation under reduced pressure. The resulting residue was subjected to column flash chromatography (silica gel; gradient, 40% ethyl acetate in hexane to 60% ethyl acetate in hexane). Pure fractions were collected and combined and excess eluent was removed by rotary evaporation under reduced pressure to give the product 17 (580 mg, 64% yield). LC/MS RT 5.37 mins, ES+ 976.42.

(e) Compound 18

Lithium acetate (59.5 mg) was added to a solution of compound 17 (570 mg) in wet dimethylformamide (10 mL, 50;1 DMF/water). After 3 hours the reaction was observed to be complete and the reaction mixture was diluted with ethyl acetate and washed with citric acid, water and brine. The organic layer was dried over magnesium sulphate filtered and excess ethyl acetate was removed by rotary evaporation under reduced pressure. The resulting residue was subjected to column flash chromatography (silica gel; gradient, 50% ethyl acetate in hexane to 80% ethyl acetate in hexane). Pure fractions were collected and combined and excess eluent was removed by rotary evaporation under reduced pressure to give the product 18 (476 mg, quantitative yield). LC/MS RT 3.52 mins, ES+ 820.23.

Compound 19

A solution of 13 (70 mL) and the phenol 18 (82.4 mL) over potassium carbonate (13.88 mg) in acetone (2 mL) was heated at 65° C. for 10 hours under argon. The reaction mixture was evaporated to dryness by rotary evaporation under reduced pressure. The residue (including inorganics) was subjected to column flash chromatography (silica gel; gradient 60% ethyl acetate in hexane to 75% ethyl acetate in hexane). Pure fractions were collected and combined and excess eluent removed by rotary evaporation under reduced pressure to afford the product 19 (86 mg, 62% yield). LC/MS RT 4.33 mins, m/z ES+

Example 4

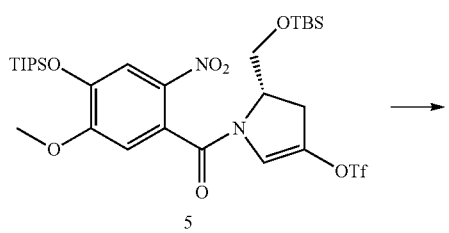

5

Example 3

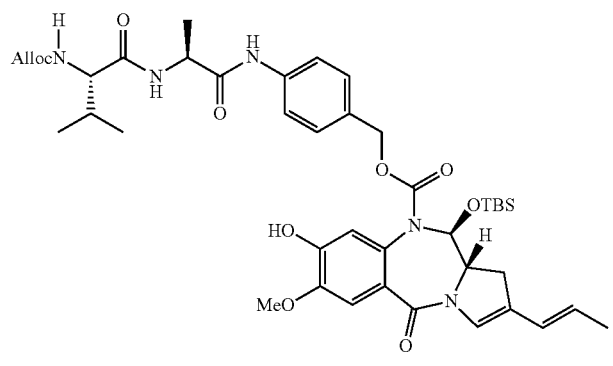

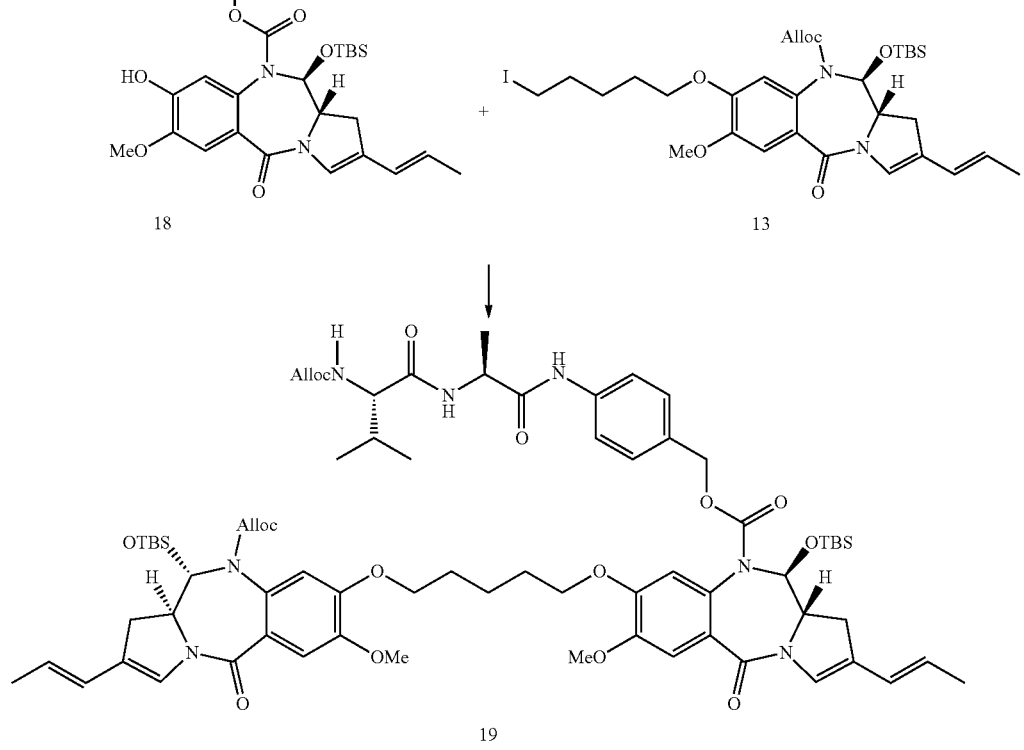

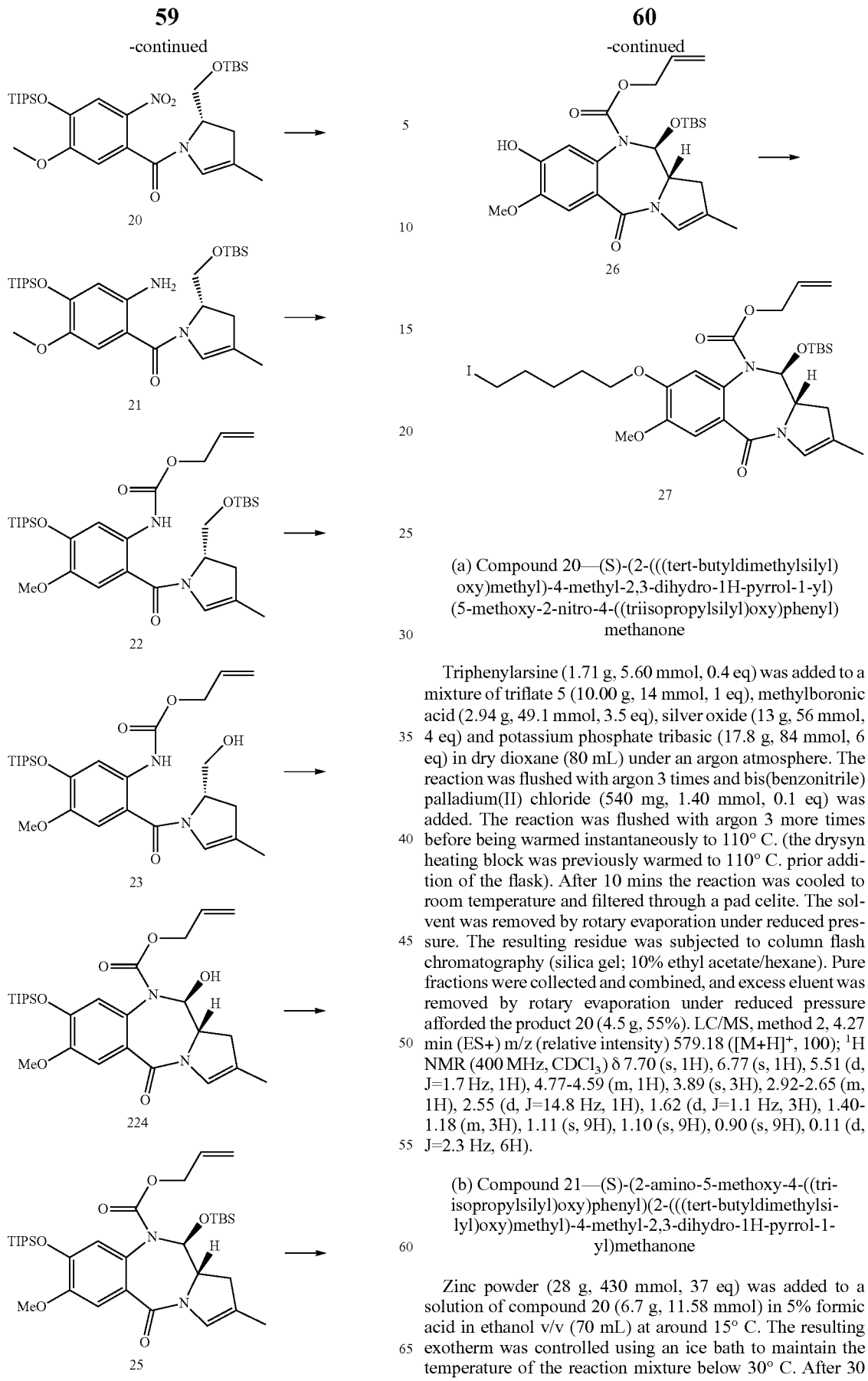

(a) Compound 20—(S)-(2-(((tert-butyldimethylsilyl)oxy)methyl)-4-methyl-2,3-dihydro-1H-pyrrol-1-yl)(5-methoxy-2-nitro-4-(((triisopropylsilyl)oxy)phenyl)methanone Triphenylarsine (1.71 g, 5.60 mmol, 0.4 eq) was added to a mixture of triflate 5 (10.00 g, 14 mmol, 1 eq), methylboronic acid (2.94 g, 49.1 mmol, 3.5 eq), silver oxide (13 g, 56 mmol, 4 eq) and potassium phosphate tribasic (17.8 g, 84 mmol, 6 eq) in dry dioxane (80 mL) under an argon atmosphere. The reaction was flushed with argon 3 times and bis(benzonitrile)palladium(II) chloride (540 mg, 1.40 mmol, 0.1 eq) was added. The reaction was flushed with argon 3 more times before being warmed instantaneously to 110° C. (the drysyn heating block was previously warmed to 110° C. prior addition of the flask). After 10 mins the reaction was cooled to room temperature and filtered through a pad celite. The solvent was removed by rotary evaporation under reduced pressure. The resulting residue was subjected to column flash chromatography (silica gel; 10% ethyl acetate/hexane). Pure fractions were collected and combined, and excess eluent was removed by rotary evaporation under reduced pressure afforded the product 20 (4.5 g, 55%). LC/MS, method 2, 4.27 min (ES+) m/z (relative intensity) 579.18 ([M+H]$^+$, 100); $^1$H NMR (400 MHz, CDCl$_3$) δ 7.70 (s, 1H), 6.77 (s, 1H), 5.51 (d, J=1.7 Hz, 1H), 4.77-4.59 (m, 1H), 3.89 (s, 3H), 2.92-2.65 (m, 1H), 2.55 (d, J=14.8 Hz, 1H), 1.62 (d, J=1.1 Hz, 3H), 1.40-1.18 (m, 3H), 1.11 (s, 9H), 1.10 (s, 9H), 0.90 (s, 9H), 0.11 (d, J=2.3 Hz, 6H).

(b) Compound 21—(S)-(2-amino-5-methoxy-4-((triisopropylsilyl)oxy)phenyl)(2-(((tert-butyldimethylsilyl)oxy)methyl)-4-methyl-2,3-dihydro-1H-pyrrol-1-yl)methanone Zinc powder (28 g, 430 mmol, 37 eq) was added to a solution of compound 20 (6.7 g, 11.58 mmol) in 5% formic acid in ethanol v/v (70 mL) at around 15° C. The resulting exotherm was controlled using an ice bath to maintain the temperature of the reaction mixture below 30° C. After 30 minutes the reaction mixture was filtered through a pad of celite. The filtrate was diluted with ethyl acetate and the organic phase was washed with water, saturated aqueous sodium bicarbonate and brine. The organic phase was dried over magnesium sulphate, filtered and excess solvent removed by rotary evaporation under reduced pressure. The resulting residue was subjected to flash column chromatography (silica gel; 10% ethyl acetate in hexane). The pure fractions were collected and combined and excess solvent was removed by rotary evaporation under reduced pressure to afford the product 21 (5.1 g, 80%). LC/MS, method 2, 4.23 min (ES+) m/z (relative intensity) 550.21 ([M+H]$^{+\cdot}$, 100); $^1$H NMR (400 MHz, CDCl$_3$) δ 7.28 (s, 1H), 6.67 (s, 1H), 6.19 (s, 1H), 4.64-4.53 (m, J=4.1 Hz, 1H), 4.17 (s, 1H), 3.87 (s, 1H), 3.77-3.69 (m, 1H), 3.66 (s, 3H), 2.71-2.60 (m, 1H), 2.53-2.43 (m, 1H), 2.04-1.97 (m, J=11.9 Hz, 1H), 1.62 (s, 3H), 1.26-1.13 (m, 3H), 1.08-0.99 (m, 18H), 0.82 (s, 9H), 0.03--0.03 (m, J=6.2 Hz, 6H).

(c) Compound 22—(S)-allyl (2-(2-(((tert-butyldimethylsilyl)oxy)methyl)-4-methyl-2,3-dihydro-1H-pyrrole-1-carbonyl)-4-methoxy-5-((triisopropylsilyl)oxy)phenyl)carbamate Allyl chloroformate (0.30 mL, 3.00 mmol, 1.1 eq) was added to a solution of amine 21 (1.5 g, 2.73 mmol) in the presence of dry pyridine (0.48 mL, 6.00 mmol, 2.2 eq) in dry dichloromethane (20 mL) at −78° C. (acetone/dry ice bath). After 30 minutes, the bath was removed and the reaction mixture was allowed to warm to room temperature. The reaction mixture was diluted with dichloromethane and saturated aqueous copper sulphate was added. The organic layer was then washed sequentially with saturated aqueous sodium bicarbonate and brine. The organic phase was dried over magnesium sulphate, filtered and excess solvent removed by rotary evaporation under reduced pressure to afford the product 22 which was used directly in the next reaction. LC/MS, method 2, 4.45 min (ES+) m/z (relative intensity) 632.91 ([M+H]$^{+\cdot}$, 100)

(d) Compound 23—(S)-allyl (2-(2-(hydroxymethyl)-4-methyl-2,3-dihydro-1H-pyrrole-1-carbonyl)-4-methoxy-5-((triisopropylsilyl)oxy)phenyl)carbamate The crude 22 was dissolved in a 7:1:1:2 mixture of acetic acid/methanol/tetrahydrofuran/water (28:4:4:8 mL) and allowed to stir at room temperature. After 3 h, complete disappearance of starting material was observed by LC/MS. The reaction mixture was diluted with ethyl acetate and washed sequentially with water (2×500 mL), saturated aqueous sodium bicarbonate (200 mL) and brine. The organic phase was dried over magnesium sulphate filtered and excess ethyl acetate removed by rotary evaporation under reduced pressure. The resulting residue was subjected to flash column chromatography (silica gel; 25% ethyl acetate in hexane). Pure fractions were collected and combined and excess eluent was removed by rotary evaporation under reduced pressure to afford the desired product 23 (1 g, 71%). LC/MS, method 2, 3.70 min (ES+) m/z (relative intensity) 519.13 ([M+H]$^+$, 95); $^1$H NMR (400 MHz, CDCl$_3$) δ 8.34 (s, 1H), 7.69 (s, 1H), 6.78 (s, 1H), 6.15 (s, 1H), 5.95 (ddt, J=17.2, 10.5, 5.7 Hz, 1H), 5.33 (dq, J=17.2, 1.5 Hz, 1H), 5.23 (ddd, J=10.4, 2.6, 1.3 Hz, 1H), 4.73 (tt, J=7.8, 4.8 Hz, 1H), 4.63 (dt, J=5.7, 1.4 Hz, 2H), 4.54 (s, 1H), 3.89-3.70 (m, 5H), 2.87 (dd, J=16.5, 10.5 Hz, 1H), 2.19 (dd, J=16.8, 4.6 Hz, 1H), 1.70 (d, J=1.3 Hz, 3H), 1.38-1.23 (m, 3H), 1.12 (s, 10H), 1.10 (s, 8H).

(e) Compound 24—(11S,11aS)-allyl 11-hydroxy-7-methoxy-2-methyl-5-oxo-8-((triisopropylsilyl)oxy)-11,11a-dihydro-1H-benzo[e]pyrrolo[1,2-a][1,4]diazepine-10(5H)-carboxylate Dimethyl sulphoxide (0.35 mL, 4.83 mmol, 2.5 eq) was added dropwise to a solution of oxalyl chloride (0.2 mL, 2.32 mmol, 1.2 eq) in dry dichloromethane (10 mL) at −78° C. (dry ice/acetone bath) under an atmosphere of argon. After 10 minutes a solution of 23 (1 g, 1.93 mmol) in dry dichloromethane (8 mL) was added slowly with the temperature still at −78° C. After 15 minutes triethylamine (1.35 mL, dried over 4 Å molecular sieves, 9.65 mmol, 5 eq) was added dropwise and the dry ice/acetone bath was removed. The reaction mixture was allowed to reach room temperature and was extracted with cold hydrochloric acid (0.1 M), saturated aqueous sodium bicarbonate and brine. The organic phase was dried over magnesium sulphate, filtered and excess dichloromethane was removed by rotary evaporation under reduced pressure to afford product 24 (658 mg, 66%). LC/MS, method 2, 3.52 min (ES+) m/z (relative intensity) 517.14 ([M+H]$^+$, 100); $^1$H NMR (400 MHz, CDCl$_3$) δ 7.20 (s, 1H), 6.75-6.63 (m, J=8.8, 4.0 Hz, 2H), 5.89-5.64 (m, J=9.6, 4.1 Hz, 2H), 5.23-5.03 (m, 2H), 4.68-4.38 (m, 2H), 3.84 (s, 3H), 3.83-3.77 (m, 1H), 3.40 (s, 1H), 3.05-2.83 (m, 1H), 2.59 (d, J=17.1 Hz, 1H), 1.78 (d, J=1.3 Hz, 3H), 1.33-1.16 (m, 3H), 1.09 (d, J=2.2 Hz, 9H), 1.07 (d, J=2.1 Hz, 9H).

(f) Compound 25—(11S,11aS)-allyl 11-((tert-butyldimethylsilyl)oxy)-7-methoxy-2-methyl-5-oxo-8-((triisopropylsilyl)oxy)-11,11a-dihydro-1H-benzo[e]pyrrolo[1,2-a][1,4]diazepine-10(5H)-carboxylate Tert-butyldimethylsilyltriflate (0.70 mL, 3.00 mmol, 3 eq) was added to a solution of compound 24 (520 mg, 1.00 mmol) and 2,6-lutidine (0.46 mL, 4.00 mmol, 4 eq) in dry dichloromethane (40 mL) at 0° C. under argon. After 10 minutes, the cold bath was removed and the reaction mixture was stirred at room temperature for 1 hour. The reaction mixture was extracted with water, saturated aqueous sodium bicarbonate and brine. The organic phase was dried over magnesium sulphate, filtered and excess was removed by rotary evaporation under reduced pressure. The resulting residue was subjected to flash column chromatography (silica gel; gradient, 10% ethyl acetate in hexane to 20% ethyl acetate in hexane). Pure fractions were collected and combined and excess eluent was removed by rotary evaporation under reduced pressure to give the product 25 (540 mg, 85%). LC/MS, method 2, 4.42 min (ES+) m/z (relative intensity) 653.14 ([M+Na]$^{+\cdot}$, 100); $^1$H NMR (400 MHz, CDCl$_3$) δ 7.20 (s, 1H), 6.71-6.64 (m, J=5.5 Hz, 2H), 5.83 (d, J=9.0 Hz, 1H), 5.80-5.68 (m, J=5.9 Hz, 1H), 5.14-5.06 (m, 2H), 4.58 (dd, J=13.2, 5.2 Hz, 1H), 4.36 (dd, J=13.3, 5.5 Hz, 1H), 3.84 (s, 3H), 3.71 (td, J=10.1, 3.8 Hz, 1H), 2.91 (dd, J=16.9, 10.3 Hz, 1H), 2.36 (d, J=16.8 Hz, 1H), 1.75 (s, 3H), 1.31-1.16 (m, 3H), 1.12-1.01 (m, J=7.4, 2.1 Hz, 18H), 0.89-0.81 (m, 9H), 0.25 (s, 3H), 0.19 (s, 3H).

(g) Compound 26—(11S,11aS)-allyl 11-((tert-butyldimethylsilyl)oxy)-8-hydroxy-7-methoxy-2-methyl-5-oxo-11,11a-dihydro-1H-benzo[e]pyrrolo[1,2-a][1,4]diazepine-10(5H)-carboxylate Lithium acetate (87 mg, 0.85 mmol) was added to a solution of compound 25 (540 mg, 0.85 mmol) in wet dimethylformamide (6 mL, 50:1 DMF/water). After 4 hours, the reaction was complete and the reaction mixture was diluted with ethyl acetate (25 mL) and washed with aqueous citric acid solution (pH~3), water and brine. The organic layer was dried over magnesium sulphate filtered and excess ethyl acetate was removed by rotary evaporation under reduced pressure. The resulting residue was subjected to flash column chromatography (silica gel; gradient, 25% to 75% ethyl acetate in hexane). Pure fractions were collected and combined and excess eluent was removed by rotary evaporation under reduced pressure to give the product 26 (400 mg, quantitative). LC/MS, method 2, (3.33 min (ES+) m/z (relative intensity) 475.26 ([M+H]$^+$, 100).

(h) Compound 27—(11S,11aS)-allyl 11-((tert-butyldimethylsilyl)oxy)-8-((5-iodopentyl)oxy)-7-methoxy-2-methyl-5-oxo-11,11a-dihydro-1H-benzo[e]pyrrolo[1,2-a][1,4]diazepine-10(5H)-carboxylate Diiodopentane (0.63 mL, 4.21 mmol, 5 eq) and potassium carbonate (116 mg, 0.84 mmol, 1 eq) were added to a solution of phenol 26 (400 mg, 0.84 mmol) in acetone (4 mL, dried over molecular sieves). The reaction mixture was then warmed to 60° C. and stirred for 6 hours. Acetone was removed by rotary evaporation under reduced pressure. The resulting residue was subjected to flash column chromatography (silica gel; 50/50, v/v, hexane/ethyl acetate,). Pure fractions were collected and combined and excess eluent was removed to provide 27 in 90% yield. LC/MS, method 2, 3.90 min (ES+) m/z (relative intensity) 670.91 ([M]$^+$, 100). $^1$H NMR (400 MHz, CDCl$_3$) δ 7.23 (s, 1H), 6.69 (s, 1H), 6.60 (s, 1H), 5.87 (d, J=8.8 Hz, 1H), 5.83-5.68 (m, J=5.6 Hz, 1H), 5.15-5.01 (m, 2H), 4.67-4.58 (m, 1H), 4.45-4.35 (m, 1H), 4.04-3.93 (m, 2H), 3.91 (s, 3H), 3.73 (td, J=10.0, 3.8 Hz, 1H), 3.25-3.14 (m, J=8.5, 7.0 Hz, 2H), 2.92 (dd, J=16.8, 10.3 Hz, 1H), 2.38 (d, J=16.8 Hz, 1H), 1.95-1.81 (m, 4H), 1.77 (s, 3H), 1.64-1.49 (m, 2H), 0.88 (s, 9H), 0.25 (s, 3H), 0.23 (s, 3H).

Example 5

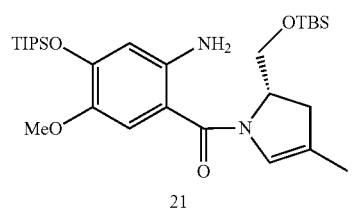

21

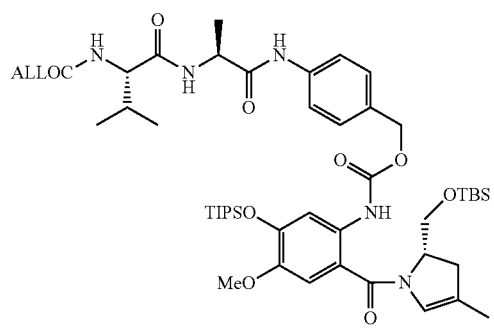

28

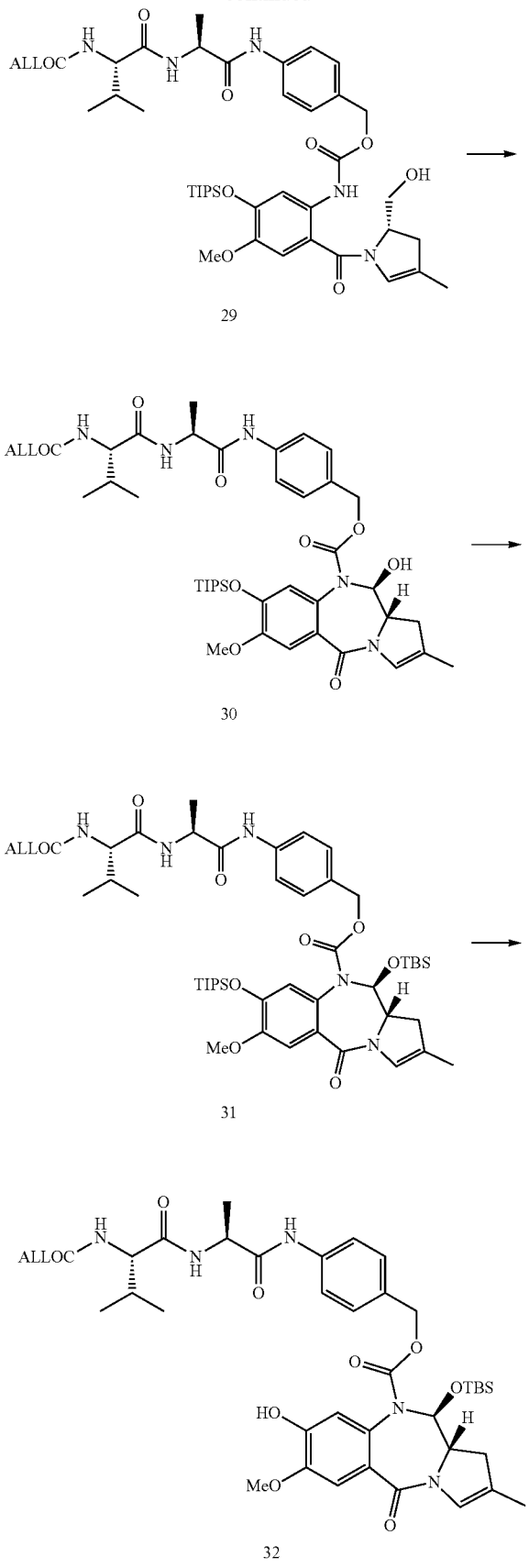

(a) Compound 28—allyl 3-(2-(2-(4-((((2-((S)-2-(((tert-butyldimethylsilyl)oxy)methyl)-4-methyl-2,3-dihydro-1H-pyrrole-1-carbonyl)-4-methoxy-5-((triisopropylsilyl)oxy)phenyl)carbamoyl)oxy)methyl)phenyl)hydrazinyl)propanamido)-4-methyl-2-oxopentanoate Triethylamine (2.23 mL, 18.04 mmol, 2.2 eq) was added to a stirred solution of the amine 21 (4 g, 8.20 mmol) and triphosgene (778 mg, 2.95 mmol, 0.36 eq) in dry tetrahydrofuran (40 mL) at 5° C. (ice bath). The progress of the isocyanate reaction was monitored by periodically removing aliquots from the reaction mixture and quenching with methanol and performing LC/MS analysis. Once the isocyanate formation was complete a solution of the alloc-Val-Ala-PABOH (4.12 g, 12.30 mmol, 1.5 eq) and triethylamine (1.52 mL, 12.30 mmol, 1.5 eq) in dry tetrahydrofuran (40 mL) was rapidly added by injection to the freshly prepared isocyanate. The reaction mixture was allowed to stir at 40° C. for 4 hours. Excess solvent was removed by rotary evaporation under reduced pressure. The resulting residue was subjected to flash column chromatography (silica gel; gradient, 1% methanol to 5% methanol in dichloromethane). (Alternative chromatography conditions using EtOAc and Hexane have also been successful). Pure fractions were collected and combined and excess eluent was removed by rotary evaporation under reduced pressure to give the product 28 (3.9 g, 50%). LC/MS, method 2, 4.23 min (ES+) m/z (relative intensity) 952.36 ([M+H]$^{+\cdot}$, 100); $^1$H NMR (400 MHz, CDCl$_3$) δ 8.62 (br s, 1H), 8.46 (s, 1H), 7.77 (br s, 1H), 7.53 (d, J=8.4 Hz, 2H), 7.32 (d, J=8.5 Hz, 2H), 6.76 (s, 1H), 6.57 (d, J=7.6 Hz, 1H), 6.17 (s, 1H), 6.03-5.83 (m, 1H), 5.26 (dd, J=33.8, 13.5 Hz, 3H), 5.10 (s, 2H), 4.70-4.60 (m, 2H), 4.58 (dd, J=5.7, 1.3 Hz, 2H), 4.06-3.99 (m, 1H), 3.92 (s, 1H), 3.82-3.71 (m, 1H), 3.75 (s, 3H), 2.79-2.64 (m, 1H), 2.54 (d, J=12.9 Hz, 1H), 2.16 (dq, J=13.5, 6.7 Hz, 1H), 1.67 (s, 3H), 1.46 (d, J=7.0 Hz, 3H), 1.35-1.24 (m, 3H), 1.12 (s, 9H), 1.10 (s, 9H), 0.97 (d, J=6.8 Hz, 3H), 0.94 (d, J=6.8 Hz, 3H), 0.87 (s, 9H), 0.07-0.02 (m, 6H).

(b) Compound 29—allyl 3-(2-(2-(4-((((2-((S)-2-(hydroxymethyl)-4-methyl-2,3-dihydro-1H-pyrrole-1-carbonyl)-4-methoxy-5-((triisopropylsilyl)oxy)phenyl)carbamoyl)oxy)methyl)phenyl)hydrazinyl)propanamido)-4-methyl-2-oxopentanoate The TBS ether 28 (1.32 g, 1.38 mmol) was dissolved in a 7:1:1:2 mixture of acetic acid/methanol/tetrahydrofuran/water (14:2:2:4 mL) and allowed to stir at room temperature. After 3 hours no more starting material was observed by LC/MS. The reaction mixture was diluted with ethyl acetate (25 mL) and washed sequentially with water, saturated aqueous sodium bicarbonate and brine. The organic phase was dried over magnesium sulphate filtered and excess ethyl acetate removed by rotary evaporation under reduced pressure. The resulting residue was subjected to flash column chromatography (silica gel, 2% methanol in dichloromethane). Pure fractions were collected and combined and excess eluent was removed by rotary evaporation under reduced pressure to afford the desired product 29 (920 mg, 80%). LC/MS, method 2, 3.60 min (ES+) m/z (relative intensity) 838.18 ([M+H]$^{+\cdot}$, 100). $^1$H NMR (400 MHz, CDCl$_3$) δ 8.55 (s, 1H), 8.35 (s, 1H), 7.68 (s, 1H), 7.52 (d, J=8.1 Hz, 2H), 7.31 (d, J=8.4 Hz, 2H), 6.77 (s, 1H), 6.71 (d, J=7.5 Hz, 1H), 6.13 (s, 1H), 5.97-5.82 (m, J=5.7 Hz, 1H), 5.41-5.15 (m, 3H), 5.10 (d, J=3.5 Hz, 2H), 4.76-4.42 (m, 5H), 4.03 (t, J=6.6 Hz, 1H), 3.77 (s, 5H), 2.84 (dd, J=16.7, 10.4 Hz, 1H), 2.26-2.08 (m, 2H), 1.68 (s, 3H), 1.44 (d, J=7.0 Hz, 3H), 1.30 (dt, J=14.7, 7.4 Hz, 3H), 1.12 (s, 9H), 1.10 (s, 9H), 0.96 (d, J=6.8 Hz, 3H), 0.93 (d, J=6.8 Hz, 3H).

(c) Compound 30—(11S,11aS)-4-(2-(1-((1-(allyloxy)-4-methyl-1,2-dioxopentan-3-yl)amino)-1-oxopropan-2-yl)hydrazinyl)benzyl 11-hydroxy-7-methoxy-2-methyl-5-oxo-8-((triisopropylsilyl)oxy)-11,11a-dihydro-1H-benzo[e]pyrrolo[1,2-a][1,4]diazepine-10(5H)-carboxylate Dimethyl sulphoxide (0.2 mL, 2.75 mmol, 2.5 eq) was added dropwise to a solution of oxalyl chloride (0.11 mL, 1.32 mmol, 1.2 eq) in dry dichloromethane (7 mL) at −78° C. (dry ice/acetone bath) under an atmosphere of argon. After 10 minutes a solution of 29 (920 mg, 1.10 mmol) in dry dichloromethane (5 mL) was added slowly with the temperature still at −78° C. After 15 minutes triethylamine (0.77 mL, dried over 4 Å molecular sieves, 5.50 mmol, 5 eq) was added dropwise and the dry ice/acetone bath was removed. The reaction mixture was allowed to reach room temperature and was extracted with cold hydrochloric acid (0.1 M), saturated aqueous sodium bicarbonate and brine. The organic phase was dried over magnesium sulphate, filtered and excess dichloromethane was removed by rotary evaporation under reduced pressure. The resulting residue was subjected to column flash chromatography (silica gel; gradient 2% methanol to 5% methanol in dichloromethane). Pure fractions were collected and combined and removal of excess eluent by rotary evaporation under reduced pressure afforded the product 30 (550 mg, 60%). LC/MS, method 2, 3.43 min (ES+) m/z (relative intensity) 836.01 ([M]$^{+\cdot}$, 100). $^1$H NMR (400 MHz, CDCl$_3$) δ 8.39 (s, 1H), 7.52-7.40 (m, 2H), 7.21-7.08 (m, J=11.5 Hz, 2H), 6.67 (s, 1H), 6.60-6.47 (m, J=7.4 Hz, 1H), 5.97-5.83 (m, 1H), 5.79-5.66 (m, 1H), 5.38-4.90 (m, 6H), 4.68-4.52 (m, J=18.4, 5.5 Hz, 4H), 4.04-3.94 (m, J=6.5 Hz, 1H), 3.87-3.76 (m, 5H), 3.00-2.88 (m, 1H), 2.66-2.49 (m, 2H), 2.21-2.08 (m, 2H), 1.76 (s, 3H), 1.45 (d, J=7.0 Hz, 3H), 1.09-0.98 (m, J=8.9 Hz, 18H), 0.96 (d, J=6.7 Hz, 3H), 0.93 (d, J=6.9 Hz, 3H).

(d) Compound 31—(11S,11aS)-4-(2-(1-((1-(allyloxy)-4-methyl-1,2-dioxopentan-3-yl)amino)-1-oxopropan-2-yl)hydrazinyl)benzyl 11-((tert-butyldimethylsilyl)oxy)-7-methoxy-2-methyl-5-oxo-8-((triisopropylsilyl)oxy)-11,11a-dihydro-1H-benzo[e]pyrrolo[1,2-a][1,4]diazepine-10(5H)-carboxylate Tert-butyldimethylsilyltriflate (0.38 mL, 1.62 mmol, 3 eq) was added to a solution of compound 30 (450 mg, 0.54 mmol) and 2,6-lutidine (0.25 mL, 2.16 mmol, 4 eq) in dry dichloromethane (5 mL) at 0° C. under argon. After 10 minutes, the cold bath was removed and the reaction mixture was stirred at room temperature for 1 hour. The reaction mixture was extracted with water, saturated aqueous sodium bicarbonate and brine. The organic phase was dried over magnesium sulphate, filtered and excess solvent was removed by rotary evaporation under reduced pressure. The resulting residue was subjected to column flash chromatography (silica gel; 50/50 v/v hexane/ethyl acetate). Pure fractions were collected and combined and excess eluent was removed by rotary evaporation under reduced pressure to give the product 31 (334 mg, 65%). LC/MS, method 2, 4.18 min (ES+) m/z (relative intensity) 950.50 ([M]+·, 100). $^1$H NMR (400 MHz, CDCl$_3$) δ 8.53 (s, 1H), 8.02 (s, 1H), 7.44 (d, J=7.6 Hz, 2H), 7.21 (s, 1H), 7.08 (d, J=8.2 Hz, 2H), 6.72-6.61 (m, J=8.9 Hz, 2H), 6.16 (s, 1H), 5.97-5.79 (m, J=24.4, 7.5 Hz, 2H), 5.41-5.08 (m, 5H), 4.86 (d, J=12.5 Hz, 1H), 4.69-4.60 (m, 1H), 4.57 (s, 1H), 4.03 (t, J=6.7 Hz, 1H), 3.87 (s, 3H), 3.74 (td, J=9.6, 3.6 Hz, 1H), 2.43-2.09 (m, J=34.8, 19.4, 11.7 Hz, 3H), 1.76 (s, 3H), 1.43 (d, J=6.9 Hz, 3H), 1.30-1.21 (m, 3H), 0.97 (d, J=6.7 Hz, 3H), 0.92 (t, J=8.4 Hz, 3H), 0.84 (s, 9H), 0.23 (s, 3H), 0.12 (s, 3H).

(e) Compound 32—(11S,11aS)-4-(2-(1-((1-(allyloxy)-4-methyl-1,2-dioxopentan-3-yl)amino)-1-oxopropan-2-yl)hydrazinyl)benzyl 11-((tert-butyldimethylsilyl)oxy)-8-hydroxy-7-methoxy-2-methyl-5-oxo-11,11a-dihydro-1H-benzo[e]pyrrolo[1,2-a][1,4]diazepine-10(5H)-carboxylate Lithium acetate (50 mg, 0.49 mmol) was added to a solution of compound 31 (470 mg, 0.49 mmol) in wet dimethylformamide (4 mL, 50:1 DMF/water). After 4 hours, the reaction was complete and the reaction mixture was diluted with ethyl acetate and washed with citric acid (pH~3), water and brine. The organic layer was dried over magnesium sulphate filtered and excess ethyl acetate was removed by rotary evaporation under reduced pressure. The resulting residue was subjected to column flash chromatography (silica gel; gradient, 50/50 to 25/75 v/v hexane/ethyl acetate). Pure fractions were collected and combined and excess eluent was removed by rotary evaporation under reduced pressure to give the product 32 (400 mg, quantitative). LC/MS, method 2, 3.32 min (ES+) m/z (relative intensity) 794.18 ([M+H]+·, 100). $^1$H NMR (400 MHz, CDCl$_3$) δ 8.53 (s, 1H), 8.02 (s, 1H), 7.44 (d, J=7.6 Hz, 2H), 7.21 (s, 1H), 7.08 (d, J=8.2 Hz, 2H), 6.72-6.61 (m, J=8.9 Hz, 2H), 6.16 (s, 1H), 5.97-5.79 (m, J=24.4, 7.5 Hz, 2H), 5.41-5.08 (m, 5H), 4.86 (d, J=12.5 Hz, 1H), 4.69-4.60 (m, 1H), 4.57 (s, 1H), 4.03 (t, J=6.7 Hz, 1H), 3.87 (s, 3H), 3.74 (td, J=9.6, 3.6 Hz, 1H), 2.43-2.09 (m, J=34.8, 19.4, 11.7 Hz, 3H), 1.76 (s, 3H), 1.43 (d, J=6.9 Hz, 3H), 1.30-1.21 (m, 3H), 0.97 (d, J=6.7 Hz, 3H), 0.92 (t, J=8.4 Hz, 3H), 0.84 (s, 9H), 0.23 (s, 3H), 0.12 (s, 3H).

Example 6

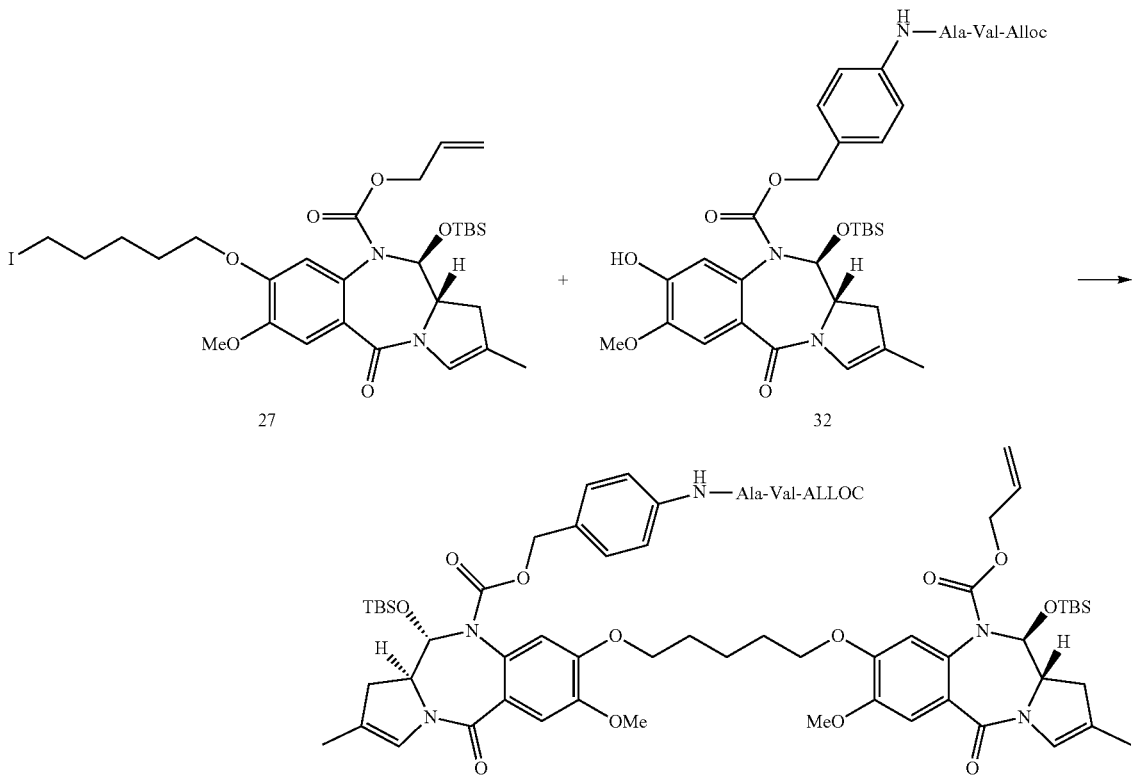

Compound 33—(11S)-allyl 8-((5-(((11S)-10-(((4-(2-(1-((1-(allyloxy)-4-methyl-1,2-dioxopentan-3-yl)amino)-1-oxopropan-2-yl)hydrazinyl)benzyl)oxy)carbonyl)-11-((tert-butyldimethylsilyl)oxy)-7-methoxy-2-methyl-5-oxo-5,10,11,11a-tetrahydro-1H-benzo[e]pyrrolo[1,2-a][1,4]diazepin-8-yl)oxy)pentyl)oxy)-11-((tert-butyldimethylsilyl)oxy)-7-methoxy-2-methyl-5-oxo-11,11a-dihydro-1H-benzo[e]pyrrolo[1,2-a][1,4]diazepine-10(5H)-carboxylate Potassium carbonate (70 mg, 0.504 mmol, 1 eq) was added to a solution of 27 (370 mg, 0.552 mmol, 1.2 eq) and phenol 32 (400 mg, 0.504 mmol) in dry acetone (25 mL). The reaction was stirred 8 hours at 70° C. The LC/MS showed that all the starting material was not consumed, so the reaction was allowed to stir overnight at room temperature and stirred for an additional 2 hours the next day. Acetone was removed by rotary evaporation under reduced pressure. The resulting residue was subjected to flash column chromatography (silica gel; 80% ethyl acetate in hexane to 100% ethyl acetate). Pure fractions were collected and combined and excess eluent was removed by rotary evaporation under reduced pressure to give the product 33 (385 mg, 57%). LC/MS, method 2, 4.07 min (ES+) m/z (relative intensity) 1336.55 ([M+H]$^{+\cdot}$, 50).

Example 7

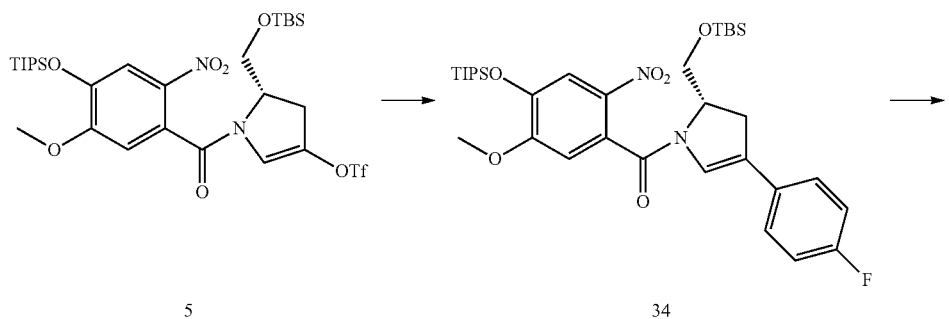

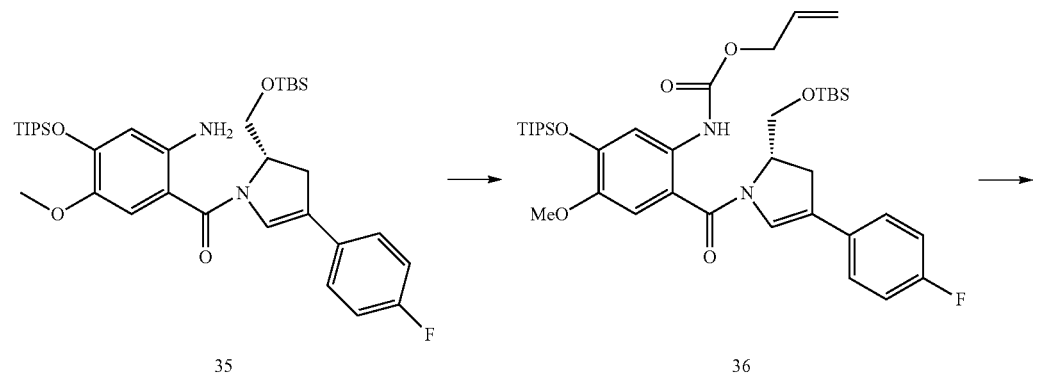

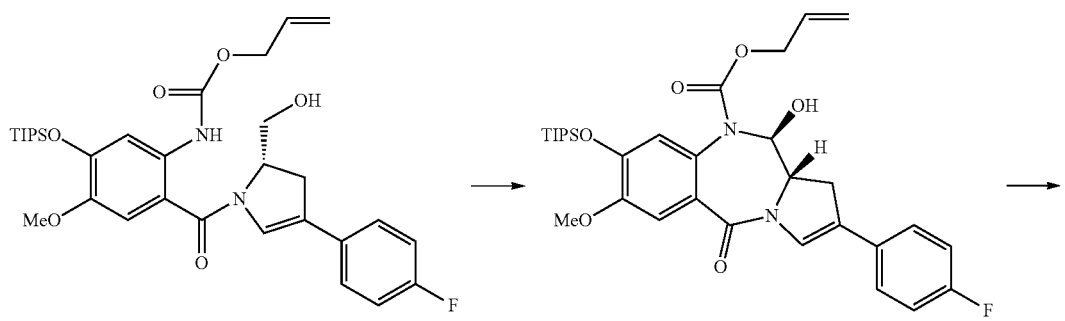

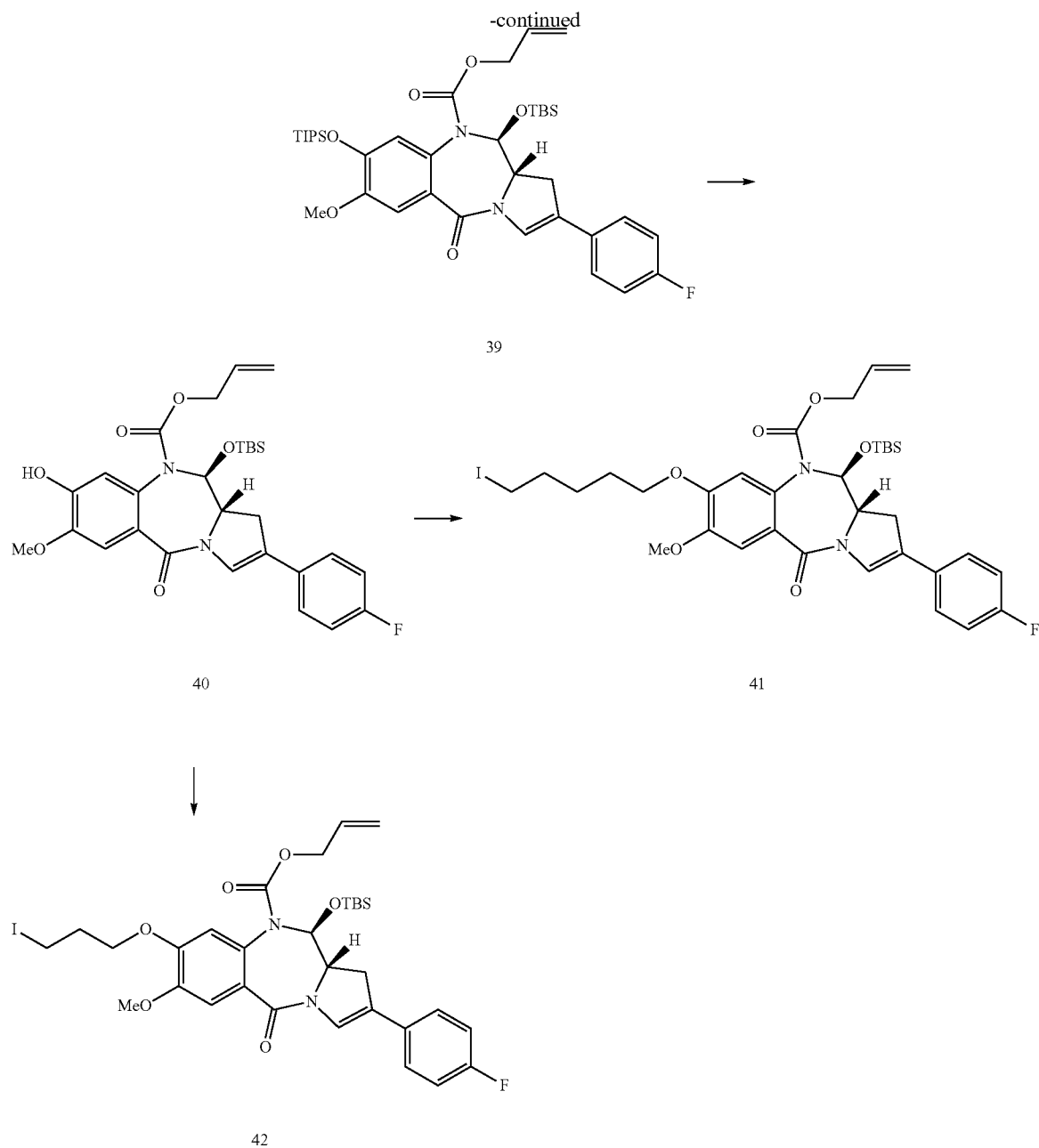

(a) Compound 34—(S)-(2-(((tert-butyldimethylsilyl) oxy)methyl)-4-(4-fluorophenyl)-2,3-dihydro-1H-pyrrol-1-yl)(5-methoxy-2-nitro-4-((triisopropylsilyl) oxy)phenyl)methanone Tetrakis(triphenylphosphine) palladium(0) (1.65 g, 1.43 mmol, 0.03 eq) was added to a mixture of triflate 5 (34.00 g, 47.6 mmol, 1 eq), 4-fluorophenylboronic acid (8.00 g, 57.17 mmol, 1.2 eq) and potassium phosphate tribasic (20.2 g, 95.16 mmol, 2 eq) in dry dioxane (170 mL) under an argon atmosphere. The reaction was flushed with argon 3 times and stirred at ambient temperature for 12 hours. The reaction was diluted with ethyl acetate and the organic phase was washed with water and brine and dried over magnesium sulphate. The solvent was removed by rotary evaporation under reduced pressure. The resulting residue was subjected to column flash chromatography (silica gel; 10% ethyl acetate/hexane). Pure fractions were collected and combined, and excess eluent was removed by rotary evaporation under reduced pressure afforded the product 34 (19 g, 61%). LC/MS, method 2, 4.28 min (ES+) m/z (relative intensity) 659.17 ([M+H]$^{+\cdot}$, 60)

(b) Compound 35—(S)-(2-amino-5-methoxy-4-((triisopropylsilyl)oxy)phenyl)(2-(((tert-butyldimethylsilyl)oxy)methyl)-4-(4-fluorophenyl)-2,3-dihydro-1H-pyrrol-1-yl)methanone Zinc powder (44.2 g, 676 mmol, 37 eq) was added to a solution of compound 34 (12 g, 18.21 mmol) in 5% formic acid in ethanol v/v (120 mL) at around 15° C. The resulting exotherm was controlled using an ice bath to maintain the temperature of the reaction mixture below 30° C. After 30 minutes the reaction mixture was filtered through a pad of celite. The filtrate was diluted with ethyl acetate and the organic phase was washed with water, saturated aqueous sodium bicarbonate and brine. The organic phase was dried over magnesium sulphate, filtered and excess solvent removed by rotary evaporation under reduced pressure. The resulting residue was subjected to flash column chromatography (silica gel; 5% ethyl acetate in hexane). The pure fractions were collected and combined and excess solvent was removed by rotary evaporation under reduced pressure to afford the product 35 (11 g, 96%). LC/MS, method 2, 4.32 min (ES+) m/z (relative intensity) 630.19 ([M+H]$^{+\cdot}$, 100)

(c) Compound 36—(S)-allyl (2-(2-(((tert-butyldimethylsilyl)oxy)methyl)-4-(4-fluorophenyl)-2,3-dihydro-1H-pyrrole-1-carbonyl)-4-methoxy-5-((triisopropylsilyl)oxy)phenyl)carbamate Allyl chloroformate (0.9 mL, 8.75 mmol, 1.1 eq) was added to a solution of amine 35 (5.0 g, 7.95 mmol) in the presence of dry pyridine (1.4 mL, 17.5 mmol, 2.2 eq) in dry dichloromethane (100 mL) at −78° C. (acetone/dry ice bath). After 30 minutes, the bath was removed and the reaction mixture was allowed to warm to room temperature. The reaction mixture was diluted with dichloromethane and saturated aqueous copper sulphate was added. The organic layer was then washed sequentially with saturated aqueous sodium bicarbonate and brine. The organic phase was dried over magnesium sulphate, filtered and excess solvent removed by rotary evaporation under reduced pressure to afford the product 36 which was used directly in the next reaction. LC/MS, method 2, 4.52 min (ES+) m/z (relative intensity) 712.86 ([M+H]$^{+\cdot}$, 100).

(d) Compound 37—(S)-allyl (2-(4-(4-fluorophenyl)-2-(hydroxymethyl)-2,3-dihydro-1H-pyrrole-1-carbonyl)-4-methoxy-5-((triisopropylsilyl)oxy)phenyl) carbamate The crude 36 was dissolved in a 7:1:1:2 mixture of acetic acid/methanol/tetrahydrofuran/water (28:4:4:8 mL) and allowed to stir at room temperature. After 3 hours, complete disappearance of starting material was observed by LC/MS. The reaction mixture was diluted with ethyl acetate and washed sequentially with water (2×500 mL), saturated aqueous sodium bicarbonate (200 mL) and brine. The organic phase was dried over magnesium sulphate filtered and excess ethyl acetate removed by rotary evaporation under reduced pressure. The resulting residue was subjected to flash column chromatography (silica gel, 25% ethyl acetate in hexane). Pure fractions were collected and combined and excess eluent was removed by rotary evaporation under reduced pressure to afford the desired product 37 (3.0 g, 64% over 2 steps). LC/MS, method 2, 3.85 min (ES+) m/z (relative intensity) 598.69 ([M+H]$^{+\cdot}$, 95)

(e) Compound 38—(11S,11aS)-allyl 2-(4-fluorophenyl)-11-hydroxy-7-methoxy-5-oxo-8-((triisopropylsilyl)oxy)-11,11a-dihydro-1H-benzo[e]pyrrolo[1,2-a][1,4]diazepine-10(5H)-carboxylate Dimethyl sulphoxide (0.89 mL, 12.54 mmol, 2.5 eq) was added dropwise to a solution of oxalyl chloride (0.51 mL, 6.00 mmol, 1.2 eq) in dry dichloromethane (30 mL) at −78° C. (dry ice/acetone bath) under an atmosphere of argon. After 10 minutes a solution of 37 (3 g, 4.98 mmol) in dry dichloromethane (24 mL) was added slowly with the temperature still at −78° C. After 15 minutes triethylamine (3.48 mL, dried over 4 Å molecular sieves, 25.02 mmol, 5 eq) was added dropwise and the dry ice/acetone bath was removed. The reaction mixture was allowed to reach room temperature and was extracted with cold hydrochloric acid (0.1 M), saturated aqueous sodium bicarbonate and brine. The organic phase was dried over magnesium sulphate, filtered and excess dichloromethane was removed by rotary evaporation under reduced pressure to afford product 38 (2.4 g, 80%). LC/MS, method 2, 3.70 min (ES+) m/z (relative intensity) 596.67 ([M+H]$^{+\cdot}$, 100).

(f) Compound 39—(11S,11aS)-allyl 11-((tert-butyldimethylsilyl)oxy)-2-(4-fluorophenyl)-7-methoxy-5-oxo-8-((triisopropylsilyl)oxy)-11,11a-dihydro-1H-benzo[e]pyrrolo[1,2-a][1,4]diazepine-10(5H)-carboxylate Tert-butyldimethylsilyltriflate (3.0 mL, 13.08 mmol, 3 eq) was added to a solution of compound 38 (2.6 g, 4.36 mmol) and 2,6-lutidine (2.0 mL, 17.44 mmol, 4 eq) in dry dichloromethane (40 mL) at 0° C. under argon. After 10 minutes, the cold bath was removed and the reaction mixture was stirred at room temperature for 1 hour. The reaction mixture was extracted with water, saturated aqueous sodium bicarbonate and brine. The organic phase was dried over magnesium sulphate, filtered and excess was removed by rotary evaporation under reduced pressure. The resulting residue was subjected to flash column chromatography (silica gel; gradient, 10% ethyl acetate in hexane to 20% ethyl acetate in hexane). Pure fractions were collected and combined and excess eluent was removed by rotary evaporation under reduced pressure to give the product 39 (2.23 g, 72%). LC/MS, method 2, 4.52 min (ES+) m/z (relative intensity) 710.82 ([M+H]$^{+\cdot}$, 100)

(g) Compound 40—(11S,11aS)-allyl 11-((tert-butyldimethylsilyl)oxy)-2-(4-fluorophenyl)-8-hydroxy-7-methoxy-5-oxo-11,11a-dihydro-1H-benzo[e]pyrrolo[1,2-a][1,4]diazepine-10(5H)-carboxylate Lithium acetate (311 mg, 3.04 mmol) was added to a solution of compound 39 (2.16 g, 3.04 mmol) in wet dimethylformamide (20 mL, 50:1 DMF/water). After 2 hours, the reaction was complete and the reaction mixture was diluted with ethyl acetate (25 mL) and washed with aqueous citric acid solution (pH 3), water and brine. The organic layer was dried over magnesium sulphate filtered and excess ethyl acetate was removed by rotary evaporation under reduced pressure. The resulting residue was subjected to flash column chromatography (silica gel; gradient, 25% to 75% ethyl acetate in hexane). Pure fractions were collected and combined and excess eluent was removed by rotary evaporation under reduced pressure to give the product 40 (1.7 g, quantitative). LC/MS, method 2, (3.57 min (ES+) m/z (relative intensity) 554.93 ([M+H]$^+$, 100).

(h) Compound 41—(11S,11aS)-allyl 11-((tert-butyldimethylsilyl)oxy)-2-(4-fluorophenyl)-8-((5-iodopentyl)oxy)-7-methoxy-5-oxo-11,11a-dihydro-1H-benzo[e]pyrrolo[1,2-a][1,4]diazepine-10(5H)-carboxylate Diiodopentane (1.07 mL, 7.2 mmol, 5 eq) and potassium carbonate (200 mg, 1.44 mmol, 1 eq) were added to a solution of phenol 40 (800 mg, 1.44 mmol) in acetone (8 mL, dried over molecular sieves). The reaction mixture was then warmed to 60° C. and stirred for 6 hours. Acetone was removed by rotary evaporation under reduced pressure. The resulting residue was subjected to flash column chromatography (silica gel; 50/50, v/v, hexane/ethyl acetate,). Pure fractions were collected and combined and excess eluent was removed to provide 41 (800 mg, 74%). LC/MS, method 2, 4.00 min (ES+) m/z (relative intensity) 750.66 ([M+H]+, 100).

(i) Compound 42—(11S,11aS)-allyl 11-((tert-butyldimethylsilyl)oxy)-2-(4-fluorophenyl)-8-(3-iodopropoxy)-7-methoxy-5-oxo-11,11a-dihydro-1H-benzo[e]pyrrolo[1,2-a][1,4]diazepine-10(5H)-carboxylate Diiodopropane (0.52 mL, 4.50 mmol, 5 eq) and potassium carbonate (124 mg, 0.90 mmol, 1 eq) were added to a solution of phenol 40 (500 mg, 0.90 mmol) in acetone (5 mL, dried over molecular sieves). The reaction mixture was then warmed to 60° C. and stirred for 3 hours. Acetone was removed by rotary evaporation under reduced pressure. The resulting residue was subjected to flash column chromatography (silica gel; 50/50, v/v, hexane/ethyl acetate,). Pure fractions were collected and combined and excess eluent was removed to provide 42 (450 mg, 70% with some impurities due to elimination reaction). LC/MS, method 2, 3.90 min (ES+) m/z (relative intensity) 722.33 ([M+H]+, 100).

Example 8

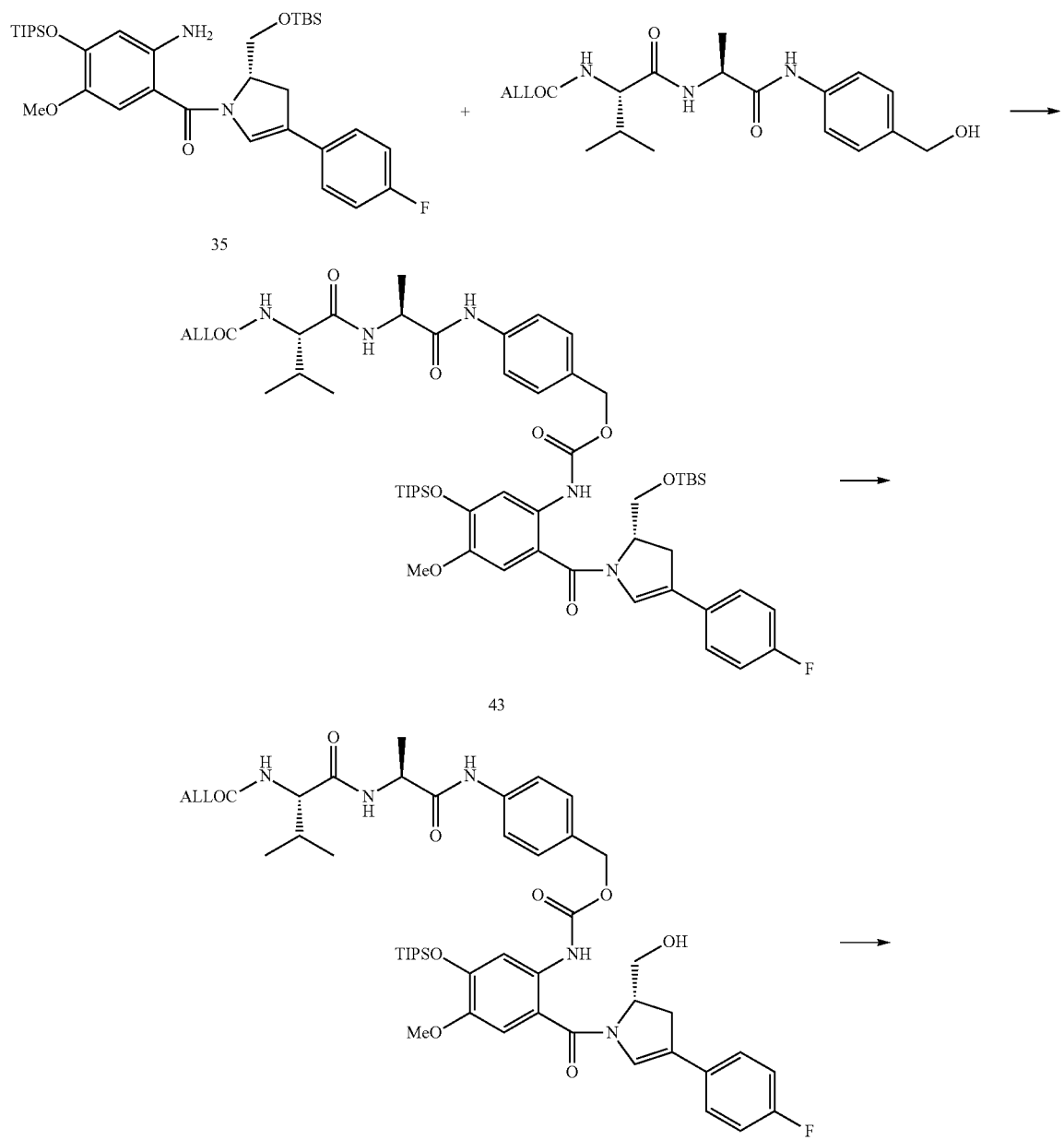

-continued
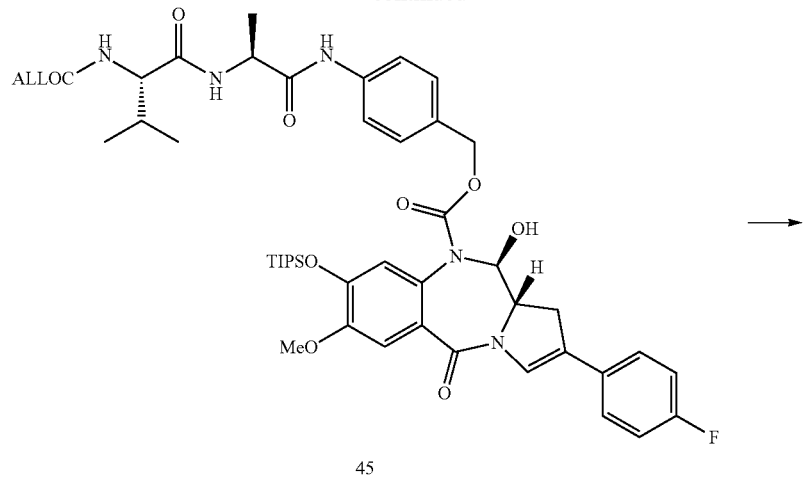
45
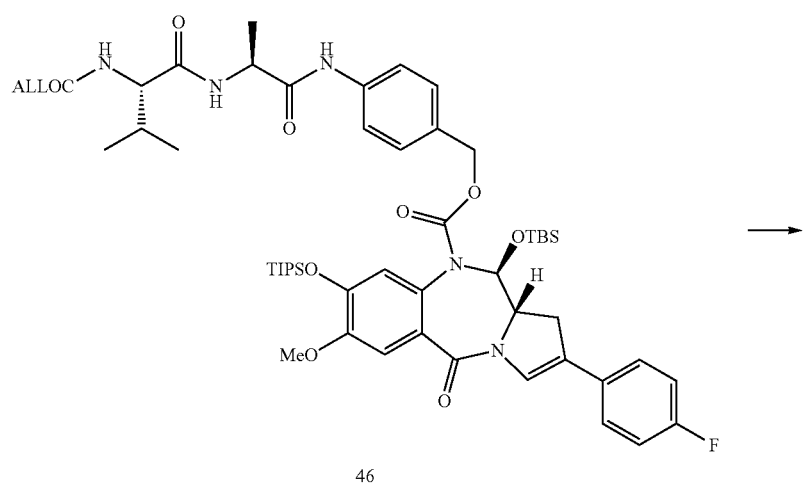
46
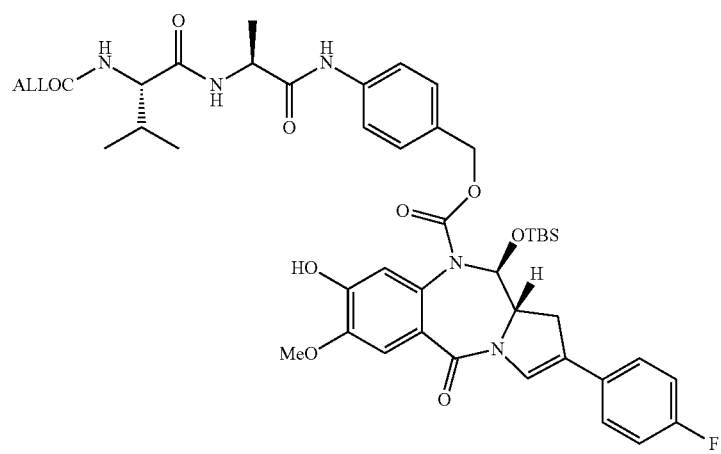
47

(a) Compound 43—allyl ((S)-1-(((S)-1-((4-((((2-((S)-2-(((tert-butyldimethylsilyl)oxy)methyl)-4-(4-fluorophenyl)-2,3-dihydro-1H-pyrrole-1-carbonyl)-4-methoxy-5-((triisopropylsilyl)oxy)phenyl) carbamoyl)oxy)methyl)phenyl)amino)-1-oxopropan-2-yl)amino)-3-methyl-1-oxobutan-2-yl)carbamate Triethylamine (4.34 mL, 31.15 mmol, 2.2 eq) was added to a stirred solution of the amine 35 (8.91 g, 14.16 mmol) and triphosgene (1.51 g, 5.10 mmol, 0.36 eq) in dry tetrahydrofuran (80 mL) at 5° C. (ice bath). The progress of the isocyanate reaction was monitored by periodically removing aliquots from the reaction mixture and quenching with methanol and performing LC/MS analysis. Once the isocyanate formation was complete a solution of the alloc-Val-Ala-PABOH (8.02 g, 21.24 mmol, 1.5 eq) and triethylamine (2.96 mL, 21.24 mmol, 1.5 eq) in dry tetrahydrofuran (80 mL) was rapidly added by injection to the freshly prepared isocyanate. The reaction mixture was allowed to stir at 40° C. for 4 hours. Excess solvent was removed by rotary evaporation under reduced pressure. The resulting residue was subjected to flash column chromatography (silica gel; gradient, 1% methanol to 5% methanol in dichloromethane). (Alternative chromatography conditions using EtOAc and Hexane have also been successful). Pure fractions were collected and combined and excess eluent was removed by rotary evaporation under reduced pressure to give the product 43 (8.78 g, 60%).: LC/MS, method 2, 4.28 min (ES+) m/z (relative intensity) 1032.56 ([M+H]$^+$, 100).

(b) Compound 44—allyl ((S)-1-(((S)-1-((4-((((2-((S)-4-(4-fluorophenyl)-2-(hydroxymethyl)-2,3-dihydro-1H-pyrrole-1-carbonyl)-4-methoxy-5-((triisopropylsilyl)oxy)phenyl)carbamoyl)oxy)methyl)phenyl) amino)-1-oxopropan-2-yl)amino)-3-methyl-1-oxobutan-2-yl)carbamate The TBS ether 43 (8.78 g, 8.51 mmol) was dissolved in a 7:1:2 mixture of acetic acid/tetrahydrofuran/water (56:8:16 mL) and allowed to stir at room temperature. After 16 hours no more starting material was observed by LC/MS. The reaction mixture was diluted with ethyl acetate (250 mL) and washed sequentially with water, saturated aqueous sodium bicarbonate and brine. The organic phase was dried over magnesium sulphate filtered and excess ethyl acetate removed by rotary evaporation under reduced pressure. The resulting residue was subjected to flash column chromatography (silica gel, 2% methanol to 5% in chloroform). Pure fractions were collected and combined and excess eluent was removed by rotary evaporation under reduced pressure to afford the desired product 44 (3.43 mg, 44%). LC/MS, method 2, 3.75 min (ES+) m/z (relative intensity) 918.01 ([M+H]$^{+\cdot}$, 100).

(c) Compound 45—(11S,11aS)-4-((S)-2-((S)-2-(((allyloxy)carbonyl)amino)-3-methylbutanamido)propanamido)benzyl 2-(4-fluorophenyl)-11-hydroxy-7-methoxy-5-oxo-8-((triisopropylsilyl)oxy)-11,11a-dihydro-1H-benzo[e]pyrrolo[1,2-a][1,4]diazepine-10(5H)-carboxylate Dimethyl sulphoxide (0.60 mL, 8.50 mmol, 2.5 eq) was added dropwise to a solution of oxalyl chloride (0.35 mL, 4.08 mmol, 1.2 eq) in dry dichloromethane (30 mL) at −78° C. (dry ice/acetone bath) under an atmosphere of argon. After 10 minutes a solution of 44 (3.12 g, 3.40 mmol) in dry dichloromethane (40 mL) was added slowly with the temperature still at −78° C. After 15 minutes triethylamine (2.37 mL, dried over 4 Å molecular sieves, 17.01 mmol, 5 eq) was added dropwise and the dry ice/acetone bath was removed. The reaction mixture was allowed to reach room temperature and was extracted with cold hydrochloric acid (0.1 M), saturated aqueous sodium bicarbonate and brine. The organic phase was dried over magnesium sulphate, filtered and excess dichloromethane was removed by rotary evaporation under reduced pressure. The resulting residue was subjected to column flash chromatography (silica gel; gradient 0% to 2% methanol in chloroform). Pure fractions were collected and combined and removal of excess eluent by rotary evaporation under reduced pressure afforded the product 45 (2.27 g, 66%). LC/MS, method 2, 3.58 min (ES+) m/z (relative intensity) 916.17 ([M]$^{+\cdot}$, 100).

(d) Compound 46—(11S,11aS)-4-((S)-2-((S)-2-(((allyloxy)carbonyl)amino)-3-methylbutanamido)propanamido)benzyl 11-((tert-butyldimethylsilyl)oxy)-2-(4-fluorophenyl)-7-methoxy-5-oxo-8-((triisopropylsilyl)oxy)-11,11a-dihydro-1H-benzo[e] pyrrolo[1,2-a][1,4]diazepine-10(5H)-carboxylate Tert-butyldimethylsilyltriflate (1.61 mL, 6.99 mmol, 3 eq) was added to a solution of compound 45 (2.13 g, 2.33 mmol) and 2,6-lutidine (1.09 mL, 9.32 mmol, 4 eq) in dry dichloromethane (35 mL) at 0° C. under argon. After 10 minutes, the cold bath was removed and the reaction mixture was stirred at room temperature for 1 hour. The reaction mixture was extracted with water, saturated aqueous sodium bicarbonate and brine. The organic phase was dried over magnesium sulphate, filtered and excess solvent was removed by rotary evaporation under reduced pressure. The resulting residue was subjected to column flash chromatography (silica gel; 50/50 v/v hexane/ethyl acetate). Pure fractions were collected and combined and excess eluent was removed by rotary evaporation under reduced pressure to give the product 46 (1.12 g, 47%).: LC/MS, method 2, 4.30 min (ES+) m/z (relative intensity) 1030.27 ([M]$^{+\cdot}$, 100).

(e) Compound 47—(11S,11aS)-4-((S)-2-((S)-2-(((allyloxy)carbonyl)amino)-3-methylbutanamido)propanamido)benzyl 11-((tert-butyldimethylsilyl)oxy)-2-(4-fluorophenyl)-8-hydroxy-7-methoxy-5-oxo-11, 11a-dihydro-1H-benzo[e]pyrrolo[1,2-a][1,4] diazepine-10(5H)-carboxylate Lithium acetate (110 mg, 1.08 mmol) was added to a solution of compound 46 (1.11 g, 1.08 mmol) in wet dimethylformamide (10 mL, 50:1 DMF/water). After 4 hours, the reaction was complete and the reaction mixture was diluted with ethyl acetate and washed with citric acid (pH~3), water and brine. The organic layer was dried over magnesium sulphate filtered and excess ethyl acetate was removed by rotary evaporation under reduced pressure. The resulting residue was subjected to column flash chromatography (silica gel; gradient, 50/50 to 0/100 v/v hexane/ethyl acetate). Pure fractions were collected and combined and excess eluent was removed by rotary evaporation under reduced pressure to give the product 47 (940 mg, quantitative). LC/MS, method 2, 3.52 min (ES+) m/z (relative intensity) 874.11 ([M+H]$^{+\cdot}$, 100).

Example 9

(a) Compound 48—(11S,11aS)-allyl 8-((5-(((11S,11aS)-10-(((4-(2-(2-(((allyloxy)carbonyl)amino)-3-methylbutanamido)propanamido)benzyl)oxy)carbonyl)-11-((tert-butyldimethylsilyl)oxy)-2-(4-fluorophenyl)-7-methoxy-5-oxo-5,10,11,11a-tetrahydro-1H-benzo[e]pyrrolo[1,2-a][1,4]diazepin-8-yl)oxy)pentyl)oxy)-11-((tert-butyldimethylsilyl)oxy)-2-(4-fluorophenyl)-7-methoxy-5-oxo-11,11a-dihydro-1H-benzo[e]pyrrolo[1,2-a][1,4]diazepine-10(5H)-carboxylate

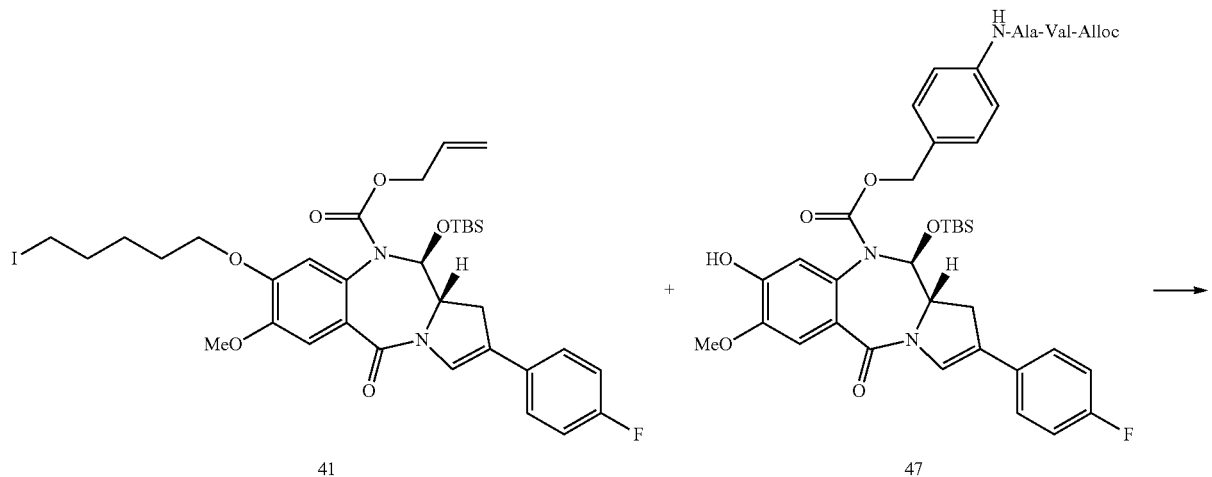

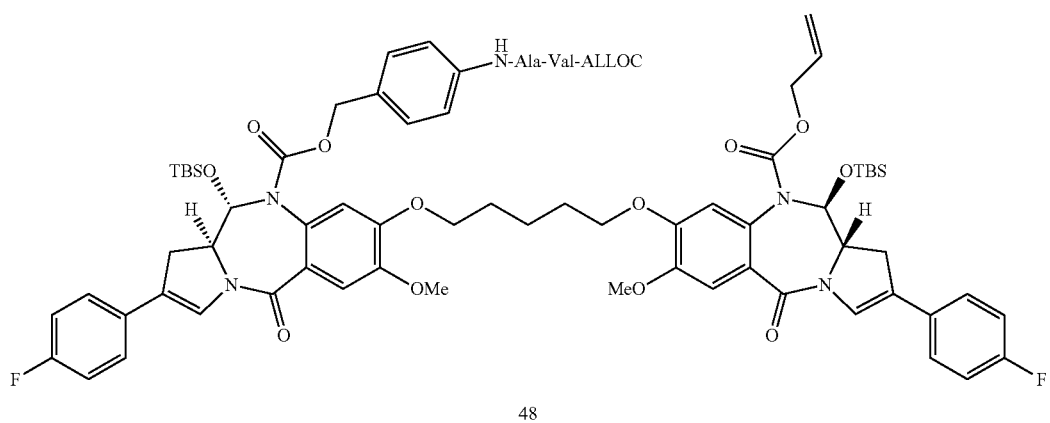

48

Potassium carbonate (63 mg, 0.458 mmol, 1 eq) was added to a solution of 41 (429 mg, 0.572 mmol, 1 eq) and phenol 47 (500 mg, 0.572 mmol) in dry acetone (5 mL). The reaction was stirred 48 hours at 60° C. Acetone was removed by rotary evaporation under reduced pressure. The resulting residue was subjected to flash column chromatography (silica gel; 66% ethyl acetate in hexane to 100% ethyl acetate). Pure fractions were collected and combined and excess eluent was removed by rotary evaporation under reduced pressure to give the product 48 (323 mg, 38%). LC/MS, method 2, 4.22 min (ES+) m/z (relative intensity) 1497.16 ([M+H]$^+$, 100).

(b) Compound 49—(11S,11aS)-allyl 8-(3-(((11S, 11aS)-10-(((4-(2-(1-((1-(allyloxy)-4-methyl-1,2-dioxopentan-3-yl)amino)-1-oxopropan-2-yl)hydrazinyl)benzyl)oxy)carbonyl)-11-((tert-butyldimethylsilyl)oxy)-2-(4-fluorophenyl)-7-methoxy-5-oxo-5,10,11,11a-tetrahydro-1H-benzo[e]pyrrolo[1,2-a][1,4]diazepin-8-yl)oxy)propoxy)-11-((tert-butyldimethylsilyl)oxy)-2-(4-fluorophenyl)-7-methoxy-5-oxo-11,11a-dihydro-1H-benzo[e]pyrrolo[1,2-a][1,4]diazepine-10(5H)-carboxylate spray ionisation. Mobile phase A—0.1% Acetic acid in water. Mobile Phase B—0.1% in acetonitrile. Flow rate of 1.00 ml/min. Gradient from 5% B rising up to 95% B over 3 minutes, remaining at 95% B for 1 minute and then back down to 5% B over 6 seconds. The total run time is 5 minutes. Column: Phenomenex Gemini-NX 3 µm C18, 30×2.00 mm. Chromatograms based on UV detection at 254 nm. Mass Spectra were achieved using the MS in positive mode. Proton NMR chemical shift values were measured on the delta scale at 400 MHz using a Bruker AV400. The following abbreviations have been used: s, singlet; d, doublet; t, triplet; q, quar-

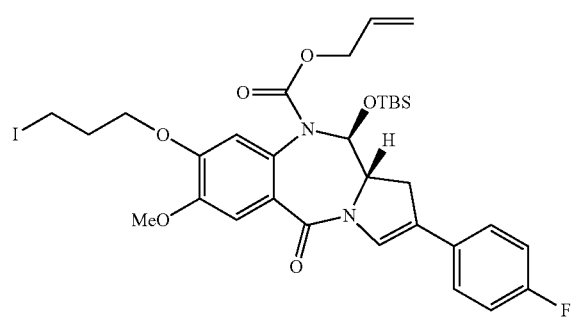

42

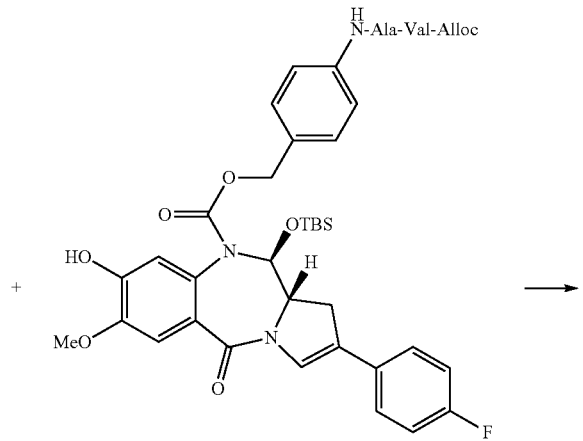

47

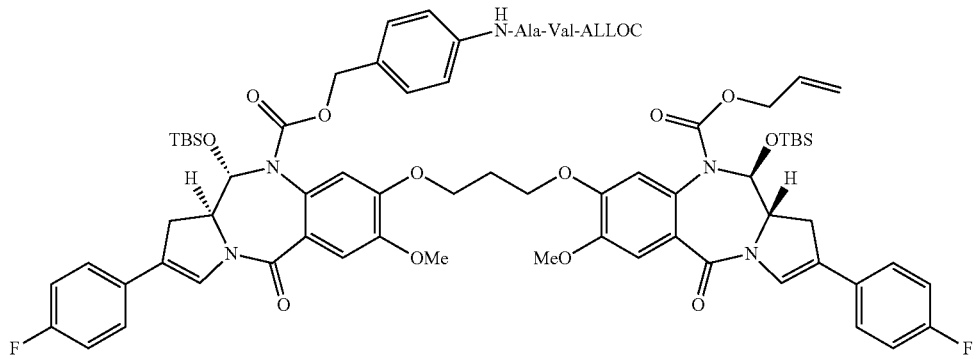

49

Potassium carbonate (50.6 mg, 0.366 mmol, 0.8 eq) was added to a solution of 42 (497 mg, 0.686 mmol, 1.5 eq) and phenol 47 (400 mg, 0.457 mmol) in dry acetone (40 mL). The reaction was stirred 8 hours at 70° C. The LC/MS showed that all the starting material was not consumed, so the reaction was allowed to stir overnight at room temperature and stirred for an additional 2 hours the next day. Acetone was removed by rotary evaporation under reduced pressure. The resulting residue was subjected to flash column chromatography (silica gel; 80% ethyl acetate in hexane to 100% ethyl acetate). Pure fractions were collected and combined and excess eluent was removed by rotary evaporation under reduced pressure to give the product 49 (440 mg, 66%). LC/MS, method 2, 4.17 min (ES+) m/z (relative intensity) 1467.69 ([M+H]$^{+\cdot}$, 50).

General Experiment for Following Examples

LCMS data were obtained using an Agilent 1200 series LC/MS with an Agilent 6110 quadrupole MS, with Electrotet; m, multiplet; br, broad. Coupling constants are reported in Hz. Unless otherwise stated, column chromatography (by the flash procedure) were performed on Merck Kieselgel silica (Art. 9385). Mass spectroscopy (MS) data were collected using a Waters Micromass LCT instrument coupled to a Waters 2795 HPLC separations module. Thin Layer Chromatography (TLC) was performed on silica gel aluminium plates (Merck 60, $F_{254}$). All other chemicals and solvents were purchased from Sigma-Aldrich or Fisher Scientific and were used as supplied without further purification.

Optical rotations were measured on an ADP 220 polarimeter (Bellingham Stanley Ltd.) and concentrations (c) are given in g/100 mL. Melting points were measured using a digital melting point apparatus (Electrothermal). IR spectra were recorded on a Perkin-Elmer Spectrum 1000 FT IR Spectrometer. $^1$H and $^{13}$C NMR spectra were acquired at 300 K using a Bruker Avance NMR spectrometer at 400 and 100 MHz, respectively. Chemical shifts are reported relative to TMS (δ=0.0 ppm), and signals are designated as s (singlet), d (doublet), t (triplet), dt (double triplet), dd (doublet of doublets), ddd (double doublet of doublets) or m (multiplet), with coupling constants given in Hertz (Hz). Mass spectroscopy (MS) data were collected using a Waters Micromass ZQ instrument coupled to a Waters 2695 HPLC with a Waters 2996 PDA. Waters Micromass ZQ parameters used were: Capillary (kV), 3.38; Cone (V), 35; Extractor (V), 3.0; Source temperature (° C.), 100; Desolvation Temperature (° C.), 200; Cone flow rate (L/h), 50; De-solvation flow rate (L/h), 250. High-resolution mass spectroscopy (HRMS) data were recorded on a Waters Micromass QTOF Global in positive W-mode using metal-coated borosilicate glass tips to introduce the samples into the instrument. Thin Layer Chromatography (TLC) was performed on silica gel aluminium plates (Merck 60, $F_{254}$), and flash chromatography utilised silica gel (Merck 60, 230-400 mesh ASTM). Except for the HOBt (NovaBiochem) and solid-supported reagents (Argonaut), all other chemicals and solvents were purchased from Sigma-Aldrich and were used as supplied without further purification. Anhydrous solvents were prepared by distillation under a dry nitrogen atmosphere in the presence of an appropriate drying agent, and were stored over 4 Å molecular sieves or sodium wire. Petroleum ether refers to the fraction boiling at 40-60° C.

General LC/MS conditions: The HPLC (Waters Alliance 2695) was run using a mobile phase of water (A) (formic acid 0.1%) and acetonitrile (B) (formic acid 0.1%). Gradient: initial composition 5% B over 1.0 min then 5% B to 95% B within 3 min. The composition was held for 0.5 min at 95% B, and then returned to 5% B in 0.3 minutes. Total gradient run time equals 5 min. Flow rate 3.0 mL/min, 400 µL was split via a zero dead volume tee piece which passes into the mass spectrometer. Wavelength detection range: 220 to 400 nm. Function type: diode array (535 scans). Column: Phenomenex® Onyx Monolithic C18 50×4.60 mm Synthesis of Key Intermediates

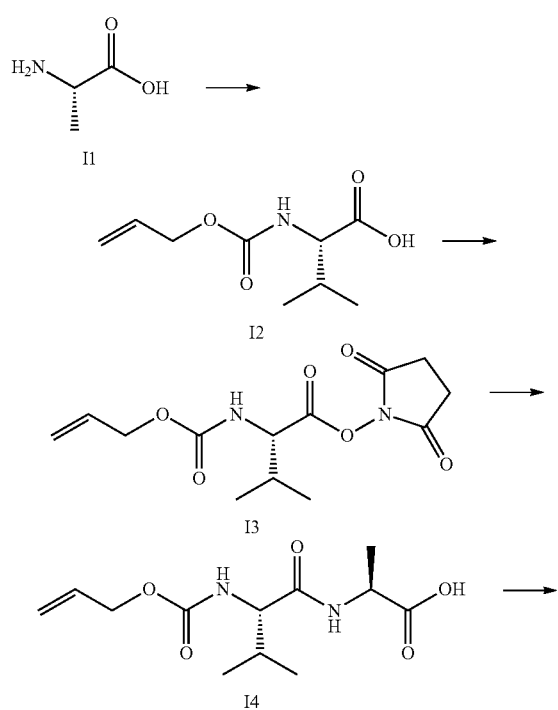

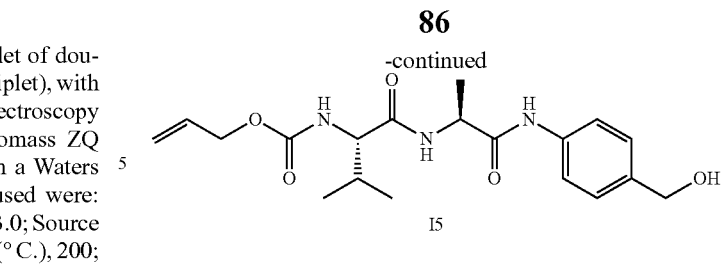

(a) (S)-2-(allyloxycarbonylamino)-3-methylbutanoic acid (I2)

Allyl chloroformate (36.2 ml, 340.59 mmol, 1.2 eq) was added dropwise to a stirred solution of L-valine (I1)(33.25 g, 283.82 mmol, 1.0 eq) and potassium carbonate (59.27 g, 425.74 mmol, 1.5 eq) in water (650 mL) and THF (650 mL). The reaction mixture was stirred at room temperature for 18 hours, then the solvent was concentrated under reduced pressure and the remaining solution extracted with diethyl ether (3×100 mL). The aqueous portion was acidified to pH 2 with conc. HCl and extracted with DCM (3×100 mL). The combined organics were washed with brine, dried over $MgSO_4$, filtered and concentrated under reduced pressure to afford the product as a colourless oil (57.1 g, assumed 100% yield). LC/MS (1.966 min (ES+)), m/z: 202.1 [M+H]+. $^1$H NMR (400 MHz, DMSO-$d_6$) δ 12.57 (br s, 1H), 7.43 (d, 1H, J=8.6 Hz), 5.96-5.86 (m, 1H), 5.30 (ddd, 1H, J=17.2, 3.4, 1.7 Hz), 5.18 (ddd, 1H, J=10.4, 2.9, 1.6 Hz), 4.48 (dt, 2H, J=5.3, 1.5 Hz), 3.85 (dd, 1H, J=8.6, 6.0 Hz), 2.03 (oct, 1H, J=6.6 Hz), 0.89 (d, 3H, J=6.4 Hz), 0.87 (d, 3H, J=6.5 Hz), (b) (S)-2,5-dioxopyrrolidin-1-yl 2-(allyloxycarbonylamino)-3-methylbutanoate (I3)

To a stirred solution of the protected acid 12 (60.6 g, 301.16 mmol, 1.0 eq) and N-hydroxysuccinimide (34.66 g, 301.16 mmol, 1.0 eq) in dry THF (800 mL) was added dicyclohexylcarbodiimide (62.14 g, 301.16 mmol, 1 eq). The reaction was stirred for 18 hours at room temperature. The reaction mixture was then filtered, the solid washed with THF and the combined filtrate was concentrated under reduced pressure. The residue was re-dissolved in DCM and left to stand at 0° C. for 30 minutes. The suspension was filtered and washed with cold DCM. Concentration of the filtrate under reduced pressure afforded the product as a viscous colourless oil (84.7 g, assumed 100% yield) which was used in the next step without further purification. LC/MS (2.194 min (ES+)), m/z: 321.0 [M+Na]+. $^1$H NMR (400 MHz, DMSO-$d_6$) δ 8.0 (d, 1H, J=8.3 Hz), 5.97-5.87 (m, 1H), 5.30 (ddd, 1H, J=17.2, 3.0, 1.7 Hz), 5.19 (ddd, 1H, J=10.4, 2.7, 1.4 Hz), 4.52 (dt, 2H, J=5.3, 1.4 Hz), 4.32 (dd, 1H, J=8.3, 6.6 Hz), 2.81 (m, 4H), 2.18 (oct, 1H, J=6.7 Hz), 1.00 (d, 6H, J=6.8 Hz), (c) (S)-2-((S)-2-(allyloxycarbonylamino)-3-methylbutanamido)propanoic acid (I4)

A solution of succinimide ester 13(12.99 g, 43.55 mmol, 1.0 eq) in THF (50 mL) was added to a solution of L-alanine (4.07 g, 45.73 mmol, 1.05 eq) and $NaHCO_3$ (4.02 g, 47.90 mmol, 1.1 eq) in THF (100 mL) and $H_2O$ (100 mL). The mixture was stirred at room temperature for 72 hours when the THF was removed under reduced pressure. The pH was adjusted to 3-4 with citric acid to precipitate a white gum. After extraction with ethyl acetate (6×150 mL), the combined organics were washed with $H_2O$ (200 mL), dried over $MgSO_4$, filtered and concentrated under reduced pressure.

Trituration with diethyl ether afforded the product as a white powder which was collected by filtration and washed with diethyl ether (5.78 g, 49%). LC/MS (1.925 min (ES$^+$)), m/z: 273.1 [M+H]$^+$. $^1$H NMR (400 MHz, DMSO-d$_6$) δ 12.47 (br s, 1H), 8.17 (d, 1H, J=6.8 Hz), 7.16 (d, 1H, J=9.0 Hz), 5.95-5.85 (m, 1H), 5.29 (dd, 1H, J=17.2, 1.7 Hz), 5.17 (dd, 1H, J=10.4, 1.5 Hz), 4.46 (m, 2H), 4.18 (quin, 1H, J=7.2 Hz), 3.87 (dd, 1H, J=9.0, 7.1 Hz), 1.95 (oct, 1H, J=6.8 Hz), 1.26 (d, 3H, J=7.3 Hz), 0.88 (d, 3H, J=6.8 Hz), 0.83 (d, 3H, J=6.8 Hz).

(d) Allyl (S)-1-((S)-1-(4-(hydroxymethyl)phenylamino)-1-oxopropan-2-ylamino)-3-methyl-1-oxobutan-2-ylcarbamate (I5)

EEDQ (5.51 g, 22.29 mmol, 1.05 eq) was added to a solution of p-aminobenzyl alcohol (2.74 g, 22.29 mmol, 1.05 eq) and acid 14 (5.78 g, 21.23 mmol, 1 eq) in dry THF (100 mL). and stirred at room temperature for 72 hours. The reaction mixture was then concentrated under reduced pressure and the resulting brown solid was triturated with diethyl ether and filtered with subsequent washing with an excess of diethyl ether to afford the product as an off-white solid (7.1 g, 88%). LC/MS (1.980 min (ES$^+$)), m/z: 378.0 [M+H]$^+$. $^1$H NMR (400 MHz, DMSO-d$_6$) δ 9.89 (br s, 1H), 8.13 (d, 1H, J=7.0 Hz), 7.52 (d, 2H, J=8.5 Hz), 7.26 (m, 1H), 7.23 (d, 2H, J=8.5 Hz), 5.91 (m, 1H), 5.30 (m, 1H), 5.17 (m, 1H), 4.46 (m, 2H), 5.09 (t, 1H, J=5.6 Hz), 4.48 (m, 2H), 4.42 (m, 3H), 3.89 (dd, 1H, J=8.6, 6.8 Hz), 1.97 (m, 1H), 1.30 (d, 3H, J=7.1 Hz), 0.88 (d, 3H, J=6.8 Hz), 0.83 (d, 3H, J=6.7 Hz).

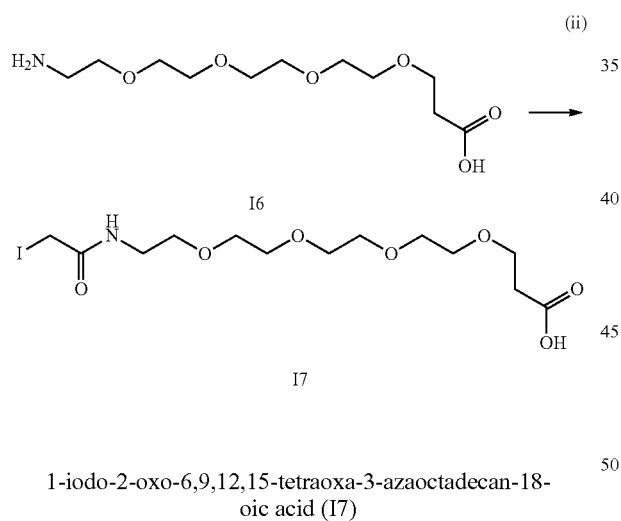

(ii)

1-iodo-2-oxo-6,9,12,15-tetraoxa-3-azaoctadecan-18-oic acid (I7)

A solution of iodoacetic anhydride (0.250 g, 0.706 mmol, 1.1 eq) in dry DCM (1 mL) was added to amino-PEG$_{(4)}$-acid I6 (0.170 g, 0.642 mmol, 1.0 eq) in DCM (1 mL). The mixture was stirred in the dark at room temperature overnight. The reaction mixture was washed with 0.1 M HCl, water, dried over MgSO$_4$, filtered and concentrated under reduced pressure. The residue was purified by flash chromatography (silica gel, 3% MeOH and 0.1% formic acid in chloroform to 10% MeOH and 0.1% formic acid in chloroform) to afford the product as an orange oil (0.118 g, 42%). LC/MS (1.623 min (ES$^+$)), m/z: 433.98 [M+H]$^+$. $^1$H NMR (400 MHz, CDCl$_3$) δ 8.069 (s, 1H), 7.22 (br s, 1H), 3.79 (t, 2H, J=5.8 Hz), 3.74 (s, 2H), 3.72-3.58 (m, 14H), 3.50-3.46 (m, 2H), 2.62 (t, 2H, J=5.8 Hz).

Example 10

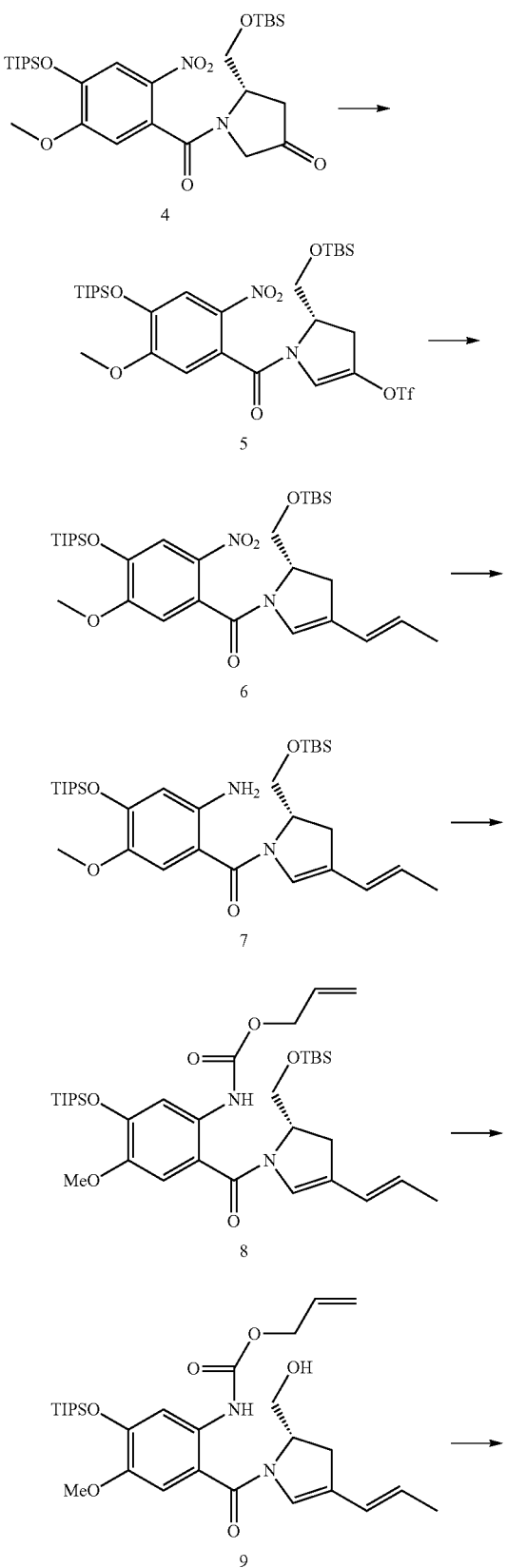

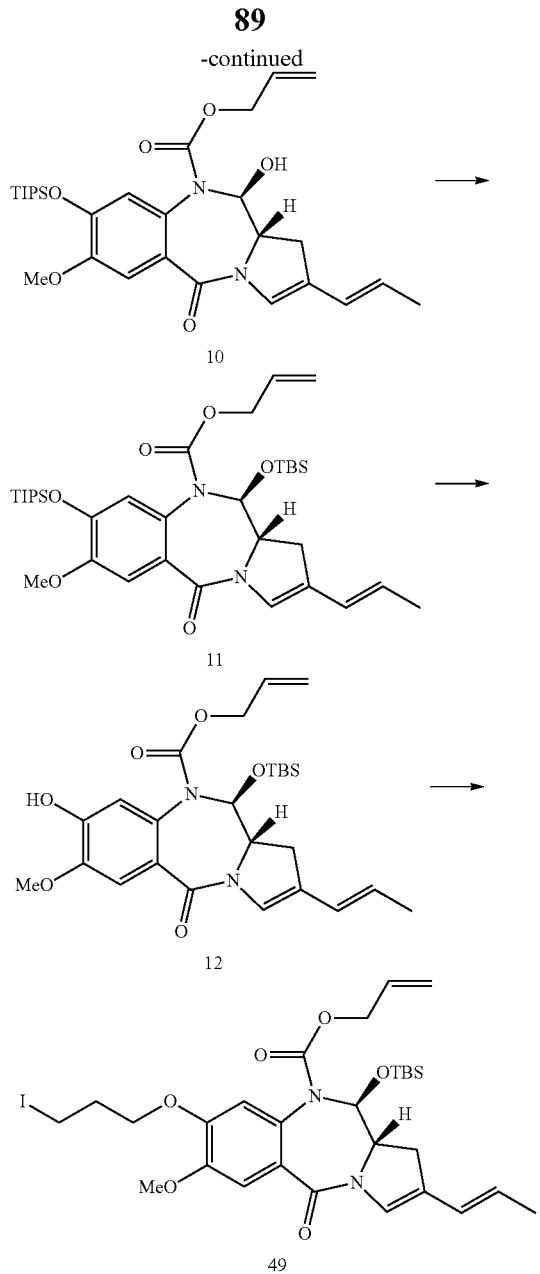

(a) (S)-5-((tert-butyldimethylsilyloxy)methyl)-1-(5-methoxy-2-nitro-4-(triisopropylsilyloxy)benzoyl)-4,5-dihydro-1H-pyrrol-3-yl trifluoromethanesulfonate (5)

Triflic anhydride (28.4 g, 100.0 mmol, 3.0 eq) was added dropwise, over 25 mins, to a vigorously stirred solution of the ketone 4 (19.5 g, 30.0 mmol, 1.0 eq) in DCM (550 mL) containing 2,6-lutidine (14.4 g, 130.0 mmol, 4.0 eq) at −50° C. The reaction mixture was stirred for 1.5 hours when LC/MS indicated complete reaction. The organic phase was washed successively with water (100 mL), saturated sodium bicarbonate (150 mL), brine (50 mL), and the organic phase was dried over MgSO$_4$, filtered and concentrated under reduced pressure. The residue was purified by flash chromatography (silica gel, 90/10 v/v n-hexane/EtOAc) to afford the product as a pale yellow oil (19.5 g, 82%). LC/MS (4.391 min (ES$^+$)), m/z: 713.25 [M+H]$^+$. $^1$H NMR (400 MHz, CDCl$_3$) δ 7.68 (s, 1H), 6.72 (s, 1H), 6.02 (t, 1H, J=1.9 Hz), 4.75 (m, 1H), 4.05 (m, 2H), 3.87 (s, 3H), 3.15 (ddd, 1H, J=16.2, 10.3, 2.3 Hz), 2.96 (ddd, 1H, J=16.2, 4.0, 1.6 Hz), 1.28-1.21 (m, 3H), 1.07 (d, 18H, J=7.2 Hz), 0.88 (s, 9H), 0.09 (s, 3H), 0.08 (s, 3H).

(b) (S,E)-(2-((tert-butyldimethylsilyloxy)methyl)-4-(prop-1-enyl)-2,3-dihydro-1H-pyrrol-1-yl)(5-methoxy-2-nitro-4-(triisopropylsilyloxy)phenyl)methanone (6)

Tetrakis(triphenylphosphine)palladium(0) (0.41 g, 0.35 mmol, 0.03 eq) was added to a mixture of the triflate 5 (8.4 g, 11.8 mmol, 1.0 eq), E-1-propene-1-ylboronic acid (1.42 g, 16.5 mmol, 1.4 eq) and potassium phosphate (5.0 g, 23.6 mmol, 2.0 eq) in dry dioxane (60 mL) under a nitrogen atmosphere. The mixture was stirred at 25° C. for 120 mins when LC/MS indicated complete reaction. Ethyl acetate (120 mL) and water (120 mL) were added, the organic phase was removed, washed with brine (20 mL), dried over MgSO$_4$, filtered and concentrated under reduced pressure. The residue was purified by flash chromatography (silica gel, 95/5 v/v n-hexane/EtOAc to 90/10 v/v n-hexane/EtOAc) to afford the product as a yellow foam (4.96 g, 70%). LC/MS (4.477 min (ES$^+$)), m/z: 605.0 [M+H]$^+$. $^1$H NMR (400 MHz, CDCl$_3$) δ 7.67 (s, 1H), 6.74 (s, 1H), 5.93 (d, 1H, J=15.4 Hz), 5.67 (s, 1H), 4.65 (m, 1H), 4.04 (m, 2H), 3.86 (s, 3H), 2.85 (m, 1H), 2.71 (m, 1H), 1.72 (dd, 3H, J=6.8, 1.0 Hz), 1.30-1.22 (m, 3H), 1.07 (d, 18H, J=7.2 Hz), 0.87 (s, 9H), 0.08 (s, 3H), 0.07 (s, 3H).

(c) (S,E)-(2-amino-5-methoxy-4-(triisopropylsilyloxy)phenyl)(2-((tert-butyldimethylsilyloxy)methyl)-4-(prop-1-enyl)-2,3-dihydro-1H-pyrrol-1-yl)methanone (7)

Zinc dust (22.0 g, 0.33 mol, 37 eq) was added, in portions over 20 mins, to a solution of the propenyl intermediate 6 (5.5 g, 9.1 mmol, 1.0 eq) in 5% v/v formic acid/ethanol (55 mL), using an ice bath to maintain the temperature between 25-30° C. After 30 mins, the reaction mixture was filtered through a short bed of Celite®. The Celite® was washed with ethyl acetate (65 mL) and the combined organics were washed successively with water (35 mL), saturated sodium bicarbonate (35 mL) and brine (10 mL). The organic phase was dried over MgSO$_4$, filtered and concentrated under reduced pressure. The residue was purified by flash chromatography (silica gel, 90/10 v/v n-hexane/EtOAc) to afford the product as a pale yellow oil (3.6 g, 69.0%). LC/MS (4.439 min (ES$^+$)), m/z: 575.2 [M+H]$^+$. $^1$H NMR (400 MHz, CDCl$_3$) δ 6.75 (m, 1H), 6.40 (br s, 1H), 6.28 (m, 1H), 6.11 (d, 1H, J=15.4 Hz), 5.53 (m, 1H), 4.67 (m, 1H), 4.36 (m, 2H), 3.93 (br s, 1H), 3.84 (br s, 1H), 3.73 (s, 3H), 2.86 (dd, 1H, J=15.7, 10.4 Hz), 2.73 (dd, 1H, J=15.9, 4.5 Hz), 1.80 (dd, 3H, J=6.8, 1.3 Hz), 1.35-1.23 (m, 3H), 1.12 (d, 18H, J=7.3 Hz), 0.89 (s, 9H), 0.08 (s, 3H), 0.07 (s, 3H).

(d) (S,E)-allyl 2-(2-((tert-butyldimethylsilyloxy)methyl)-4-(prop-1-enyl)-2,3-dihydro-1H-pyrrole-1-carbonyl)-4-methoxy-5-(triisopropylsilyloxy)phenylcarbamate (8)

Allyl chloroformate (0.83 g, 6.88 mmol, 1.1 eq) was added to a solution of the amine 7 (3.6 g, 6.26 mmol, 1.0 eq) in dry DCM (80 mL) containing dry pyridine (1.09 g, 13.77 mmol, 2.2 eq) at −78° C. The dry ice was removed and the reaction mixture allowed to warm to room temperature. After stirring for a further 15 minutes, LC/MS indicated complete reaction. The organic phase was washed successively with 0.01N HCl (50 mL), saturated sodium bicarbonate (50 mL), brine (10 mL), dried over MgSO$_4$, filtered and concentrated under reduced pressure to leave a pale yellow oil which was used in the next step without further purification (4.12 g, assumed 100% yield). LC/MS (4.862 min (ES$^+$)), m/z: 659.2 [M+H]$^+$.

(e) (S,E)-allyl 2-(2-(hydroxymethyl)-4-(prop-1-enyl)-2,3-dihydro-1H-pyrrole-1-carbonyl)-4-methoxy-5-(triisopropylsilyloxy)phenylcarbamate (9)

The crude intermediate 8 (assumed 100% yield, 4.12 g, 6.25 mmol, 1.0 eq) was dissolved in a mixture of acetic acid (70 mL), methanol (10 mL), THF (10 mL) and water (20 mL) and allowed to stir at room temperature. After 6 hours the reaction mixture was diluted with ethyl acetate (500 mL) and washed successively with water (2×500 mL), saturated sodium bicarbonate (300 mL) and brine (50 mL). The organic phase was dried over MgSO$_4$, filtered and concentrated under reduced pressure. The residue was purified by flash chromatography (silica gel, 1/99 v/v methanol/DCM to 5/95 v/v methanol/DCM) to afford the product as a yellow oil and a further 1 g of unreacted starting material was recovered. This material was subjected to the same reaction conditions as above, but was left stirring for 16 hours. After work up and purification, additional product was isolated (2.7 g, 79%, 2 steps) LC/MS (3.742 min (ES$^+$)), m/z: 545.2 [M+H]$^+$. $^1$H NMR (400 MHz, CDCl$_3$) δ 8.38 (m, 1H), 7.72 (m, 1H), 6.81 (s, 1H), 6.37 (m, 1H), 6.10 (d, 1H, J=15.8 Hz), 5.97 (m, 1H), 5.53 (m, 1H), 5.36 (ddd, 1H, J=17.2, 3.1, 1.5 Hz), 5.25 (ddd, 1H, J=10.4, 2.5, 1.3 Hz), 4.78 (m, 1H), 4.65 (dt, 2H, J=5.7, 1.3 Hz), 3.84 (m, 3H), 3.79 (s, 3H), 3.04 (dd, 1H, J=16.7, 10.5 Hz), 2.40 (dd, 1H, J=16.0, 4.5 Hz), 1.82 (dd, 3H, J=6.8, 1.0 Hz), 1.36-1.26 (m, 3H), 1.14 (d, 18H, J=7.3 Hz).

(f) (11S,11aS)-allyl 11-hydroxy-7-methoxy-5-oxo-2-((E)-prop-1-enyl)-8-(triisopropylsilyloxy)-11,11a-dihydro-1H-benzo[e]pyrrolo[1,2-a][1,4]diazepine-10(5H)-carboxylate (10)

Dry dimethyl sulfoxide (1.16 g, 14.87 mmol, 3.0 eq) was added dropwise to a solution of oxalyl chloride (0.94 g, 7.43 mmol, 1.5 eq) in DCM (25 mL) at –78° C. under an atmosphere of nitrogen. Maintaining the temperature at –78° C., after 10 mins a solution of the primary alcohol 9 (2.7 g, 4.96 mmol, 1.0 eq) in DCM (20 mL) was added dropwise. After a further 15 mins, dry triethylamine (2.5 g, 24.78 mmol, 5.0 eq) was added, and the reaction mixture allowed to warm to room temperature. The reaction mixture was washed successively with cold 0.1N HCl (50 mL), saturated sodium hydrogen carbonate (50 mL) and brine (10 mL) and the organic layer was dried over MgSO$_4$, filtered and concentrated under reduced pressure to afford the product as a yellow oil which was used in the next step without further purification (2.68 g, assumed 100% yield). LC/MS (3.548 min (ES$^+$)), m/z: 543.2 [M+H]$^+$.

(g) (11S,11aS)-allyl 11-(tert-butyldimethylsilyloxy)-7-methoxy-5-oxo-2-((E)-prop-1-enyl)-8-(triisopropylsilyloxy)-11,11a-dihydro-1H-benzo[e]pyrrolo[1,2-a][1,4]diazepine-10(5H)-carboxylate (11)

Tert-butyldimethylsilyltrifluoromethane sulfonate (3.93 g, 14.87 mmol, 3.0 eq) was added to a solution of the carbinolamine 10 (assumed 100% yield, 2.68 g, 4.96 mmol, 1.0 eq) and 2,6-lutidine (2.12 g, 19.83 mmol, 4.0 eq) in dry DCM (40 mL) at 0° C. under an atmosphere of nitrogen. After 10 minutes, the reaction mixture was allowed to warm to room temperature and stirred for a further 60 minutes. The organic phase was washed successively with water (10 mL), saturated sodium bicarbonate (10 mL) and brine (5 mL), dried over MgSO$_4$, filtered and concentrated under reduced pressure. The residue was purified by flash chromatography (silica gel, chloroform to 2/98 v/v Methanol/chloroform) to afford the product as a yellow oil (2.0 g, 63%, 2 steps). LC/MS (4.748 min (ES$^+$)), m/z: 657.2 [M+H]$^+$. $^1$H NMR (400 MHz, CDCl$_3$) δ 7.19 (s, 1H), 6.86 (m, 1H), 6.66 (s, 1H), 6.22 (d, 1H, J=15.4 Hz), 5.81 (d, 1H, J=8.8 Hz), 5.78 (m, 1H), 5.48 (m, 1H), 5.11 (d, 1H, J=5.0 Hz), 5.08 (m, 1H), 4.58 (dd, 1H, J=13.4, 5.4 Hz), 4.35 (dd, 1H, J=13.2, 5.7 Hz), 3.83 (s, 3H), 3.76 (s, 1H), 3.00 (dd, 1H, J=15.6, 11.0 Hz), 2.53 (m, 1H), 1.81 (dd, 3H, J=6.8, 0.9 Hz), 1.30-1.18 (m, 3H), 1.08 (d, 9H, J=2.3 Hz), 1.06 (d, 9H, J=2.3 Hz), 0.86 (s, 9H), 0.25 (s, 3H), 0.18 (s, 3H).

(h) (11S,11aS)-allyl 11-(tert-butyldimethylsilyloxy)-8-hydroxy-7-methoxy-5-oxo-2-((E)-prop-1-enyl)-11,11a-dihydro-1H-benzo[e]pyrrolo[1,2-a][1,4]diazepine-10(5H)-carboxylate (12)

Lithium acetate dihydrate (0.31 g, 3.04 mmol, 1.0 eq) was added to a solution of the diazepine 11 (2.0 g, 3.04 mmol, 1.0 eq) in wet DMF (20 mL) at 25° C. and stirred for 4 hours. The reaction mixture was diluted with ethyl acetate (200 mL) and washed successively with 0.1M citric acid (50 mL, pH 3), water (50 mL) and brine (10 mL), dried over MgSO$_4$, filtered and concentrated under reduced pressure. The residue was purified by flash chromatography (silica gel, 50/50 v/v n-hexane/EtOAc to 25/75 v/v n-hexane/EtOAc) to afford the product as a pale yellow solid (0.68 g, 45%). LC/MS (3.352 min (ES$^+$)), m/z: 501.1 [M+H]$^+$. $^1$H NMR (400 MHz, CDCl$_3$) δ 7.02 (s, 1H), 6.66 (m, 1H), 6.53 (s, 1H), 6.03 (d, 1H, J=15.5 Hz), 5.80 (s, 1H), 5.63 (d, 1H, J=8.9 Hz), 5.55 (m, 1H), 5.29 (m, 1H), 4.87 (m, 2H), 4.39 (dd, 1H, J=13.5, 4.2 Hz), 4.20 (dd, 1H, J=13.2, 5.7 Hz), 3.73 (s, 3H), 3.59 (m, 1H), 2.81 (dd, 1H, J=16.1, 10.5 Hz), 2.35 (d, 1H, J=15.7 Hz), 1.61 (d, 3H, J=6.4 Hz), 0.67 (s, 9H), 0.05 (s, 3H), 0.00 (s, 3H).

(i) (11S,11aS)-allyl 11-(tert-butyldimethylsilyloxy)-8-(3-iodopropoxy)-7-methoxy-5-oxo-2-((E)-prop-1-enyl)-11,11a-dihydro-1H-benzo[e]pyrrolo[1,2-a][1,4]diazepine-10(5H)-carboxylate (49)

Diiodopropane (0.295 g, 1.00 mmol, 5.0 eq) and potassium carbonate (0.028 g, 0.20 mmol, 1.0 eq) were added to a solution of the phenol 12 (0.100 g, 0.020 mmol, 1.0 eq) in dry acetone (5 mL). The reaction mixture was heated at 60° C. for 6 hours when LC/MS showed complete reaction. The reaction mixture was concentrated to dryness under reduced pressure and the residue was purified by flash chromatography (silica gel, 75/25 v/v n-hexane/EtOAc to 50/50 v/v n-hexane/EtOAc) to afford the product as a colourless oil (0.074 g, 56%). LC/MS (3.853 min (ES$^+$)), m/z: 669.0 [M+H]$^+$. $^1$H NMR (400 MHz, CDCl$_3$) δ 7.26 (s, 1H), 6.90 (s, 1H), 6.68 (s, 1H), 6.24 (d, 1H, J=15.3 Hz), 5.87 (d, 1H, J=8.9 Hz), 5.78 (m, 1H), 5.53 (m, 1H), 5.12 (m, 2H), 4.65 (m, 2H), 4.41 (m, 1H), 4.11 (m, 1H), 3.93 (s, 3H), 3.81 (m, 1H), 3.40 (t, 2H, J=6.7 Hz), 3.05 (dd, 1H, J=16.3, 10.1 Hz), 2.57 (m, 1H), 2.34 (m, 2H), 1.84 (d, 3H, J=6.6 Hz), 0.92 (s, 9H), 0.28 (s, 3H), 0.26 (s, 3H).

Example 11
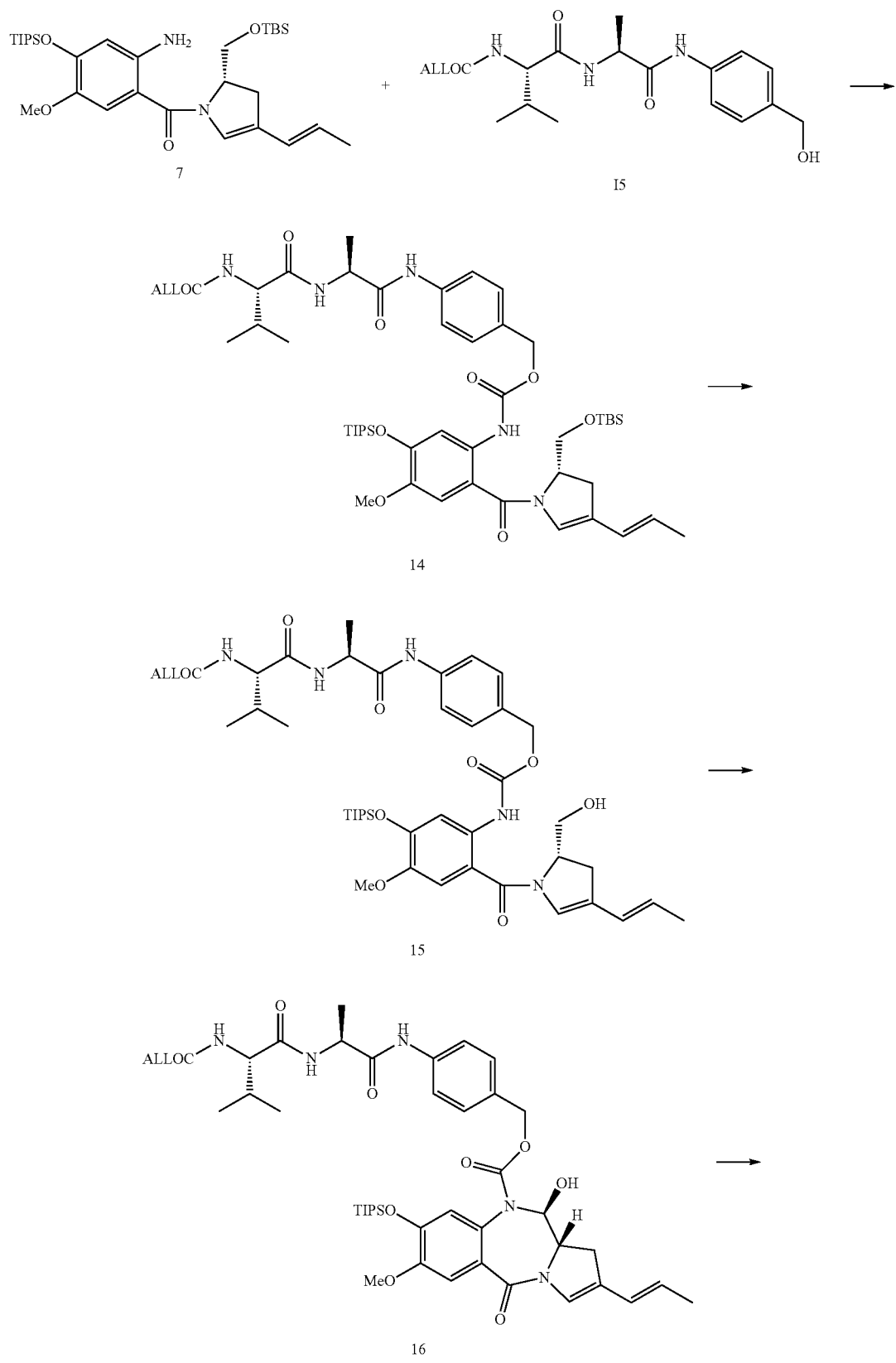

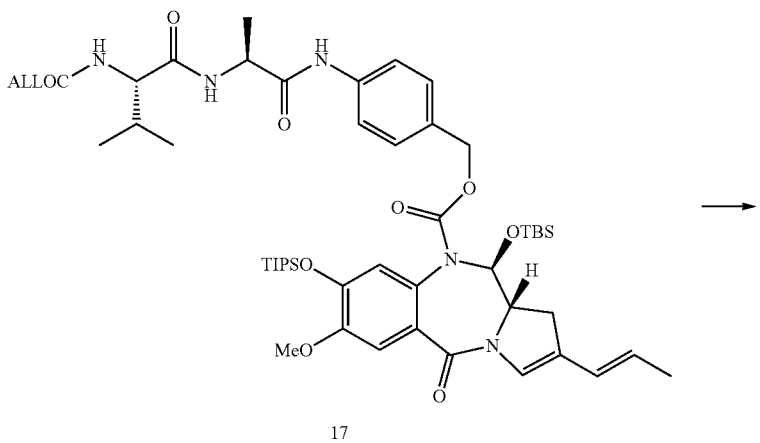

17

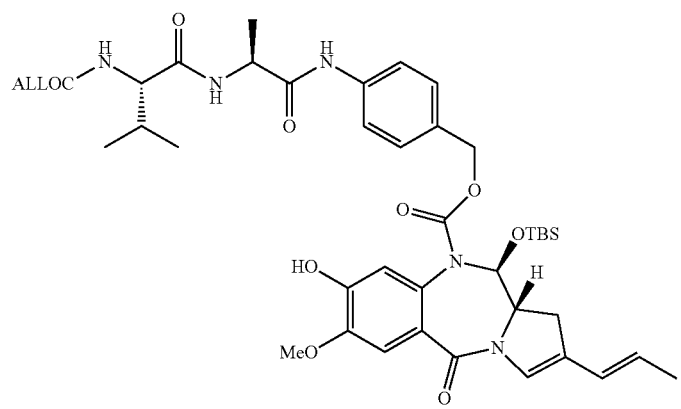

18

(a) Allyl ((S)-1-(((S)-1-((4-((((2-((S)-2-(((tert-butyldimethylsilyl)oxy)methyl)-4-((E)-prop-1-en-1-yl)-2,3-dihydro-1H-pyrrole-1-carbonyl)-4-methoxy-5-((triisopropylsilyl)oxy)phenyl)carbamoyl)oxy)methyl)phenyl)amino)-1-oxopropan-2-yl)amino)-3-methyl-1-oxobutan-2-yl)carbamate (14)

Triethylamine (0.256 mL, 1.84 mmol, 2.2 eq) was added to a stirred solution of the amine 7 (0.480 g, 0.835 mmol, 1.0 eq) and triphosgene (0.089 g, 0.301 mmol, 0.36 eq) in dry THF (15 mL) at 5° C. (ice bath). The progress of the isocyanate reaction was monitored by periodically removing aliquots from the reaction mixture and quenching with methanol and performing LCMS analysis. Once the isocyanate reaction was complete a solution of Alloc-Val-Ala-PABOH 15 (0.473 g, 1.25 mmol, 1.5 eq) and triethylamine (0.174 mL, 1.25 mmol, 1.5 eq) in dry THF (10 mL) was rapidly added by injection to the freshly prepared isocyanate. The reaction was allowed to stir at 40° C. for 4 hours followed by stirring at room temperature overnight. The mixture was concentrated under reduced pressure, and purified by flash chromatography (silica gel, 20/80 v/v n-hexane/EtOAc to 50/50 v/v n-hexane/EtOAc, then 1/99 v/v DCM/MeOH to 5/95 v/v DCM/MeOH) to afford the product as a yellow solid (0.579 g, 71%). LC/MS (4.468 min (ES$^+$)), m/z: 978.55 [M+H]$^+$. $^1$H NMR (400 MHz, CDCl$_3$) δ 8.63 (br s, 1H), 8.42 (s, 1H), 7.78 (br s, 1H), 7.53 (d, 2H, J=8.1 Hz), 7.31 (d, 2H, J=8.6 Hz), 6.76 (s, 1H), 6.59 (d, 1H, J=7.6 Hz), 6.36 (br s, 1H), 6.04 (d, 1H, J=15.9 Hz), 5.90 (m, 1H), 5.55 (m, 1H), 5.33-5.21 (m, 3H), 5.10 (s, 2H), 4.66 (m, 2H), 4.57 (dd, 2H, J=5.6, 1.0 Hz), 3.98 (dd, 1H, J=7.3, 6.8 Hz), 3.90 (m, 1H), 3.81 (m, 1H), 3.78 (s, 3H), 2.82 (dd, 1H, J=15.4, 9.6 Hz), 2.72 (dd, 1H, J=15.9, 3.5 Hz), 2.17 (m, 1H), 1.78 (dd, 3H, J=6.5, 0.8 Hz), 1.46 (d, 3H, J=7.1 Hz), 1.29 (m, 3H), 1.11 (d, 18H, J=7.1 Hz), 0.97 (d, 3H, J=6.8 Hz), 0.92 (d, 3H, J=6.8 Hz), 0.83 (s, 9H), 0.04 (s, 3H), 0.01 (s, 3H).

(b) Allyl ((S)-1-(((S)-1-((4-((((2-((S)-2-(hydroxymethyl)-4-((E)-prop-1-en-1-yl)-2,3-dihydro-1H-pyrrole-1-carbonyl)-4-methoxy-5-((triisopropylsilyl)oxy)phenyl)carbamoyl)oxy)methyl)phenyl)amino)-1-oxopropan-2-yl)amino)-3-methyl-1-oxobutan-2-yl)carbamate (15)

The silyl ether 14 (1.49 g, 1.52 mmol, 1.0 eq) was dissolved in a 7:1:1:2 mixture of acetic acid/methanol/tetrahydrofuran/ water (14:2:2:4 mL) and allowed to stir at room temperature. After 2 hours the reaction was diluted with EtOAc (100 mL), washed sequentially with water, aq. sodium bicarbonate then brine. The organic phase was then dried over MgSO$_4$, filtered and concentrated under reduced pressure. The residue was purified by flash chromatography (silica gel, 100/0 then 99/1 to 92/8 v/v DCM/MeOH) to afford the product as an orange solid (1.2 g, 92%). LC/MS (3.649 min (ES$^+$)), m/z: 865.44 [M+H]$^+$. $^1$H NMR (400 MHz, CDCl$_3$) δ 8.44 (s, 1H), 8.35 (s, 1H), 7.69 (br s, 1H), 7.53 (d, 2H, J=8.7 Hz), 7.32 (d, 2H, J=8.3 Hz), 6.78 (s, 1H), 6.56 (m, 2H), 6.32 (br s, 1H), 6.05 (d, 1H, J=14.9 Hz), 5.90 (m, 1H), 5.56 (m, 1H), 5.30 (m, 2H), 5.22 (m, 1H), 5.10 (d, 2H, J=3.1 Hz), 4.73 (m, 1H), 4.64 (m, 1H), 4.57 (d, 2H, J=5.8 Hz), 4.01 (m, 1H), 3.79 (m, 2H), 3.76 (s, 3H), 2.98 (dd, 1H, J=16.3, 10.2 Hz), 2.38 (dd, 1H, J=16.6, 4.1 Hz), 2.16 (m, 1H), 1.78 (dd, 3H, J=6.8, 0.9 Hz), 1.46 (d, 3H, J=7.1 Hz), 1.29 (m, 3H), 1.11 (d, 18H, J=7.4 Hz), 0.97 (d, 3H, J=6.7 Hz), 0.92 (d, 3H, J=6.8 Hz).

(c) (11S,11aS)-4-((S)-2-((S)-2-(allyloxycarbonylamino)-3-methylbutanamido)propanamido)benzyl 11-hydroxy-7-methoxy-5-oxo-2-((E)-prop-1-enyl)-8-(triisopropylsilyloxy)-11,11a-dihydro-1H-benzo[e]pyrrolo[1,2-a][1,4]diazepine-10(5H)-carboxylate (16)

Dry dimethyl sulfoxide (0.180 g, 2.3 mmol, 3.0 eq) was added dropwise to a solution of oxalyl chloride (0.147 g, 1.1 mmol, 1.5 eq) in DCM (10 mL) at −78° C. under an atmosphere of nitrogen. Maintaining the temperature at −78° C., after 20 minutes, a solution of the primary alcohol 15 (0.666 g, 0.77 mmol, 1.0 eq) in DCM (10 mL) was added dropwise. After a further 15 minutes, dry triethylamine (0.390 g, 3.85 mmol, 5.0 eq) was added, and the reaction mixture allowed to warm to room temperature. The reaction mixture was washed successively with cold 0.1N HCl (10 mL), saturated sodium hydrogen carbonate (10 mL) and brine (5 mL). The organic layer was then dried over MgSO$_4$, filtered and concentrated under reduced pressure. The residue was then purified by flash chromatography (silica gel, 50/50 v/v n-hexane/EtOAc to 25/75 v/v n-hexane/EtOAc) to afford the product as a white solid (0.356 g, 54%). LC/MS (3.487 min (ES$^+$)), m/z: 862.2 [M+H]$^+$. $^1$H NMR (400 MHz, CDCl$_3$) δ 8.34 (br s, 1H), 7.47 (d, 2H, J=7.6 Hz), 7.17 (s, 1H), 7.14 (d, 2H, J=7.5 Hz), 6.86 (br s, 1H), 6.65 (br s, 1H), 6.42 (d, 1H, J=7.6 Hz), 6.22 (d, 1H, J=14.4 Hz), 5.80 (m, 1H), 5.40 (m, 1H), 5.53 (m, 1H), 5.32 (m, 1H), 5.21 (d, 2H, J=9.6 Hz), 5.06 (d, 1H, J=12.3 Hz), 4.90 (m, 1H), 4.58 (m, 3H), 3.98 (m, 1H), 3.84 (m, 1H), 3.81 (s, 3H), 3.50 (m, 1H), 3.05 (dd, 1H, J=16.0, 10.3 Hz), 2.76 (m, 1H), 2.15 (m, 1H), 1.80 (dd, 3H, J=6.7, 0.8 Hz), 1.44 (d, 3H, J=7.1 Hz), 1.16 (m, 3H), 1.01 (d, 18H, J=6.6 Hz), 0.96 (d, 3H, J=6.8 Hz), 0.92 (d, 3H, J=6.8 Hz).

(d) (11S,11aS)-4-((S)-2-((S)-2-(allyloxycarbonylamino)-3-methylbutanamido)propanamido)benzyl 11-(tert-butyldimethylsilyloxy)-7-methoxy-5-oxo-2-((E)-prop-1-enyl)-8-(triisopropylsilyloxy)-11,11a-dihydro-1H-benzo[e]pyrrolo[1,2-a][1,4]diazepine-10(5H)-carboxylate (17)

Tert-butyldimethylsilyltrifluoromethane sulfonate (0.46 g, 1.74 mmol, 3.0 eq) was added to a solution of secondary alcohol 16 (0.5 g, 0.58 mmol, 1.0 eq) and 2,6-lutidine (0.25 g, 2.32 mmol, 4.0 eq) in dry DCM (10 mL) at 0° C. under an atmosphere of nitrogen. After 10 minutes, the reaction mixture was allowed to warm to room temperature and stirred for a further 120 mins. The organic phase was then washed successively with water (10 mL), saturated sodium bicarbonate (10 mL) and brine (5 mL), dried over MgSO$_4$, filtered and concentrated under reduced pressure. The residue was purified by flash chromatography (silica gel, 50/50 v/v n-hexane/EtOAc) to afford the product as a white solid (0.320 g, 57%). LC/MS (4.415 min (ES$^+$)), m/z: 976.52 [M+H]$^+$. $^1$H NMR (400 MHz, CDCl$_3$) δ 8.31 (br s, 1H), 7.48 (d, 2H, J=8.0 Hz), 7.21 (s, 1H), 7.14 (d, 2H, J=8.3 Hz), 6.89 (s, 1H), 6.65 (s, 1H), 6.38 (d, 1H, J=7.3 Hz), 6.25 (d, 1H, J=14.6 Hz), 5.93 (m, 1H), 5.85 (d, 1H, J=8.8 Hz), 5.50 (m, 1H), 5.34 (m, 1H), 5.24 (m, 2H), 5.15 (d, 1H, J=12.5 Hz), 4.86 (d, 1H, J=12.2 Hz), 4.62 (m, 3H), 4.01 (m, 1H), 3.86 (s, 3H), 3.78 (m, 1H), 3.04 (m, 1H), 2.56 (m, 1H), 2.20 (m, 1H), 1.84 (dd, 3H, J=6.6, 0.7 Hz), 1.48 (d, 3H, J=6.8 Hz), 1.20 (m, 3H), 1.05 (d, 9H, J=2.9 Hz), 1.03 (d, 9H, J=2.9 Hz), 0.99 (d, 3H, J=6.8 Hz), 0.95 (d, 3H, J=6.8 Hz), 0.88 (s, 9H), 0.27 (s, 3H), 0.14 (s, 3H).

(e) (11S,11aS)-4-((S)-2-((S)-2-(allyloxycarbonylamino)-3-methylbutanamido)propanamido)benzyl 11-(tert-butyldimethylsilyloxy)-8-hydroxy-7-methoxy-5-oxo-2-((E)-prop-1-enyl)-11,11a-dihydro-1H-benzo[e]pyrrolo[1,2-a][1,4]diazepine-10(5H)-carboxylate (18)

Lithium acetate dihydrate (0.010 g, 0.10 mmol, 1.0 eq) was added to a solution of the silyl ether 37 (0.100 g, 0.10 mmol, 1.0 eq) in wet DMF (2 mL) at 25° C. for 3 hours. The reaction mixture was then diluted with ethyl acetate (20 mL) and washed successively with 0.1M citric acid (20 mL, pH 3), water (20 mL) and brine (5 mL), dried over MgSO$_4$, filtered and concentrated under reduced pressure. The residue was purified by flash chromatography (silica gel, 5/95 v/v methanol/DCM) to afford the product as a pale yellow oil (0.070 g, 83%). LC/MS (3.362 min (ES$^+$)), m/z: 820.2 [M+H]$^+$. $^1$H NMR (400 MHz, CDCl$_3$) δ 8.39 (s, 1H), 7.48 (d, 2H, J=8.2 Hz), 7.25 (s, 1H), 7.12 (d, 2H, J=8.1 Hz), 6.88 (s, 1H), 6.68 (s, 1H), 6.47 (d, 1H, J=7.6 Hz), 6.24 (d, 1H, J=15.2 Hz), 6.03 (s, 1H), 5.92 (m, 1H), 5.84 (d, 1H, J=8.9 Hz), 5.50 (m, 1H), 5.34 (m, 1H), 5.26 (m, 2H), 5.18 (d, 1H, J=12.3 Hz), 4.80 (d, 1H, J=12.4 Hz), 4.66-4.60 (m, 3H), 4.02 (m, 1H), 3.95 (s, 3H), 3.81 (m, 1H), 3.03 (m, 1H), 2.57 (m, 1H), 2.19 (m, 1H), 1.84 (dd, 3H, J=6.8, 0.8 Hz), 1.48 (d, 3H, J=7.1 Hz), 1.00 (d, 3H, J=6.8 Hz), 0.95 (d, 3H, J=6.8 Hz), 0.87 (s, 9H), 0.26 (s, 3H), 0.12 (s, 3H).

Example 12

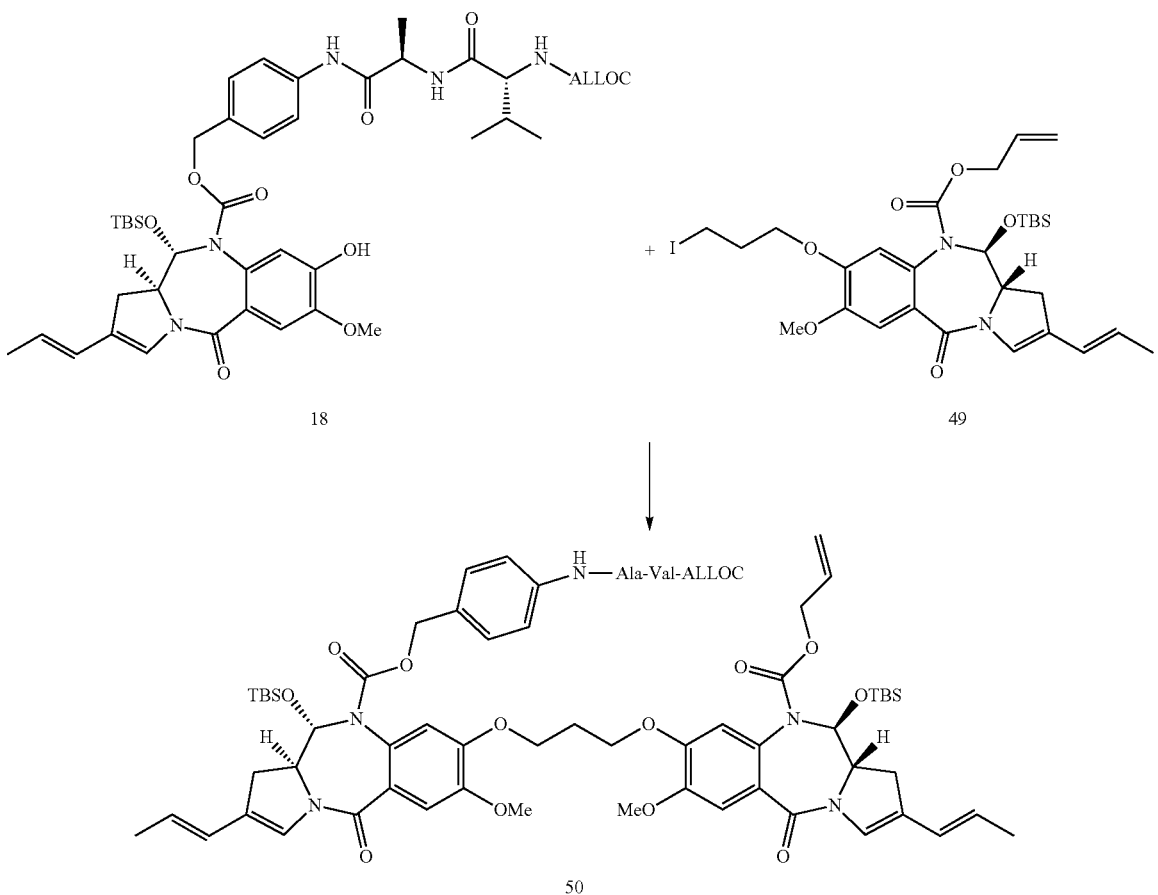

(11S,11aS)-allyl 8-(3-((11S,11aS)-10-((4-((R)-2-((R)-2-(allyloxycarbonylamino)-3-methylbutanamido)propanamido)benzyloxy)carbonyl)-11-(tert-butyldimethylsilyloxy)-7-methoxy-5-oxo-2-((E)-prop-1-enyl)-5,10,11,11a-tetrahydro-1H-benzo[e]pyrrolo[1,2-a][1,4]diazepin-8-yloxy)propoxy)-11-(tert-butyldimethylsilyloxy)-7-methoxy-5-oxo-2-((E)-prop-1-enyl)-11,11a-dihydro-1H-benzo[e]pyrrolo[1,2-a][1,4]diazepine-10(5H)-carboxylate (50)

Potassium carbonate (0.030 g, 0.21 mmol, 1.0 eq) was added to a solution of the phenol 18 (0.175 g, 0.21 mmol, 1.0 eq) and the iodo linker 49 (0.214 g, 0.32 mmol, 1.5 eq) in acetone (10 mL). The reaction mixture was heated under a nitrogen atmosphere at 75° C. in a sealed flask for 17 hours. The reaction mixture was concentrated to dryness under reduced pressure and purified by flash chromatography (silica gel, 2/98 v/v methanol/DCM to 5/95 v/v methanol/DCM) to afford the product as a pale yellow solid (0.100 g, 35%). LC/MS (4.293 min (ES+)), m/z: 1359.13 [M]+.

The invention claimed is:
1. A compound of formula I:

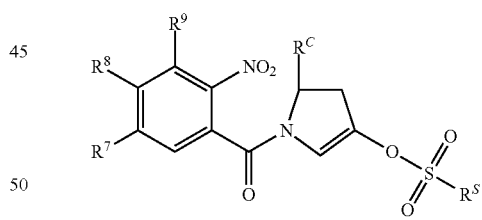

I wherein:
$R^7$ is selected from: $OR^A$, where $R^A$ is selected from $C_{1-4}$ saturated alkyl, optionally substituted by phenyl, which may bear a chloro substituent, pyridyl and furanyl; chloro; $NH_2$; —$CH_2$—O—C(=O)Me;
$R^8$ is $OProt^O$, where $Prot^O$ is a silicon-based oxygen protecting group orthogonal to $R^C$;
$R^9$ is selected from H, methyl and methoxy;
$R^S$ is selected from $CF_3$, $(CF_2)_3CF_3$, $CH_3$ and

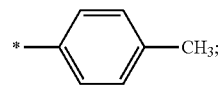 [SMILES: *c1ccc(C)cc1]

and $R^C$ is selected from:
(i) —C(=O)—OR$^{C1}$, where R$^{C1}$ is a saturated C$_{1-4}$ alkyl group;
(ii) —CH$_2$—O—C(=O)R$^{C2}$, where R$^{C2}$ is methyl or phenyl;
(iii) —CH$_2$—O—Si—(R$^{Si1}$)(R$^{Si2}$)(R$^{Si3}$), where R$^{Si1}$, R$^{Si2}$, R$^{Si3}$ are independently selected from C$_{1-6}$ a saturated alkyl group and a phenyl group; and
(iv) —C(—YR$^{C3}$)(—YR$^{C4}$) where each Y is independently O or S, and where R$^{C3}$ and R$^{C4}$ are independently a saturated C$_{1-4}$ alkyl group, or together form a C$_{2-3}$ alkylene.

2. A compound according to claim 1, wherein R$^7$ is OR$^A$, where R$^A$ is unsubstituted C$_{1-4}$ saturated alkyl.

3. A compound according to claim 1, wherein R$^S$ is CF$_3$.

4. A compound according to claim 1, wherein R$^{C1}$ is methyl.

5. A compound according to claim 1, wherein —Si—(R$^{Si1}$)(R$^{Si2}$)(R$^{Si3}$) is TBDMS.

6. A method of synthesising a compound according to claim 1 from a compound of formula II:

wherein:
R$^7$ is selected from: OR$^A$, where R$^A$ is selected from C$_{1-4}$ saturated alkyl, optionally substituted by phenyl, which may bear a chloro substituent, pyridyl and furanyl; chloro; NH$_2$; —CH$_2$—O—C(=O)Me;
R$^8$ is OProt$^O$, where Prot$^O$ is a silicon-based oxygen protecting group orthogonal to R$^C$;
R$^9$ is selected from H, methyl and methoxy; and
R$^C$ is selected from:
(i) —C(=O)—OR$^{C1}$, where R$^{C1}$ is a saturated C$_{1-4}$ alkyl group;
(ii) —CH$_2$—O—C(=O)R$^{C2}$, where R$^{C2}$ is methyl or phenyl;
(iii) —CH$_2$—O—Si—(R$^{Si1}$)(R$^{Si2}$)(R$^{Si3}$), where R$^{Si1}$, R$^{Si2}$, R$^{Si3}$ are independently selected from C$_{1-6}$ a saturated alkyl group and a phenyl group; and
(iv) —C(—YR$^{C3}$)(—YR$^{C4}$) where each Y is independently O or S, and where R$^{C3}$ and R$^{C4}$ are independently a saturated C$_{1-4}$ alkyl group, or together form a C$_{2-3}$ alkylene;
comprising treating II with the appropriate anhydride and anhydrous 2,6-lutidine or anhydrous 2,6-tBu-pyridine at a temperature of −35° C. or lower in a dry organic solvent under an inert atmosphere.

7. A compound of formula III:

wherein:
R$^7$ is selected from: OR$^A$, where R$^A$ is selected from C$_{1-4}$ saturated alkyl, optionally substituted by phenyl, which may bear a chloro substituent, pyridyl and furanyl; chloro; NH$_2$; —CH$_2$—O—C(=O)Me;
R$^8$ is OProt$^O$, where Prot$^O$ is a silicon-based oxygen protecting group orthogonal to R$^C$;
R$^9$ is selected from H, methyl and methoxy;
R$^C$ is selected from:
(i) —C(=O)—OR$^{C1}$, where R$^{C1}$ is a saturated C$_{1-4}$ alkyl group;
(ii) —CH$_2$—O—C(=O)R$^{C2}$, where R$^{C2}$ is methyl or phenyl;
(iii) —CH$_2$—O—Si—(R$^{Si1}$)(R$^{Si2}$)(R$^{Si3}$), where R$^{Si1}$, R$^{Si2}$, R$^{Si3}$ are independently selected from C$_{1-6}$ a saturated alkyl group and a phenyl group; and
(iv) —C(—YR$^{C3}$)(—YR$^{C4}$) where each Y is independently O or S, and where R$^{C3}$ and R$^{C4}$ are independently a saturated C$_{1-4}$ alkyl group, or together form a C$_{2-3}$ alkylene; and
R$^2$ is selected from:
(i) an optionally substituted C$_{5-20}$ aryl group;
(ii) an optionally substituted C$_{1-6}$ alkyl group; and
(iii) H.

8. A method of synthesising a compound according to claim 7 from a compound of formula I:

wherein:
R$^7$ is selected from: OR$^A$, where R$^A$ is selected from C$_{1-4}$ saturated alkyl, optionally substituted by phenyl, which may bear a chloro substituent, pyridyl and furanyl; chloro; NH$_2$; —CH$_2$—O—C(=O)Me;
R$^8$ is OProt$^O$, where Prot$^O$ is a silicon-based oxygen protecting group orthogonal to R$^C$;
R$^9$ is selected from H, methyl and methoxy;
R$^S$ is selected from CF$_3$, (CF$_2$)$_3$CF$_3$, CH$_3$ and and $R^C$ is selected from:
(i) —C(═O)—$OR^{C1}$, where $R^{C1}$ is a saturated $C_{1-4}$ alkyl group;
(ii) —$CH_2$—O—C(═O)$R^{C2}$, where $R^{C2}$ is methyl or phenyl;
(iii) —$CH_2$—O—Si—($R^{Si1}$)($R^{Si2}$)($R^{Si3}$), where $R^{Si1}$, $R^{Si2}$, $R^{Si3}$ are independently selected from $C_{1-6}$ a saturated alkyl group and a phenyl group; and
(iv) —C(—$YR^{C3}$)(—$YR^{C4}$) where each Y is independently O or S, and where $R^{C3}$ and $R^{C4}$ are independently a saturated $C_{1-4}$ alkyl group, or together form a $C_{2-3}$ alkylene;

by:
(i) a Suzuki coupling between a compound of formula I and an appropriate aryl boron derivative;
(ii) a Heck coupling with an appropriate alkene, acrylamide or acrylate;
(iii) a Stille coupling with an appropriate organotin reagent;
(iv) a Sonagishira coupling with an appropriate alkyne; or
(v) a hydride transfer using a triethylsilane.

9. A compound of formula IV:

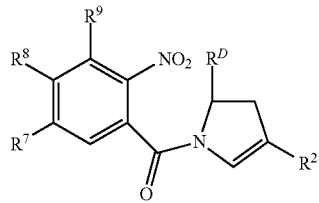

IV wherein:
$R^7$ is selected from: $OR^A$, where $R^A$ is selected from $C_{1-4}$ saturated alkyl, optionally substituted by phenyl, which may bear a chloro substituent, pyridyl and furanyl; chloro; $NH_2$; —$CH_2$—O—C(═O)Me;
$R^8$ is $OProt^O$, where $Prot^O$ is a silicon-based oxygen protecting group orthogonal to $R^C$;
$R^9$ is selected from H, methyl and methoxy;
$R^2$ is selected from:
(i) an optionally substituted $C_{5-20}$ aryl group;
(ii) an optionally substituted $C_{1-5}$ alkyl group; and
(iii) H;
$R^D$ is selected from:
(ii) —$CH_2$—O—C(═O)$R^{C2}$, where $R^{C2}$ is methyl or phenyl;
(iii) —$CH_2$—O—Si—($R^{Si1}$)($R^{Si2}$)($R^{Si3}$), where $R^{Si1}$, $R^{Si2}$, $R^{Si3}$ are independently selected from $C_{1-6}$ saturated alkyl group and a phenyl group; and
(iv) —C(—$YR^{C3}$)(—$YR^{C4}$) where each Y is independently O or S, and where $R^{C3}$ and $R^{C4}$ are independently a saturated $C_{1-4}$ alkyl group, or together form a $C_{2-3}$ alkylene.

10. A compound according to claim 9, wherein —Si—($R^{Si1}$)($R^{Si2}$)($R^{Si3}$) is TBDMS.

11. A compound according to claim 9, wherein $R^{C2}$ is methyl.

12. A method of synthesising a compound according to claim 9 from a compound of formula III:

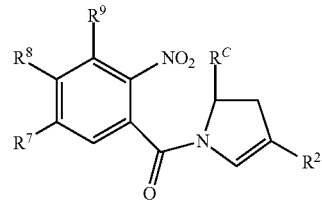

III wherein:
$R^7$ is selected from: $OR^A$, where $R^A$ is selected from $C_{1-4}$ saturated alkyl, optionally substituted by phenyl, which may bear a chloro substituent, pyridyl and furanyl; chloro; $NH_2$; —$CH_2$—O—C(═O)Me;
$R^8$ is $OProt^O$, where $Prot^O$ is a silicon-based oxygen protecting group orthogonal to $R^C$;
$R^9$ is selected from H, methyl and methoxy;
$R^C$ is selected from:
(i) —C(═O)—$OR^{C1}$, where $R^{C1}$ is a saturated $C_{1-4}$ alkyl group;
(ii) —$CH_2$—O—C(═O)$R^{C2}$, where $R^{C2}$ is methyl or phenyl;
(iii) —$CH_2$—O—Si—($R^{Si1}$)($R^{Si2}$)($R^{Si3}$), where $R^{Si1}$, $R^{Si2}$, $R^{Si3}$ are independently selected from $C_{1-6}$ a saturated alkyl group and a phenyl group; and
(iv) —C(—$YR^{C3}$)(—$YR^{C4}$) where each Y is independently O or S, and where $R^{C3}$ and $R^{C4}$ are independently a saturated $C_{1-4}$ alkyl group, or together form a $C_{2-3}$ alkylene;
$R^2$ is selected from:
(i) an optionally substituted $C_{5-20}$ aryl group;
(ii) an optionally substituted $C_{1-6}$ alkyl group; and
(iii) H;
by:
(i) if $R^C$ is —C(═O)—$OR^{C1}$, conversion of —C(═O)—$OR^{C1}$ to —$CH_2$—O—C(═O)$R^{C2}$ or —$CH_2$—O—Si—($R^{Si1}$)($R^{Si2}$)($R^{Si3}$), followed by:
(ii) if $R^C$ is —$CH_2$—O—C(═O)$R^{C2}$, reduction of the nitro group by zinc in acetic acid or if $R^C$ is —$CH_2$—O—Si—($R^{Si1}$)($R^{Si2}$)($R^{Si3}$), reduction of the nitro group using zinc in 5% formic acid in ethanol;
(iii) if $R^C$ is —C(—$YR^{C3}$)(—$YR^{C4}$), reduction of the nitro group using Cd/Pb couple, sodium dithionite or tin II chloride.

13. A compound of formula V:

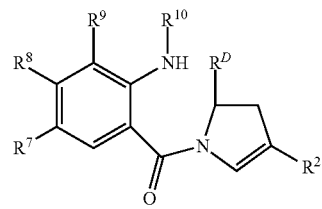

V wherein:
$R^7$ is selected from: $OR^A$, where $R^A$ is selected from $C_{1-4}$ saturated alkyl, optionally substituted by phenyl, which may bear a chloro substituent, pyridyl and furanyl; chloro; $NH_2$; —$CH_2$—O—C(═O)Me;
$R^8$ is $OProt^O$, where $Prot^O$ is a silicon-based oxygen protecting group orthogonal to $R^C$;
$R^9$ is selected from H, methyl and methoxy;

$R^2$ is selected from:
(i) an optionally substituted $C_{5-20}$ aryl group;
(ii) an optionally substituted $C_{1-5}$ alkyl group; and
(iii) H;
$R^P$ is selected from:
(ii) —$CH_2$—O—C(=O)$R^{C2}$, where $R^{C2}$ is methyl or phenyl;
(iii) —$CH_2$—O—Si—($R^{Si1}$)($R^{Si2}$)($R^{Si3}$), where $R^{Si1}$, $R^{Si2}$, $R^{Si3}$ are independently selected from $C_{1-6}$ saturated alkyl group and a phenyl group; and
(iv) —C(—$YR^{C3}$)(—$YR^{C4}$) where each Y is independently O or S, and where $R^{C3}$ and $R^{C4}$ are independently a saturated $C_{1-4}$ alkyl group, or together form a $C_{2-3}$ alkylene;
$R^{10}$ is a carbamate-based nitrogen protecting group, which is palladium-labile and/or labile under the conditions used to add the group:

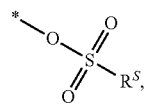

or contains a moiety which is palladium-labile and/or is labile under the conditions used to add the group:

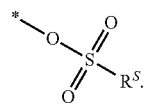

14. A compound according to claim 13, wherein $R^{10}$ is selected from one of:

DBD-Tmoc

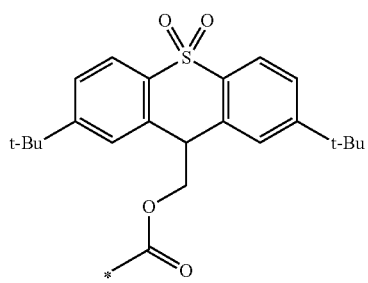 [SMILES: CC(=O)OCC1c2cc(C(C)(C)C)ccc2S(=O)(=O)c2ccc(C(C)(C)C)cc21]

Cbz (benzyl carbamate)

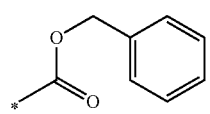

Voc (Vinyl carbamate)

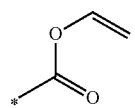

1,1-dimethylpropynyl carbamate

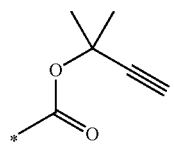

Alloc (Allyl carbamate)

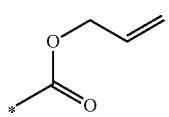

Moz (p-methoxybenzylcarbamate)

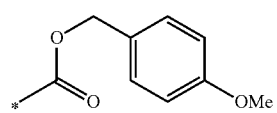

Ipaoc (1-isopropylallyl carbamate)

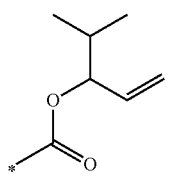

PNZ (p-nitrobenzylcarbamate)

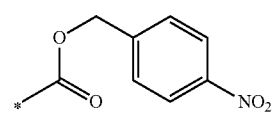

Coc (Cinnamyl carbamate)

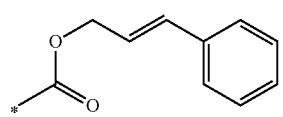

3,4-dimethoxy-6-nitrobenzyl carbamate

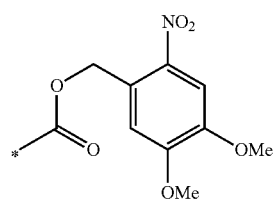 [SMILES: COc1cc(COC(C)=O)c([N+](=O)[O-])cc1OC]

Noc (4-nitrocinnamyl carbamate)

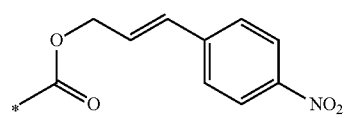 [SMILES: CC(=O)OC/C=C/c1ccc([N+](=O)[O-])cc1]

p-bromobenzyl carbamate

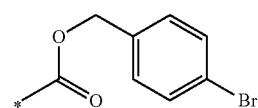

| | | | |
|---|---|---|---|
| Paloc (3-(3'-pyridyl)prop-2-enyl carbamate) | 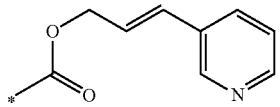 | p-chlorobenzyl carbamate | 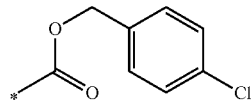 |
| N-hydroxypiperidinyl carbamate | 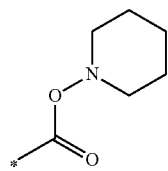 | 2,4-dichlorobenzyl carbamate | 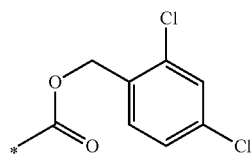 |
| 1,1-dimethyl-2-bromoethyl carbamate | 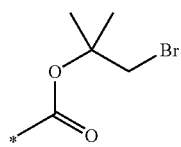 | Bic (5-benzylisoxazolylmethyl) | 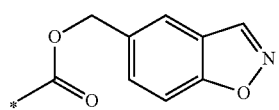 |
| 1,1-dimethyl-2-chloroethyl carbamate | 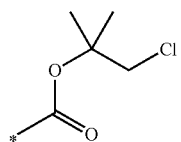 | Diphenylmethyl carbamate | 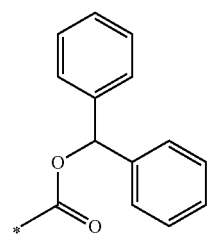 |
| 1,1-dimethyl-2-cyanoethyl carbamate | 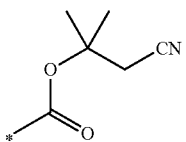 | 9-anthrylmethyl carbamate | 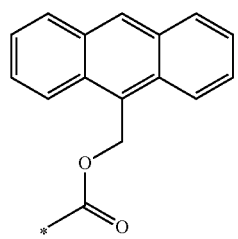 |
| Propynyl carbamate | 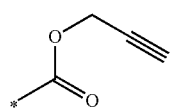 | S-benzyl carbamate | 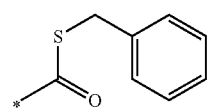 | where the asterisk indicates the point of attachment to the N10 position.

15. A compound according to claim 13, wherein $R^{10}$ is of the formula:

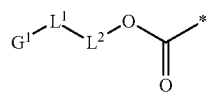

where the asterisk indicates the point of attachment to the N10 position, $G^1$ is a functional group to form a connection to a cell binding agent, $L^1$ is a cleavable linker, $L^2$ is a covalent bond or together with —OC(=O)— forms a self-immolative linker.

16. A method of synthesising a compound according to claim 13 from a compound of formula IV:

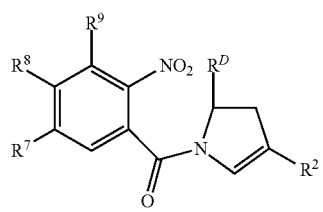

wherein:

$R^7$ is selected from: $OR^A$, where $R^A$ is selected from $C_{1-4}$ saturated alkyl, optionally substituted by phenyl, which may bear a chloro substituent, pyridyl and furanyl; chloro; $NH_2$; —$CH_2$—O—C(=O)Me;

$R^8$ is $OProt^O$, where $Prot^O$ is a silicon-based oxygen protecting group orthogonal to $R^C$;

$R^9$ is selected from H, methyl and methoxy;

R² is selected from:
(i) an optionally substituted $C_{5-20}$ aryl group;
(ii) an optionally substituted $C_{1-5}$ alkyl group; and
(iii) H;

$R^D$ is selected from:
(ii) —$CH_2$—O—C(=O)$R^{C2}$, where $R^{C2}$ is methyl or phenyl;
(iii) —$CH_2$—O—Si—($R^{Si1}$)($R^{Si2}$)($R^{Si3}$), where $R^{Si1}$, $R^{Si2}$, $R^{Si3}$ are independently selected from $C_{1-6}$ saturated alkyl group and a phenyl group; and
(iv) —C(—$YR^{C3}$)(—$YR^{C4}$) where each Y is independently O or S, and where $R^{C3}$ and $R^{C4}$ are independently a saturated $C_{1-4}$ alkyl group, or together form a $C_{2-3}$ alkylene;

by reaction of IV with triphosgene to obtain the isocyanate followed by reaction with $R^{10}$—OH.

17. A compound of formula VI:

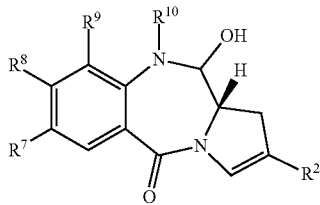

VI wherein:
$R^7$ is selected from: $OR^A$, where $R^A$ is selected from $C_{1-4}$ saturated alkyl, optionally substituted by phenyl, which may bear a chloro substituent, pyridyl and furanyl; chloro; $NH_2$; —$CH_2$—O—C(=O)Me;
$R^8$ is $OProt^O$, where $Prot^O$ is a silicon-based oxygen protecting group orthogonal to $R^C$;
$R^9$ is selected from H, methyl and methoxy;
$R^2$ is selected from:
(i) an optionally substituted $C_{5-20}$ aryl group;
(ii) an optionally substituted $C_{1-5}$ alkyl group; and
(iii) H; and
$R^{10}$ is a carbamate-based nitrogen protecting group, which is palladium-labile and/or labile under the conditions used to add the group:

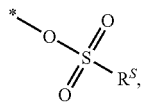

or contains a moiety which is palladium-labile and/or is labile under the conditions used to add the group:

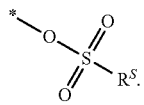

18. A method of synthesising a compound according to claim 17 from a compound of formula V:

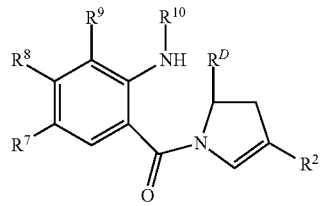

V wherein:
$R^7$ is selected from: $OR^A$, where $R^A$ is selected from $C_{1-4}$ saturated alkyl, optionally substituted by phenyl, which may bear a chloro substituent, pyridyl and furanyl; chloro; $NH_2$; —$CH_2$—O—C(=O)Me;
$R^8$ is $OProt^O$, where $Prot^O$ is a silicon-based oxygen protecting group orthogonal to $R^C$;
$R^9$ is selected from H, methyl and methoxy;
$R^2$ is selected from:
(i) an optionally substituted $C_{5-20}$ aryl group;
(ii) an optionally substituted $C_{1-5}$ alkyl group; and
(iii) H;

$R^D$ is selected from:
(ii) —$CH_2$—O—C(=O)$R^{C2}$, where $R^{C2}$ is methyl or phenyl;
(iii) —$CH_2$—O—Si—($R^{Si1}$)($R^{Si2}$)($R^{Si3}$), where $R^{Si1}$, $R^{Si2}$, $R^{Si3}$ are independently selected from $C_{1-6}$ saturated alkyl group and a phenyl group; and
(iv) —C(—$YR^{C3}$)(—$YR^{C4}$) where each Y is independently O or S, and where $R^{C3}$ and $R^{C4}$ are independently a saturated $C_{1-4}$ alkyl group, or together form a $C_{2-3}$ alkylene;

$R^{10}$ is a carbamate-based nitrogen protecting group, which is palladium-labile and/or labile under the conditions used to add the group:

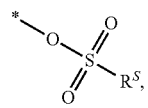

or contains a moiety which is palladium-labile and/or is labile under the conditions used to add the group:

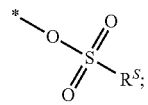

by:
(a) (i) where $R^D$ is —$CH_2$—O—C(=O)Me, removal of the acetate protecting group, with potassium carbonate in aqueous methanol, or with lithium triethylborohydride;
(ii) where $R^D$ is —$CH_2$—O—Si—($R^{Si1}$)($R^{Si2}$)($R^{Si3}$), removal of the silyl ether protecting group using: TBAF in THF; acetic acid in aqueous THF; CsF in DMF; or HF in pyridine; and
(b) oxidation of the product of step (a); or
(c) where $R^D$ is —C(—$YR^{C3}$)(—$YR^{C4}$), removal of the acetal or thioacetal protecting groups, respectively with acid or reaction with Hg (II) salts.

19. A method according to claim 18, wherein the oxidation is carried out with Dess-Martin periodinane.

20. A compound of formula VII:

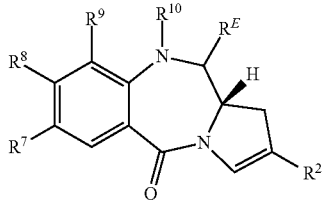

wherein:
$R^7$ is selected from: $OR^A$, where $R^A$ is selected from $C_{1-4}$ saturated alkyl, optionally substituted by phenyl, which may bear a chloro substituent, pyridyl and furanyl; chloro; $NH_2$; —$CH_2$—O—C(=O)Me;
$R^8$ is $OProt^O$, where $Prot^O$ is a silicon-based oxygen protecting group orthogonal to $R^C$;
$R^9$ is selected from H, methyl and methoxy;
$R^2$ is selected from:
(i) an optionally substituted $C_{5-20}$ aryl group;
(ii) an optionally substituted $C_{1-5}$ alkyl group; and
(iii) H;
$R^{10}$ is a carbamate-based nitrogen protecting group, which is palladium-labile and/or labile under the conditions used to add the group:

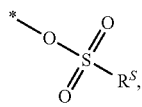

or contains a moiety which is palladium-labile and/or is labile under the conditions used to add the group:

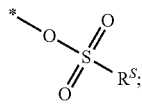

and
$R^E$ is selected from the group consisting of: O—$C_{1-2}$ alkyl; O—Si—$(R^{Si1})(R^{Si2})(R^{Si3})$, where $R^{Si1}$, $R^{Si2}$, $R^{Si3}$ are as defined above; O—$CH_2OCH_3$ (OMOM), O—$CH_2OC_2H_4OCH_3$ (OMEM), $OC_5H_{10}$ (THP).

21. A compound according to claim 20, wherein $R^E$ is O-TBS.

22. A method of synthesising a compound according to claim 20 from a compound of formula VI:

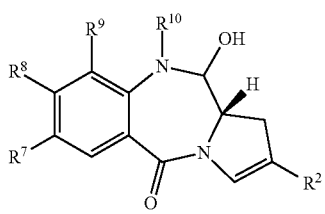

wherein:
$R^7$ is selected from: $OR^A$, where $R^A$ is selected from $C_{1-4}$ saturated alkyl, optionally substituted by phenyl, which may bear a chloro substituent, pyridyl and furanyl; chloro; $NH_2$; —$CH_2$—O—C(=O)Me;
$R^8$ is $OProt^O$, where $Prot^O$ is a silicon-based oxygen protecting group orthogonal to $R^C$;
$R^9$ is selected from H, methyl and methoxy;
$R^2$ is selected from:
(i) an optionally substituted $C_{5-20}$ aryl group;
(ii) an optionally substituted $C_{1-5}$ alkyl group; and
(iii) H;
$R^{10}$ is a carbamate-based nitrogen protecting group, which is palladium-labile and/or labile under the conditions used to add the group:

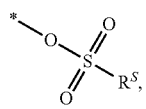

or contains a moiety which is palladium-labile and/or is labile under the conditions used to add the group:

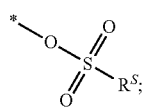

by adding a protecting group to OH to yield $R^E$.

23. A compound of formula VIII:

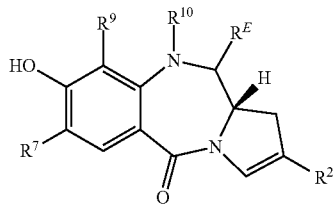

wherein:
$R^7$ is selected from: $OR^A$, where $R^A$ is selected from $C_{1-4}$ saturated alkyl, optionally substituted by phenyl, which may bear a chloro substituent, pyridyl and furanyl; chloro; $NH_2$; —$CH_2$—O—C(=O)Me;
$R^9$ is selected from H, methyl and methoxy;
$R^2$ is selected from:
(i) an optionally substituted $C_{5-20}$ aryl group;
(ii) an optionally substituted $C_{1-5}$ alkyl group; and
(iii) H;
$R^{10}$ is a carbamate-based nitrogen protecting group, which is palladium-labile and/or labile under the conditions used to add the group:

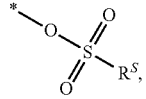

or contains a moiety which is palladium-labile and/or is labile under the conditions used to add the group:

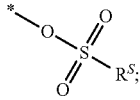

and $R^E$ is selected from the group consisting of: O—$C_{1-2}$ alkyl; O—Si—$(R^{Si1})(R^{Si2})(R^{Si3})$, where $R^{Si1}$, $R^{Si2}$, $R^{Si3}$ are as defined above; O—$CH_2OCH_3$ (OMOM), O—$CH_2OC_2H_4OCH_3$ (OMEM), $OC_5H_{10}$ (THP).

24. A method of synthesising a compound according to claim 23 from a compound of formula VII:

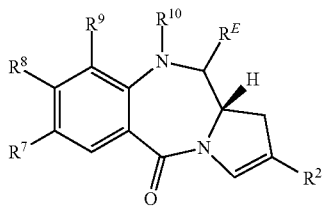

wherein:
$R^7$ is selected from: $OR^A$, where $R^A$ is selected from $C_{1-4}$ saturated alkyl, optionally substituted by phenyl, which may bear a chloro substituent, pyridyl and furanyl; chloro; $NH_2$; —$CH_2$—O—C(=O)Me;
$R^8$ is $OProt^O$, where $Prot^O$ is a silicon-based oxygen protecting group orthogonal to $R^C$;
$R^9$ is selected from H, methyl and methoxy;
$R^2$ is selected from:
(i) an optionally substituted $C_{5-20}$ aryl group;
(ii) an optionally substituted $C_{1-5}$ alkyl group; and
(iii) H;
$R^{10}$ is a carbamate-based nitrogen protecting group, which is palladium-labile and/or labile under the conditions used to add the group:

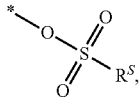

or contains a moiety which is palladium-labile and/or is labile under the conditions used to add the group:

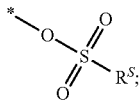

and
$R^E$ is selected from the group consisting of: O—$C_{1-2}$ alkyl; O—Si—$(R^{Si1})(R^{Si2})(R^{Si3})$, where $R^{Si1}$, $R^{Si2}$, $R^{Si3}$ are as defined above; O—$CH_2OCH_3$ (OMOM), O—$CH_2OC_2H_4OCH_3$ (OMEM), $OC_5H_{10}$ (THP);
by:
removing the protecting group in $R^8$ to yield OH.

25. A compound of formula IX:

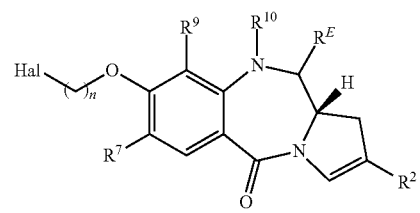

wherein:
$R^7$ is selected from: $OR^A$, where $R^A$ is selected from $C_{1-4}$ saturated alkyl, optionally substituted by phenyl, which may bear a chloro substituent, pyridyl and furanyl; chloro; $NH_2$; —$CH_2$—O—C(=O)Me;
$R^9$ is selected from H, methyl and methoxy;
$R^2$ is selected from:
(i) an optionally substituted $C_{5-20}$ aryl group;
(ii) an optionally substituted $C_{1-5}$ alkyl group; and
(iii) H;
$R^{10}$ is a carbamate-based nitrogen protecting group, which is palladium-labile and/or labile under the conditions used to add the group:

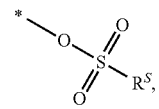

or contains a moiety which is palladium-labile and/or is labile under the conditions used to add the group:

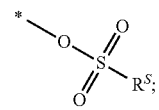

$R^E$ is selected from the group consisting of: O—$C_{1-2}$ alkyl; O—Si—$(R^{Si1})(R^{Si2})(R^{Si3})$, where $R^{Si1}$, $R^{Si2}$, $R^{Si3}$ are as defined above; O—$CH_2OCH_3$ (OMOM), O—$CH_2OC_2H_4OCH_3$ (OMEM), $OC_5H_{10}$ (THP);
n is from 1 to 12 and Hal is selected from I, Cl and Br.

26. A method of synthesising a compound according to claim 25 from a compound of formula VIII:

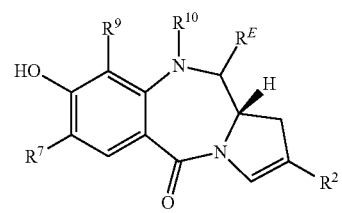

wherein:
$R^7$ is selected from: $OR^A$, where $R^A$ is selected from $C_{1-4}$ saturated alkyl, optionally substituted by phenyl, which may bear a chloro substituent, pyridyl and furanyl; chloro; $NH_2$; —$CH_2$—O—C(=O)Me;

$R^9$ is selected from H, methyl and methoxy;
$R^2$ is selected from:
(i) an optionally substituted $C_{5-20}$ aryl group;
(ii) an optionally substituted $C_{1-5}$ alkyl group; and
(iii) H;
$R^{10}$ is a carbamate-based nitrogen protecting group, which is palladium-labile and/or labile under the conditions used to add the group:

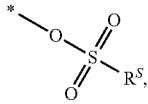

or contains a moiety which is palladium-labile and/or is labile under the conditions used to add the group:

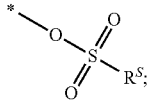

and
$R^E$ is selected from the group consisting of: O—$C_{1-2}$ alkyl; O—Si—($R^{Si1}$)($R^{Si2}$)($R^{Si3}$), where $R^{Si1}$, $R^{Si2}$, $R^{Si3}$ are as defined above; O—$CH_2OCH_3$ (OMOM), O—$CH_2OC_2H_4OCH_3$ (OMEM), $OC_5H_{10}$ (THP);
by reacting with a compound of formula X:

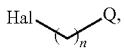

wherein Q is selected from I, Cl and Br.

27. A compound of formula XI:

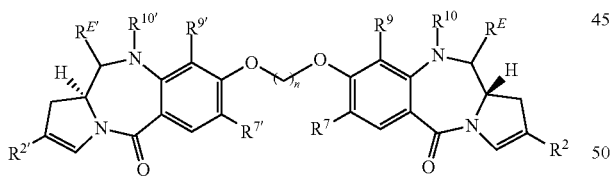

wherein:
$R^7$ is selected from: $OR^A$, where $R^A$ is selected from $C_{1-4}$ saturated alkyl, optionally substituted by phenyl, which may bear a chloro substituent, pyridyl and furanyl; chloro; $NH_2$; —$CH_2$—O—C(=O)Me;
$R^9$ is selected from H, methyl and methoxy;
$R^2$ is selected from:
(i) an optionally substituted $C_{5-20}$ aryl group;
(ii) an optionally substituted $C_{1-5}$ alkyl group; and
(iii) H;
$R^{10}$ is a carbamate-based nitrogen protecting group, which is palladium-labile and/or labile under the conditions used to add the group:

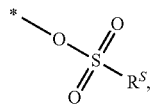

or contains a moiety which is palladium-labile and/or is labile under the conditions used to add the group:

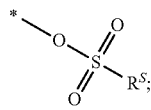

$R^E$ is selected from the group consisting of: O—$C_{1-2}$ alkyl; O—Si—($R^{Si1}$)($R^{Si2}$)($R^{Si3}$), where $R^{Si1}$, $R^{Si2}$, $R^{Si3}$ are as defined above; O—$CH_2OCH_3$ (OMOM), O—$CH_2OC_2H_4OCH_3$ (OMEM), $OC_5H_{10}$ (THP);
where n is from 1 to 12;
and where $R^{2'}$, $R^{7'}$, $R^{9'}$, $R^{10'}$ and $R^{E'}$ are independently selected from the same groups as $R^2$, $R^7$, $R^9$, $R^{10}$ and $R^E$ respectively.

28. A method of synthesising a compound according to claim 27 comprising coupling compounds of formulae VIII and IX:

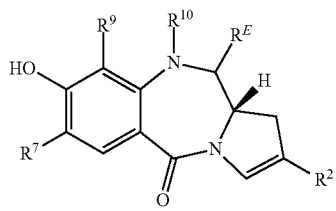

wherein:
$R^7$ is selected from: $OR^A$, where $R^A$ is selected from $C_{1-4}$ saturated alkyl, optionally substituted by phenyl, which may bear a chloro substituent, pyridyl and furanyl; chloro; $NH_2$; —$CH_2$—O—C(=O)Me;
$R^8$ is $OProt^O$, where $Prot^O$ is a silicon-based oxygen protecting group orthogonal to $R^C$;
$R^9$ is selected from H, methyl and methoxy;
$R^2$ is selected from:
(i) an optionally substituted $C_{5-20}$ aryl group;
(ii) an optionally substituted $C_{1-5}$ alkyl group; and
(iii) H;
$R^{10}$ is a carbamate-based nitrogen protecting group, which is palladium-labile and/or labile under the conditions used to add the group:

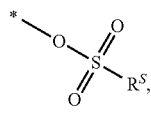

or contains a moiety which is palladium-labile and/or is labile under the conditions used to add the group:

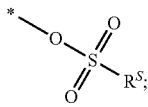

and $R^E$ is selected from the group consisting of: O—$C_{1-2}$ alkyl; O—Si—($R^{Si1}$)($R^{Si2}$)($R^{Si3}$), where $R^{Si1}$, $R^{Si2}$, $R^{Si3}$ are as defined above; O—$CH_2OCH_3$ (OMOM), O—$CH_2OC_2H_4OCH_3$ (OMEM), $OC_5H_{10}$ (THP);

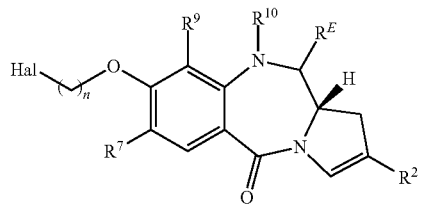

IX wherein:

$R^7$ is selected from: $OR^A$, where $R^A$ is selected from $C_{1-4}$ saturated alkyl, optionally substituted by phenyl, which may bear a chloro substituent, pyridyl and furanyl; chloro; $NH_2$; —$CH_2$—O—C(=O)Me;

$R^9$ is selected from H, methyl and methoxy;

$R^2$ is selected from:
(i) an optionally substituted $C_{5-20}$ aryl group;
(ii) an optionally substituted $C_{1-5}$ alkyl group; and
(iii) H;

$R^{10}$ is a carbamate-based nitrogen protecting group, which is palladium-labile and/or labile under the conditions used to add the group:

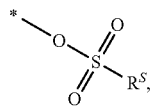

or contains a moiety which is palladium-labile and/or is labile under the conditions used to add the group:

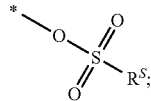

$R^E$ is selected from the group consisting of: O—$C_{1-2}$ alkyl; O—Si—($R^{Si1}$)($R^{Si2}$)($R^{Si3}$), where $R^{Si1}$, $R^{Si2}$, $R^{Si3}$ are as defined above; O—$CH_2OCH_3$ (OMOM), O—$CH_2OC_2H_4OCH_3$ (OMEM), $OC_5H_{10}$ (THP);

n is from 1 to 12 and Hal is selected from I, Cl and Br.

29. The method according to claim 28, wherein the reaction is carried out in refluxing acetone in the presence of $K_2CO_3$.

* * * * *